(12) United States Patent
Andersen et al.

(10) Patent No.: US 7,364,855 B2
(45) Date of Patent: Apr. 29, 2008

(54) METHODS AND KITS FOR METHYLATION DETECTION

(75) Inventors: Mark R. Andersen, Carlsbad, CA (US); Jer-Kang Chen, Palo Alto, CA (US); Michael W. Hunkapiller, San Carlos, CA (US); Steven M. Menchen, Fremont, CA (US)

(73) Assignee: Applera Corporation, Foster City, CA (US)

( * ) Notice: Subject to any disclaimer, the term of this patent is extended or adjusted under 35 U.S.C. 154(b) by 175 days.

(21) Appl. No.: 11/119,985

(22) Filed: May 2, 2005

(65) Prior Publication Data

US 2005/0266458 A1  Dec. 1, 2005

Related U.S. Application Data

(60) Provisional application No. 60/567,396, filed on Apr. 30, 2004.

(51) Int. Cl.
 *C12Q 1/68* (2006.01)
 *C07H 21/02* (2006.01)
 *C07H 21/04* (2006.01)

(52) U.S. Cl. .................. 435/6; 536/23.1; 536/24.3

(58) Field of Classification Search ............ 435/6; 536/23.1, 24.3
 See application file for complete search history.

(56) References Cited

U.S. PATENT DOCUMENTS

| | | | |
|---|---|---|---|
| 4,988,617 A | | 1/1991 | Landegren et al. |
| 5,494,810 A | * | 2/1996 | Barany et al. ........... 435/91.52 |
| 5,700,672 A | | 12/1997 | Mathur et al. |
| 6,027,889 A | * | 2/2000 | Barany et al. ................. 435/6 |
| 6,331,393 B1 | | 12/2001 | Laird et al. |
| 2003/0119025 A1 | * | 6/2003 | Olek et al. ..................... 435/6 |
| 2005/0053957 A1 | * | 3/2005 | Rosenblum .................... 435/6 |
| 2005/0272071 A1 | * | 12/2005 | Lao et al. ...................... 435/6 |
| 2006/0121492 A1 | * | 6/2006 | Zon ............................... 435/6 |

FOREIGN PATENT DOCUMENTS

| | | |
|---|---|---|
| EP | 0 976 835 A1 | 2/2000 |
| WO | WO 91/17239 | 11/1991 |
| WO | WO 96/15271 | 5/1996 |
| WO | WO 01/62961 * | 8/2001 |
| WO | WO 03/057909 A2 | 7/2003 |
| WO | WO 2004/048614 A1 | 6/2004 |
| WO | WO 2005/024053 A1 | 3/2005 |

OTHER PUBLICATIONS

Conner et al.., Detection of βs-globin allele by hybridization with synthetic oligonucleotides. PNAS 80 : 278-282(1983).*
Saiki et al. , Analysis of enzymatically amplified β-globin and HLA-DQα DNA with allele-specific oligonucleotide probes. Nature 324: 163-166 (1986).*
Heid et al., Real Time quantitative PCR. Genome Research 6 :986-994 (1996).*
McGrew et al., Quantitation of genomic methylation using ligation-mediated PCR. Biotechniques 15(4) : 722-729 (1993).*
S. Steigerwald et al., "Ligation-Mediated PCR Improves The Sensitivity Of Methylation Analysis By Restriction Enzymes And Detection Of Specific DNA Strand Breaks" Nucleic Acids Research, vol. 18, No. 6, Feb. 11, 1990, pp. 1435-1439.
Z. Xiong et al., COBRA: A Sensitive And Quantitative DNA Methylation Assay, Nucleic Acids Research, vol. 25, No. 12, Apr. 18, 1997, pp. 2532-2534.
International Search Report mailed Feb. 14, 2006 issued in PCT/US2005/015152, 12 pages.
M. Angers et al., "Optimal Conditions To Use Pfu exo DNA Polymerase For Highly Efficient Ligation-Mediated Polymerase Chain Reaction Protocols", Nucleic Acids Research, 2001, vol. 29, No. 16 e83, pp. 1-11.
F. Barany, "Genetic Disease Detection And DNA Amplification Using Cloned Thermostable Ligase", Proc. Natl. Acad. Sci. USA, vol. 88, Jan. 1991, pp. 189-193.
W. Bi et al., "CCR: A Rapid And Simple Approach For Mutation Detection", Nucleic Acids Research, 1997, vol. 25, No. 14, pp. 2949-2951.
W. Cao, "Recent Developments In Ligase-Mediated Amplification And Detection", Trends in Biotechnology, vol. 22, No. 1, Jan. 2004, pp. 38-44.
C. Eads et al., "MethyLight: A High-Throughput Assay To Measure DNA Methylation", Nucleic Acids Research, 2000, vol. 28, No. 8 e32, pp. i-viii.
D. Faulhammer et al., "Fidelity Of Enzymatic Ligation For DNA Computing", Journal of Computational Biology, vol. 7 No. 6, 2000, pp. 839-848.
M. Fraga et al., "DNA Methylation: A Profile Of Methods And Applications" BioTechniques, vol. 33, Sep. 2002, pp. 632-649.
J. Herman et al., "Methylation-Specific PCR: A Novel PCR Assay For Methylation Status Of CpG Islands", Proc. Natl. Acad. Sci. USA, vol. 93, Sep. 1996, pp. 9821-9826.
J. N. Housby et al., "Optimised Ligation Of Oligonucleotides By Thermal Ligases: Comparison Of *Thermus scotoductus* And *Rhodothermus marinus* DNA Ligases To Other Thermophilic Ligases", Nucleic Acids Research, 2000, vol. 28, No. 3 e10, pp. i-v.
J. N. Housby et al., "Fidelity Of DNA Ligation: A Novel Experimental Approach Based On The Polymerisation Of Libraries Of Oligonucleotides", Nucleic Acids Research, 1998, vol. 26, No. 18, pp. 4259-4266.

(Continued)

*Primary Examiner*—Ethan Whisenant
(74) *Attorney, Agent, or Firm*—Lin Sun-Hoffman

(57) ABSTRACT

Ligation-based methods and kits are disclosed for determining the degree of methylation of one or more target nucleotides. In certain embodiments, the methylation status of one or more target nucleotides is determined by generating misligation products. In certain embodiments, at least one target nucleotide is amplified prior to the ligation reaction. In certain embodiments, at least one ligation product, at least one ligation product surrogate, at least one misligation product, at least one misligation product surrogate, or combinations thereof are amplified. In certain embodiments, one or more ligation probes comprise at least one nucleotide analog, at least one Modification, at least one mismatched nucleotide, or combinations thereof.

71 Claims, 27 Drawing Sheets

OTHER PUBLICATIONS

S. Jeon et al., "A Novel ADP-Dependent DNA Ligase From *Aeropyrum pernix* K1", FEBS Letters 550, Jul. 2003, pp. 69-73.

H. Klenk et al., "The Complete Genome Sequence Of The Hyperthermophilic, Sulphate-Reducing Archaeon Archaeoglobus Fulgidus", Nature, vol. 390, Nov. 1997, pp. 364-375.

H. Klenk et al., "The Complete Genome Sequence Of The Hyperthermophilic, Sulphate-Reducing Archaeon Archaeoglobus Fulgidus", Nature, vol. 394, Jul. 2, 1998, pp. 101.

P. Laird, "The Power And The Promise Of DNA Methylation Markers", Nature Reviews, Cancer, vol. 3, Apr. 2003, pp. 253-266.

U. Landegren et al., "A Ligase-Mediated Gene Detection Technique", Science, New Series, vol. 241, No. 4869, Aug. 26, 1988, pp. 1077-1080.

J. Luo et al., "Improving The Fidelity Of *Thermus thermophilus* DNA Ligase", Nucleic Acids Research, 1996, vol. 24, No. 14, pp. 3071-3078.

I. Martin et al., "ATP-Dependent DNA Ligases", Genome Biology 2002, vol. 3(4) :Reviews, pp. 3005.1-3005.7.

M. Nakatani et al., "Substrate Recognition And Fidelity Of Strand Joining By An Archaeal DNA Ligase", Eur. J. Biochem. vol. 269, 2002, pp. 650-656, FEBS 2002.

O. Okochi et al., "Detection Of Mitochondrial DNA Alterations In The Serum Of Hepatocellular Carcinoma Patients[1]", Clinical Cancer Research, vol. 8, Sep. 2002, pp. 2875-2878.

C. Pritchard et al., "Effects Of Base Mismatches On Joining Of Short Oligodeoxynucleotides By DNA Ligases", Nucleic Acids Research, 1997, vol. 25, No. 17, pp. 3403-3407.

T. Rein et al., "Indentifying 5-Methylcytosine And Related Modifications In DNA Genomes", Nucleic Acids Research, 1998, vol. 26, No. 10, pp. 2255-2264.

S. Shuman, "Vaccinia Virus DNA Ligase: Specificity, Fidelity, And Inhibition", Biochemistry 1995, vol. 34, pp. 16138-16147.

V. Sriskanda et al., "Characterization Of An ATP-Dependent DNA Ligase From The Thermophilic Archaeon Methanobacterium Thermoautotrophicum", Nucleic Acids Research, 2000, vol. 28, No. 11, pp. 2221-2228.

V. Sriskanda et al., "Chlorella Virus DNA Ligase: Nick Recognition And Mutational Analysis", Nucleic Acids Research, 1998, vol. 26, No. 2, pp. 525-531.

V. Sriskanda et al., "Specificity And Fidelity Of Strand Joining By Chlorella Virus DNA Ligase", Nucleic Acids Research, 1998, vol. 26, No. 15, pp. 3536-3541.

J. Tong et al., "Biochemical Properties Of A High Fidelity DNA Ligase From Thermus Species AK16D", Nucleic Acids Research, 1999, vol. 27, No. 3, pp. 788-794.

J. Tong et al., "Ligation Reaction Specificities Of An $NAD^+$-Dependent DNA Ligase From The Hyperthermophile Aquifex Aeolicus", Nucleic Acids Research 2000, vol. 28, No. 6, pp. 1447-1454.

G. Weller et al., "A Family Of DNA Repair Ligases In Bacteria?", FEBS:Letters 505, 2001, pp. 340-342.

M. Zirvi et al, "Improved Fidelity Of Thermostable Ligases For Detection Of Microsatellite Repeat Sequences Using Nucleoside Analogs", Nucleic Acids Research, 1999, vol. 27, No. 24 e41, pp. i-vii.

M. Zirvi et al., "Ligase-Based Detection Of Mononucleotide Repeat Sequences", Nucleic Acids Research, 1999, vol. 27, No. 24 e40, pp. i-viii.

U.S. Appl. No. 11/119,069, filed Apr. 29, 2005.

U.S. Appl. No. 11/118,973, filed Apr. 29, 2005.

\* cited by examiner

3'-------G-C-A-T-G----5'    Target Nucleic Acid Sequence
5'-------C-G T-A-C----3'    Probe Set 1
5'-------C-G-T-A C----3'    Probe Set 2
                    ↑ ↑
                    1 2

Figure 1

METHODS AND KITS FOR METHYLATION DETECTION

CROSS-REFERENCE TO RELATED APPLICATIONS

This application claims a priority benefit under 35 U.S.C. § 119(e) from U.S. Patent Application No. 60/567,396, filed Apr. 30, 2004, which is incorporated herein by reference.

FIELD

The present teachings generally relate to methods and kits for determining the methylation state of at least one nucleotide in nucleic acid sequences of interest. More specifically, the teachings relate to ligation-based methods and kits for determining the degree of methylation of target nucleotides.

BACKGROUND

The methylation of cytosine residues in DNA is an important epigenetic alteration in eukaryotes. In humans and other mammals methylcytosine is found almost exclusively in cytosine-guanine (CpG) dinucleotides. DNA methylation plays an important role in gene regulation and changes in methylation patterns are reportedly involved in human cancers and certain human diseases. Among the earliest and most common genetic alterations observed in human malignancies is the aberrant methylation of CpG islands, causing the over-expression or silencing of many genes. Subsequently, there is great interest in using DNA methylation markers as diagnostic indicators for early detection, risk assessment, therapeutic evaluation, recurrence monitoring, and the like. (See generally, Laird, Nature Reviews, 3:253-266, 2003; Fraga et al., BioTechniques 33:632-49, 2002; Adorjan et al., Nucleic Acids Res. 30(5):e21, 2002; and Colella et al., BioTechniques, 35(1):146-150, 2003). There is also great scientific interest in DNA methylation for studying and modifying gene regulation, among other things.

SUMMARY

Methods and kits are provided for determining the degree of methylation of specific target nucleotides, generally but not exclusively cytosine residues, in target nucleic acid sequences, typically genomic DNA (gDNA). The methods and kits generally employ at least one probe set comprising at least one first probe and at least one second probe that, under appropriate conditions, are ligated together using at least one ligation agent, to form at least one (mis)ligation product. By detecting at least some of these ligation products or their surrogates (e.g., digested ligation products, amplified ligation products, digested amplified ligation products, reporter probes or at least portions of reporter probes, and the like), one can determine the degree of methylation for the corresponding target nucleotide(s).

In certain embodiments, the presence of a methyl group on at least one target nucleotide affects the ability of at least one ligation agent to generate one or more ligation product species. By comparing the experimentally determined ligation rate for a given ligation agent and one or more probe sets with the control ligation rates (typically using the same probe set with control target nucleic acid sequences of known methylation status and the same ligation agent), the degree of methylation of at least one target nucleotide species can be determined. In certain embodiments, the presence of a methyl group on at least one target nucleotide affects the ability of at least one ligation agent to generate one or more misligation product species. That is, at least one nucleotide in the target-specific portion of at least one probe in a probe set is not fully complementary with the corresponding binding region of the target nucleic acid sequence, for example but not limited to the target nucleotide, yet the two corresponding probes are nevertheless joined, i.e., misligated by a ligation agent. By comparing the experimental misligation rate with the control misligation rates or appropriate standard curves, the degree of methylation of at least one target nucleotide can be determined. Control ligation/misligation rates can be pre-determined, analyzed in one or more parallel reaction, or determined subsequently. In certain embodiments, ligation and/or misligation occurs when the target nucleotide is not methylated but does not occur or occurs at a lower rate than when the target nucleotide is methylated. In certain embodiments, ligation/misligation is enhanced when the target nucleotide is methylated relative to the ligation/misligation rate when the target nucleotide is not methylated.

In certain embodiments, the (mis)ligation rate is affected by the presence of one or more Modifications in at least one probe of at least one probe set. In certain embodiments, the 3'-end of the hybridized upstream probe, the 5'-end of the hybridized downstream probe, or both (i.e., the ligation site), is directly opposite one or more target nucleotide. In certain embodiments, at least one ligation site is upstream from or downstream from one or more target nucleotide being interrogated. In certain embodiments, at least two probe sets for interrogating the same target nucleotide have different ligation sites. These at least two probe sets may, but need not be, competed against each other in an assay.

In certain embodiments, (mis)ligation products are amplified using at least one polymerase to generate amplified (mis)ligation products. In certain embodiments, at least one amplified (mis)ligation product or other (mis)ligation product surrogate is amplified using an amplifying means such as at least one polymerase. In certain embodiments, at least one (mis)ligation product, at least one amplified (mis)ligation product, or at least one (mis)ligation product and at least one amplified (mis)ligation product, is combined with at least one digestion means, such as an enzyme (including but not limited to at least one endonuclease, at least one exonuclease, at least one restriction enzyme, or combinations thereof) or chemical digesting means, to generate at least one digested (mis)ligation product, at least one digested amplified (mis)ligation product, or at least one digested (mis)ligation product and at least one digested amplified (mis)ligation product. At least one (mis)ligation product, at least one (mis)ligation product surrogate, or combinations thereof, are detected and the degree of methylation of the corresponding target nucleotides are determined. In certain embodiments, at least one (mis)ligation product, at least one (mis)ligation product surrogate, or combinations thereof, comprises at least one reporter group, at least one mobility modifier, at least one hybridization tag, at least one reporter probe-binding portion, at least one affinity tag, or combinations thereof that, among other things, facilitate determining the degree of target nucleotide methylation. Competitive ligation reactions, wherein at least two competing ligation probes compete with each other to hybridize with the same or substantially the same target nucleic acid sequence comprising at least one target nucleotide are within the scope of the teachings herein. In certain embodiments, determining the degree of methylation of at least one target nucleotide comprises comparing the ratio of (mis)ligation products, (mis)ligation product surrogates, or combinations thereof, for example but not limited to visual, automated, or semi-automated comparison of peak heights, peak areas, signal intensity, and the like. In certain embodiments, determining comprises using one or more computer algorithm.

Pretreatment of the target nucleic acid sequences with sodium bisulfite or other chemical modifying agent is not required (and generally not preferred), nor is enzymatic cleavage with methylation sensitive restriction endonuclease pairs, such as the isoschisomers HpaII/MspI, EcoRII/BstNI, or the like (see REBASE database at "rebase.neb.com" on the world wide web for additional information on the methylation sensitivity of specific restriction endonucleases; see also, Roberts et al., Nucleic Acids Res. 29:268-69, 2001). Thus, while the disclosed methods and kits have been designed to work with unmodified gDNA, those in the art will appreciate, that in certain instances the disclosed methods and kits can be used with such pretreated nucleic acid sequences although pretreatment is not necessary and generally is not useful in implementing the teaching herein.

In certain embodiments, methods for determining the degree of target nucleotide methylation are disclosed comprising at least one step for interrogating at least one target nucleotide; at least one step for generating at least one (mis)ligation product; and at least one step for determining the degree of methylation of at least one target nucleotide. In certain embodiments, such methods further comprise at least one step for generating at least one amplified (mis)ligation product; at least one step for generating at least one digested (mis)ligation product; or combinations thereof. Those skilled in the art will appreciate that the at least one step for interrogating can be performed using the probes and probe sets disclosed herein; that the at least one step for generating at least one (mis)ligation product can be performed using the ligation means and/or ligation techniques disclosed herein; that the at least one step for generating at least one amplified (mis)ligation product can be performed using the amplification means, amplification techniques, ligation means, and/or ligation techniques disclosed herein, including combinations thereof; that the at least one step for generating at least one digested (mis)ligation product can be performed using the digesting means and/or digestion techniques disclosed herein; and that the at least one step for determining the degree of methylation of at least one target nucleotide can be performed using the determining means and techniques disclosed herein. In certain embodiments, determining can, but need not, comprise substeps for separating, detecting, and/or analyzing/comparing. In certain embodiments, the separating is performed independently, i.e., is not a substep of the determining. Certain of the disclosed methods and kits comprise at least two separating steps and can, but need not, include at least two separating technique.

Kits for determining the degree of methylation of at least one target nucleotide are also provided. Kits serve to expedite the performance of the disclosed methods by assembling two or more components required for carrying out the methods. Kits generally contain components in pre-measured unit amounts to minimize the need for measurements by end-users. Kits preferably include instructions for performing one or more of the disclosed methods. Typically, the kit components are optimized to operate in conjunction with one another.

In certain embodiments, kits comprise at least one probe, at least one probe set, at least one primer, at least one hybridization tag, at least one hybridization tag complement, at least one mobility modifier, at least one reporter probe, at least one affinity tag, or combinations thereof. In certain embodiments, kits comprise at least one ligation agent, at least one polymerase, at least one nuclease, at least one restriction enzyme, at least one chemical digestion means, at least one nucleotide, at least one substrate, at least one of reporter group, or combinations thereof. In certain embodiments, kits are disclosed that comprise at least one means for ligating, at least one means for amplifying, at least one means for separating, at least one means for digesting, at least one detection means, or combinations thereof.

Certain embodiments of the disclosed methods and kits comprise at least one ligation agent. In certain embodiments, the ligation agent comprises at least one ligase, such as DNA ligase or RNA ligase, including, without limitation, the bacteriophage T4 (T4) DNA ligase, T4 RNA ligase, *E. coli* DNA ligase, or *E. coli* RNA ligase. In certain embodiments at least one ligase comprises at least one thermostable ligase. Exemplary thermostable ligases include without limitation, *Thermus* species ligases, Pfu ligase, Afu ligase, and the like, including ligases of bacteriophages that infect thermophilic or hyperthermophilic eubacteria and viruses that infect archaea, formerly known as archaebacteria. For a description of Afu ligase, see co-filed U.S. Provisional Patent Application Ser. No. 60/567,120, filed Apr. 30, 2004, for "Compositions, Methods, and Kits for (Mis)ligating Oligonucleotides, by Karger et al. and co-filed U.S. Patent Provisional Application Ser. No. 60/567,068, filed Apr. 30, 2004, for "Methods and Kits for Identifying Target Nucleotides in Mixed Populations," by Karger et al.

In certain embodiments, ligation is performed non-enzymatically. While not limiting, non-enzymatic ligation typically includes both photoligation and chemical ligation, such as, autoligation and ligation in the presence of an "activating" and/or reducing agent. Non-enzymatic ligation can utilize specific reactive groups on the respective 3' and 5' ends of the probes to be ligated. Thus, in certain embodiments of the disclosed methods and kits, the ligation agent comprises one or more "activating" or reducing agent. In certain embodiments, the at least one ligation agent comprises at least one photoligation source. In certain embodiments, one or more probes suitable for ligation are provided that comprise appropriate reactive groups for non-enzymatic ligation. Thus, the disclosed ligation means comprise a wide range of enzymatic, chemical and photochemical techniques and reagents for joining the ends of suitable probes.

In certain embodiments the disclosed methods and kits further comprise at least one amplifying means, for example at least one polymerase, including, but not limited to at least one DNA polymerase, at least one RNA polymerase, at least one reverse transcriptase, or combinations thereof. Such polymerases provide a means for amplifying at least one nucleotide. Exemplary polymerases include DNA polymerase I, T4 DNA polymerase, SP6 RNA polymerase, T3 RNA polymerase, T7 RNA polymerase, AMV reverse transcriptase, M-MLV reverse transcriptase, and the like. In certain embodiments, at least one DNA polymerase lacks 5'->3' exonuclease activity, for example, but not limited to Klenow fragment of DNA polymerase, 9°N$_m$™ DNA polymerase, Vent$_R$® (exo$^-$) DNA polymerase, Deep Vent$_R$® (exo$^-$) DNA polymerase, Therminator™ DNA polymerase, and the like. In certain embodiments, at least one polymerase is thermostable. Exemplary thermostable polymerases include Taq polymerase, Tfl polymerase, Tth polymerase, Tli polymerase, Pfu polymerase, AmpliTaq Gold® polymerase, 9°N$_m$™ DNA polymerase, Vent$_R$® DNA polymerase, Deep Vent$_R$® DNA polymerase, UlTma polymerase, and the like.

In certain embodiments, the disclosed methods and kits comprise at least one digestion means, for example but not limited to enzymatic and chemical means for digesting at least part of at least one probe, at least part of at least one (mis)ligation product, at least part of at least one amplified (mis)ligation product, or combinations thereof. Exemplary enzymatic means for performing a digestion step include without limitation nucleases, for example but not limited to, endonucleases and exonucleases, such as BAL-31 nuclease, mung bean nuclease, exonuclease 1, exonuclease III, A exonuclease, T7 exonuclease, exonuclease T, recJ, and RNase H; restriction enzymes; and the like, including enzymatically active variants or mutants thereof. An alkaline hydrolysis step for digesting the RNA portion of at least one RNA-DNA hybrid or RNA:DNA duplex is one example of chemical digestion means.

The skilled artisan will understand that any of a number of nucleases, polymerases, and ligases could be used in the methods and kits of the invention, including without limitation, those isolated from thermostable or hyperthermostable prokaryotic, eukaryotic, or archael organisms. The skilled artisan will also understand the terms "ligase", "nuclease" and "polymerase" include not only naturally occurring enzymes, but also recombinant enzymes; and enzymatically active fragments, cleavage products, mutants, or variants of such enzymes, for example but not limited to Klenow fragment, Stoffel fragment, Taq FS (Applied Biosystems, Foster City, Calif.), 9°N$_m$™ DNA Polymerase (New England BioLabs, Beverly, Mass.), and mutant enzymes described in Luo and Barany, Nucl. Acids Res. 24:3079-3085 (1996), and U.S. Pat. Nos. 6,265,193 and 6,576,453. Reversibly modified nucleases, ligases, and polymerases, for example but not limited to those described in U.S. Pat. No. 5,773,258, are also within the scope of the disclosed teachings. Those in the art will understand that any protein with the desired enzymatic activity, be it ligating, amplifying, or digesting, can be used in the disclosed methods and kits. Descriptions of nucleases, ligases, and polymerases can be found in, among other places, Twyman, Advanced Molecular Biology, BIOS Scientific Publishers (1999); Enzyme Resource Guide, rev. 092298, Promega (1998); Sambrook and Russell, Molecular Cloning, A Laboratory Manual, Cold Spring Harbor Press, 3d ed. (2001) (hereinafter "Sambrook and Russell"); Sambrook, Fritsch, and Maniatis, Molecular Cloning, A Laboratory Manual, Cold Spring Harbor Press, 2d ed. (1989)(hereinafter "Sambrook et al."); Ausbel et al., Current Protocols in Molecular Biology, John Wiley & Sons, Inc. (including supplements through the March 2004)(hereinafter "Ausbel et al.").

In certain embodiments, the methods and kits disclosed herein comprise at least one polymerase, at least one ligation agent, at least one digestion agent, or combinations thereof. In certain embodiments, the methods disclosed herein comprise ligation reactions and can further comprise primer extension, including but not limited to "gap filling" reactions and the polymerase chain reaction (PCR); transcription, including but not limited to reverse transcription; digestion reactions, including enzymatic or chemical digesting agents; or combinations thereof.

BRIEF DESCRIPTION OF THE DRAWINGS

FIG. 1: Schematically depicts an illustrative competing ligation reaction comprising two probe sets. The target nucleotide (in this example the nucleotide "C") in the target nucleic acid sequence is underlined (top line). Probe set 1 comprises an upstream probe with a 3'-end comprising the nucleotides -C-G and a downstream probe comprising a 5'-end comprising the nucleotides T-A-C- (middle line). The ligation site for probe set 1 is between G and T, as shown by arrow 1. Probe set 2 comprises an upstream probe with a 3'-end comprising the nucleotides -C-G-T-A and a downstream probe with a 5'-end comprising the nucleotide C- (bottom line). The ligation site for probe set 2 is between the A and the second C (left to right), as shown by arrow 2.

FIG. 12A depicts the results obtained using Afu ligase; FIG. 12B depicts the results obtained using *Thermus* sp. AK16D ligase; FIG. 12C depicts the results obtained using Tth ligase; and FIG. 12D depicts the results obtained using Taq ligase.

DESCRIPTION OF EXEMPLARY EMBODIMENTS

Figure 2:
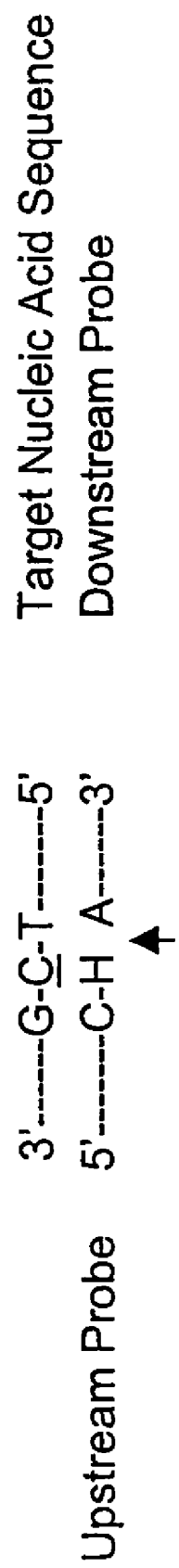
FIG. 2: Schematically depicts an exemplary misligation reaction comprising an upstream probe with a 3'-end comprising -C-H and a downstream probe with a 5'-end comprising A-. The ligation site is shown with an arrow and the target nucleotide is underlined. H represents any of A, C, T, or U, including but not limited to analogs and Modifications thereof; but not G.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. In the event that one or more of the incorporated literature and similar materials conflicts with or contradicts this application, including but not limited to defined terms, term usage, described techniques, or the like, this application controls.

I. Definitions

The term "affinity tag" as used herein refers to at least one component of a multi-component complex, wherein the components of the multi-component complex specifically interact with or bind to each other, for example but not limited to a capture moiety and its corresponding capture ligand. Exemplary multiple-component complexes include without limitation, ligands and their receptors, including but not limited to, avidin-biotin, streptavidin-biotin, and derivatives of biotin, streptavidin and/or avidin, including but not limited to desthiobiotin, NeutrAvidin (Molecular Probes, Eugene, Oreg.), CaptAvidin (Molecular Probes), and the like; binding proteins/peptides, including but not limited to maltose-maltose binding protein (MBP), calcium-calcium binding protein/peptide (CBP); antigen-antibody, including but not limited to epitope tags, including but not limited to c-MYC (e.g., EQKLISEEDL), HA (e.g., YPYDVPDYA), VSV-G (e.g., YTDIEMNRLGK), HSV (e.g., QPELAPEDPED), V5 (e.g., GKPIPNPLLGLDST), and FLAG Tag™ (e.g., DYKDDDDKG), and their corresponding anti-epitope antibodies; happens, for example but not limited to dinitrophenyl and digoxigenin, and their corresponding antibodies; aptamers and their corresponding targets; poly-His tags (e.g., penta-His and hexa-His) and their binding partners, including without limitation, corresponding immobilized metal ion affinity chromatography (IMAC) materials and anti-poly-His antibodies; fluorophores and anti-fluorophore antibodies; and the like. In certain embodiments, affinity tags are used as at least part of a means for separating, as at least part of a means for detecting, or as at least part of: a means for separating and as a means for detecting.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A:T, A:U and G:C, by Watson/Crick and Hoogsteen-type hydrogen bonding. In certain embodiments, base-stacking and hydrophobic interactions may also contribute to duplex stability. Conditions for hybridizing nucleic acid probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the probes and the complementary target sequences, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by persons of ordinary skill in the art, without undue experimentation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, BAC, ACB, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "corresponding" as used herein refers to at least one specific relationship between the elements to which the term refers. For example, at least one first probe of a particular probe set corresponds to at least one second probe of the same probe set, and vice versa. At least one primer is designed to anneal with the primer-binding portion of at least one corresponding probe, at least one corresponding (mis)ligation product, at least one corresponding amplified (mis)ligation product, at least one corresponding digested (mis)ligation product, at least one corresponding digested amplified (mis)ligation product, or combinations thereof. The target-specific portions of the probes of a particular probe set are designed to hybridize with a complementary or substantially complementary region of the corresponding target nucleic acid sequence. A particular affinity tag binds to the corresponding affinity tag, for example but not limited to, biotin binding to streptavidin. A particular hybridization tag anneals with its corresponding hybridization tag complement; and so forth.

The term "enzymatically active mutants or variants thereof" when used in reference to one or more enzyme, such as one or more polymerase, one or more ligase, one or more nuclease, or the like, refers to one or more polypeptide derived from the corresponding enzyme that retains at least some of the desired enzymatic activity, such as ligating, amplifying, or digesting, as appropriate. Also within the scope of this term are: enzymatically active fragments, including but not limited to, cleavage products, for example but not limited to Klenow fragment, Stoffel fragment, or recombinantly expressed fragments and/or polypeptides that are smaller in size than the corresponding enzyme; mutant forms of the corresponding enzyme, including but not limited to, naturally-occurring mutants, such as those that vary from the "wild-type" or consensus amino acid sequence, mutants that are generated using physical and/or chemical mutagens, and genetically engineered mutants, for example but not limited to random and site-directed mutagenesis techniques; amino acid insertions and deletions, and changes due to nucleic acid nonsense mutations, missense mutations, and frameshift mutations (see, e.g., Sriskanda and Shuman, Nucl. Acids Res. 26(2):525-31, 1998; Odell et al., Nucl. Acids Res. 31(17):5090-5100, 2003); reversibly modified nucleases, ligases, and polymerases, for example but not limited to those described in U.S. Pat. No. 5,773,258; biologically active polypeptides obtained from gene shuffling techniques (see, e.g., U.S. Pat. Nos. 6,319,714 and 6,159,688), splice variants, both naturally occurring and genetically engineered, provided that they are derived, at least in part, from one or more corresponding enzymes; polypeptides corresponding at least in part to one or more such enzymes that comprise modifications to one or more amino acids of the native sequence, including without limitation, adding, removing or altering glycosylation, disulfide bonds, hydroxyl side chains, and phosphate side chains, or crosslinking, provided such modified polypeptides retain at least some of the desired catalytic activity; and the like.

The skilled artisan will readily be able to measure enzymatic activity using an appropriate assay known in the art. Thus, an appropriate assay for polymerase catalytic activity might include, for example, measuring the ability of a variant to incorporate, under appropriate conditions, rNTPs or dNTPs into a nascent polynucleotide strand in a template-dependent manner. Likewise, an appropriate assay for ligase catalytic activity might include, for example, the ability to ligate adjacently hybridized oligonucleotides comprising appropriate reactive groups, such as disclosed herein. Protocols for such assays may be found, among other places, in Sambrook et al., Sambrook and Russell, Ausbel et al., and Housby and Southern, Nucl. Acids Res. 26:4259-66, 1998).

The terms "fluorophore" and "fluorescent reporter group" are intended to include any compound, label, or moiety that absorbs energy, typically from an illumination source or energy transfer, to reach an electronically excited state, and then emits energy, typically at a characteristic wavelength, to achieve a lower energy state. For example but without limitation, when certain fluorophores are illuminated by an energy source with an appropriate excitation wavelength, typically an incandescent or laser light source, photons in the fluorophore are emitted at a characteristic fluorescent emission wavelength. Fluorophores, sometimes referred to as fluorescent dyes, may typically be divided into families, such as fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor 488, Alexa Fluor 532, Alexa Fluor 546, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™), LIZ™, VIC™, NED™, PET™, SYBR, PicoGreen, RiboGreen, and the like. Descriptions of fluorophores and their use, can be found in, among other places, R. Haugland, Handbook of Fluorescent Probes and Research Products, $9^{th}$ ed. (2002), Molecular Probes, Eugene, Oreg. (hereinafter "Molecular Probes Handbook"); M. Schena, Microarray Analysis (2003), John Wiley & Sons, Hoboken, N.J.; Synthetic Medicinal Chemistry 2003/2004 Catalog, Berry and Associates, Ann Arbor, Mich.; U.S. Pat. No. 6,025,505; G. Hermanson, Bioconjugate Techniques, Academic Press (1996; hereinafter "Bioconjugate Techniques"); and Glen Research 2002 Catalog, Sterling, Va. Near-infrared dyes are expressly within the scope of the terms fluorophore and fluorescent reporter group, as are combination labels, such as combinatorial fluorescence energy transfer tags (see, e.g. Tong et al., Nat. Biotech. 19:756-59, 2001).

The terms "groove binder" and "minor groove binder" refer to small molecules that fit into the minor groove of double-stranded DNA, typically in a sequence specific manner. Generally, minor groove binders are long, flat molecules that can adopt a crescent-like shape and thus, snugly fit into the minor groove of a double helix, often displacing water. Minor groove binding molecules typically comprise several aromatic rings connected by bonds with torsional freedom, such as but not limited to, furan, benzene, or pyrrole rings. Exemplary minor groove binders include without limitation, antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues. In certain embodiments, at least one probe, at least one primer, at least one reporter probe, or combinations thereof, comprises at least one minor groove binder. Detailed descriptions of minor groove binders can be found in, among other places, Nucleic Acids in Chemistry and Biology, 2d ed., Blackburn and Gait, eds., Oxford University Press, 1996 (hereinafter "Blackburn and Gait"), particularly in section 8.3; Kumar et al., Nucl. Acids Res. 26:831-38, 1998; Kutyavin et al., Nucl. Acids Res. 28:655-61, 2000; Turner and Denny, Curr. Drug Targets 1:1-14, 2000; Kutyavin et al., Nucl. Acids Res. 25:3718-25, 1997; Lukhtanov et al., Bioconjug. Chem. 7:564-7, 1996; Lukhtanov et al., Bioconjug. Chem. 6: 418-26, 1995; U.S. Pat. No. 6,426,408; and PCT Published Application No. WO 03/078450. Primers and reporter probes comprising minor groove binders are commercially available from, among other places, Applied Biosystems and Epoch Biosciences, Bothell, Wash.

The term "hybridization tag" as used herein refers to an oligonucleotide sequence that can be used for separating the element (e.g., (mis)ligation products, (mis)ligation product surrogates, ZipChutes™, etc.) of which it is a component or to which it is bound, including without limitation, bulk separation; for tethering or attaching the element to which it is bound to a substrate, which may or may not include separating; for annealing a hybridization tag complement that may comprise at least one moiety, such as a mobility modifier, one or more reporter groups, and the like; or combinations thereof. In certain embodiments, the same hybridization tag is used with a multiplicity of different elements to effect: bulk separation, substrate attachment, or combinations thereof. A "hybridization tag complement" typically refers to at least one oligonucleotide that comprises at least one sequence of nucleotides that are at least substantially complementary to and hybridize with the corresponding hybridization tag. In various embodiments, hybridization tag complements serve as capture moieties for attaching at least one hybridization tag:element complex to at least one substrate; serve as "pull-out" sequences for bulk separation procedures; or both as capture moieties and as pull-out sequences. In certain embodiments, at least one hybridization tag complement comprises at least one reporter group and serves as a label for at least one (mis) ligation product, at least one (mis)ligation product surrogate, or combinations thereof. In certain embodiments, determining comprises detecting one or more reporter groups on or attached to at least one hybridization tag complement or at least part of a hybridization tag complement.

Typically, hybridization tags and their corresponding hybridization tag complements are selected to minimize: internal self-hybridization; cross-hybridization with different hybridization tag species, nucleotide sequences in a reaction composition, including but not limited to gDNA, different species of hybridization tag complements, target-specific portions of probes, and the like; but should be amenable to facile hybridization between the hybridization tag and its corresponding hybridization tag complement. Hybridization tag sequences and hybridization tag complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of hybridization tags can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein); and Gerry et al., J. Mol. Biol. 292:251-262 (1999; referred to as "zip-codes" and "zip-code complements" therein). Those in the art will appreciate that a hybridization tag and its corresponding hybridization tag complement are, by definition, complementary to each other and thus the terms hybridization tag and hybridization tag complement are relative and can typically be used interchangeably in most contexts.

Hybridization tags can be located on at least one end of at least one probe, at least one primer, at least one (mis)ligation product, at least one (mis)ligation product surrogate, or combinations thereof; or they can be located internally. In certain embodiments, at least one hybridization tag is attached to at least one probe, at least one primer, at least one (mis)ligation product, at least one (mis)ligation product surrogate, or combinations thereof, via at least one linker arm. In certain embodiments, at least one linker arm is cleavable.

In certain embodiments, hybridization tags are at least 12 bases in length, at least 15 bases in length, 12-60 bases in length, or 15-30 bases in length. In certain embodiments, at least one hybridization tag is 12, 15, 20, 21, 22, 23, 24, 25, 26, 27, 28, 29, 30, 45, or 60 bases in length. In certain embodiments, at least two hybridization tag:hybridization tag complement duplexes have melting temperatures that fall within a $\Delta T_m$ range ($T_{max}-T_{min}$) of no more than 10° C. of each other. In certain embodiments, at least two hybridization tag:hybridization tag complement duplexes have melting temperatures that fall within a $\Delta T_m$ range of 5° C. or less of each other.

In certain embodiments, at least one hybridization tag complement comprises at least one reporter group, at least one mobility modifier, at least one reporter probe-binding portion, or combinations thereof. In certain embodiments, at least one hybridization tag complement is annealed to at least one corresponding hybridization tag and, subsequently, at least part of that hybridization tag complement is released and detected.

The term "ligation product" refers to a molecule that is generated when an internucleotide linkage is formed between two corresponding probes by the action of one or more ligation agents. Those in the art understand that, under certain conditions, such an internucleotide linkage can be formed between: (i) at least one pair of matched probes (i.e., the target-specific portions of both probes are fully complementary with the corresponding sequences of the target), or (ii) at least one pair of mismatched probes (that is at least one of the two probes comprises at least one nucleotide or nucleotide analog that is mismatched with the corresponding template or at least one Modification). Thus, the term (mis)ligation is used herein to collectively refer to at least one match ligation, at least one mismatch ligation (sometimes referred to as misligation), or at least one match ligation and at least one misligation. Hence, by way of illustration but without limitation, at least one "(mis)ligation product" refers to at least one ligation product, at least one misligation product, or at least one ligation product and at least one misligation product; at least one "(mis)ligation product surrogate" refers to at least one ligation product surrogate, at least one misligation product surrogate, or at least one ligation product surrogate and at least one misligation product surrogate; and so forth. The term "misligation" is generally intended to refer to products, surrogates, and the like that result from mismatch ligation reaction, but not match ligation reactions.

The term "ligation product surrogate" as used herein refers to any molecule or moiety whose detection or identification indicates the existence of one or more corresponding ligation products. Exemplary ligation product surrogates include but are not limited to, digested ligation products; amplified ligation products; digested amplified ligation products; one or more moieties cleaved or released from a ligation product or ligation product surrogate; one or more complementary strand or counterpart of a ligation product or ligation product surrogate; reporter probes, including but not limited to cleavage and amplification products thereof; hybridization tag complements, including but not limited to ZipChutes™ (typically a molecule or complex comprising at least one hybridization tag complement, at least one mobility modifier, and at least one reporter group, generally a fluorescent reporter group; see, e.g., Applied Biosystems Part Number 4344467 Rev. C; see also U.S. Provisional Patent Application Ser. No. 60/517,470); and the like. The term "digested amplified ligation product" is intended to include a ligation product that is digested then amplified as well as a ligation product that is amplified then digested.

As used herein, "ligation rate" or "rate" are relative terms that are determined by evaluating at least one measurable parameter of at least one (mis)ligation product or its surrogate. In certain embodiments, a "ligation rate ratio" or "ratio" is obtained by comparing at least one quantifiable parameter of at least one first (mis)ligation product with the same measurable parameter of at least one second (mis)ligation product generated under the same conditions. By way of illustration, without limitation, if the integrated area under the curve corresponding to exemplary (mis)ligation product A is 10 and the integrated area under the curve corresponding to exemplary (mis)ligation product B generated under the same conditions is 1, the corresponding ligation rate ratio is 10:1 (A/B) or 1:10 (B/A). In certain embodiments, the ligation rate for a given ligation product is compared to at least one corresponding standard curve. Those in the art appreciate that numerous measurable parameters exist that can be used to compare the amounts of two or more (mis)ligation products generated under the same conditions, including without limitation, (mis)ligation product peak height, integrated area under the curve for the (mis)ligation products, and so forth. By evaluating the ligation rate or the ligation rate ratio, one can determine the degree of methylation for at least one target nucleotide.

The term "mobility-dependent analytical technique" as used herein refers to any means for separating different molecular species based on differential rates of migration of those different molecular species in one or more separation techniques. Exemplary mobility-dependent analysis techniques include electrophoresis, chromatography, mass spectroscopy, sedimentation, e.g., gradient centrifugation, field-flow fractionation, multi-stage extraction techniques and the like. Descriptions of mobility-dependent analytical techniques can be found in, among other places, U.S. Pat. Nos. 5,470,705, 5,514,543, 5,580,732, 5,624,800, and 5,807,682; PCT Publication No. WO 01/92579; D. R. Baker, Capillary Electrophoresis, Wiley-Interscience (1995); Biochromatography: Theory and Practice, M. A. Vijayalakshmi, ed., Taylor & Francis, London, U.K. (2003); Krylov and Dovichi, Anal. Chem. 72:111 R-128R (2000); Swinney and Bornhop, Electrophoresis 21:1239-50 (2000); Crabtree et al., Electrophoresis 21:1329-35 (2000); and A. Pingoud et al., Biochemical Methods: A Concise Guide for Students and Researchers, Wiley-VCH Verlag GmbH, Weinheim, Germany (2002).

The term "mobility modifier" as used herein refers to at least one molecular entity, for example but not limited to, at least one polymer chain, that when added to at least one element (e.g., at least one probe, at least one primer, at least one (mis)ligation product, at least one (mis)ligation product surrogate, or combinations thereof affects the mobility of the element to which it is hybridized or bound, covalently or non-covalently, in at least one mobility-dependent analytical technique. Typically, a mobility modifier changes the charge/translational frictional drag when hybridized or bound to the element; or imparts a distinctive mobility, for example but not limited to, a distinctive elution characteristic in a chromatographic separation medium or a distinctive electrophoretic mobility in a sieving matrix or non-sieving matrix, when hybridized or bound to the corresponding element; or both (see, e.g., U.S. Pat. Nos. 5,470,705 and 5,514,543; Grossman et al., Nucl. Acids Res. 22:4527-34 (1994)). In certain embodiments, a multiplicity of probes exclusive of mobility modifiers, a multiplicity of primers exclusive of mobility modifiers, a multiplicity of (mis)ligation products exclusive of mobility modifiers, a multiplicity of (mis)ligation product surrogates exclusive of mobility modifiers, or combinations thereof, have the same or substantially the same mobility in at least one mobility-dependent analytical technique.

In certain embodiments, a multiplicity of probes, a multiplicity of primers, a multiplicity of ligation products, a multiplicity of ligation product surrogates, or combinations thereof, have substantially similar distinctive mobilities, for example but not limited to, when a multiplicity of elements comprising mobility modifiers have substantially similar distinctive mobilities so they can be bulk separated or they can be separated from other elements comprising mobility modifiers with different distinctive mobilities. In certain embodiments, a multiplicity of probes comprising mobility modifiers, a multiplicity of primers comprising mobility modifiers, a multiplicity of (mis)ligation products comprising mobility modifiers, a multiplicity of (mis)ligation product surrogates comprising mobility modifiers, or combinations thereof, have different distinctive mobilities.

In certain embodiments, at least one mobility modifier comprises at least one nucleotide polymer chain, including without limitation, at least one oligonucleotide polymer chain, at least one polynucleotide polymer chain, or both at least one oligonucleotide polymer chain and at least one polynucleotide polymer chain. For example but not limited to a series of additional non-target sequence-specific nucleotides in one or more probes such as "TTTT", shown in Table 7; or nucleotide spacers (see e.g., Tong et al., Nat. Biotech. 19:756-759 (2001)). In certain embodiments, at least one mobility modifier comprises at least one non-nucleotide polymer chain. Exemplary non-nucleotide polymer chains include, without limitation, peptides, polypeptides, polyethylene oxide (PEO), or the like. In certain embodiments, at least one polymer chain comprises at least one substantially uncharged, water-soluble chain, such as a chain composed of one or more PEO units; a polypeptide chain; or combinations thereof.

The polymer chain can comprise a homopolymer, a random copolymer, a block copolymer, or combinations thereof. Furthermore, the polymer chain can have a linear architecture, a comb architecture, a branched architecture, a dendritic architecture (e.g., polymers containing polyamidoamine branched polymers, Polysciences, Inc. Warrington, PA), or combinations thereof. In certain embodiments, at least one polymer chain is hydrophilic, or at least sufficiently hydrophilic when hybridized or bound to an element to ensure that the element-mobility modifier is readily soluble in aqueous medium. Where the mobility-dependent analytical technique is electrophoresis, in certain embodiments, the polymer chains are uncharged or have a charge/subunit density that is substantially less than that of its corresponding element.

The synthesis of polymer chains useful as mobility modifiers will depend, at least in part, on the nature of the polymer. Methods for preparing suitable polymers generally follow well-known polymer subunit synthesis methods. These methods, which involve coupling of defined-size, multi-subunit polymer units to one another, either directly or through charged or uncharged linking groups, are generally applicable to a wide variety of polymers, such as PEO, polyglycolic acid, polylactic acid, polyurethane polymers, polypeptides, oligosaccharides, and nucleotide polymers. Such methods of polymer unit coupling are also suitable for synthesizing selected-length copolymers, e.g., copolymers of PEO units alternating with polypropylene units. Polypeptides of selected lengths and amino acid composition, either homopolymer or mixed polymer, can be synthesized by standard solid-phase methods (see, e.g., Int. J. Peptide Protein Res., 35: 161-214 (1990)).

One method for preparing PEO polymer chains having a selected number of hexaethylene oxide (HEO) units, an HEO unit is protected at one end with dimethoxytrityl (DMT), and activated at its other end with methane sulfonate. The activated HEO is then reacted with a second DMT-protected HEO group to form a DMT-protected HEO dimer. This unit-addition is then carried out successively until a desired PEO chain length is achieved (see, e.g., U.S. Pat. No. 4,914,210; see also, U.S. Pat. No. 5,777,096).

As used herein, the term "Modification" refers to at least one substituted hydrocarbon, at least one ribonucleotide, at least one amide bond (including but not limited to at least one PNA, at least one pcPNA, or both), at least one nucleotide analog, at least one groove binder, or combinations thereof. In certain embodiments, at least one probe comprises at least one Modification, sometimes referred to as a "Modified probe." In certain embodiments, at least one Modification comprises at least one structure shown below,

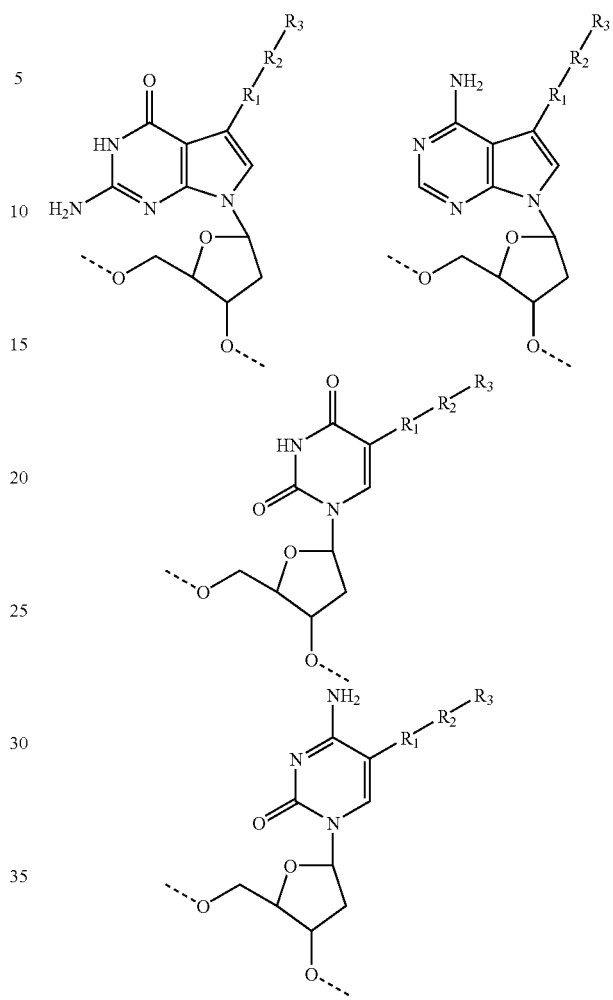

wherein: (a) $R_1$ comprises at least one hydrogen, alkyl, substituted alkyl, alkene, substituted alkene, alkyne, substituted alkyne, aromatic ring, substituted aromatic ring, heteroaromatic ring, substituted heteroaromatic ring, halogen, nitro, cyano, oxygen, substituted oxygen, nitrogen, substituted nitrogen, divalent sulfur, substituted divalent sulfur, sulfonate, sulfonate ester, aldehyde, ketone carbon with $R_2$, carboxylate carbon as carboxylic acid and ester with $R_2$, or combinations thereof; (b) $R_2$, a substituent on $R_1$, comprises at least one hydrogen, alkyl, substituted alkyl, alkene, substituted alkene, alkyne, substituted alkyne, aromatic ring, substituted aromatic ring, heteroaromatic ring, substituted heteroaromatic ring, halogen, nitro, cyano, alcohol, ether substituted with $R_3$, amine, secondary, tertiary, and quaternary amines substituted with $R_3$, amido substituted with $R_3$, thiol, thioether substituted with $R_3$, sulfonate, sulfonate ester substituted with $R_3$, phosphate and phosphate esters substituted with $R_3$, phosphonate and phosphonate esters substituted with $R_3$, aldehyde, ketone substituted with $R_3$, carboxylate, carboxylate esters substituted with $R_3$, carboxyamides substituted with $R_3$, or combinations thereof; and (c) $R_3$, a substituent on $R_2$, comprises at least one hydrogen, alkyl, substituted alkyl, alkene, substituted alkene, alkyne, substituted alkyne, aromatic ring, substituted aromatic ring, heteroaromatic ring, substituted heteroaromatic ring, halogen, nitro, cyano, alcohol, ether as defined in R₂, amine, secondary, tertiary, and quaternary amines as defined in R₂, amido as defined in R₂, thiol, thioether as defined in R₂, sulfonate, sulfonate ester as defined in R₂, phosphate and phosphate esters as defined in R₂, phosphonate and phosphonate esters as defined in R₂, aldehyde, ketone as defined in R₂, carboxylate, carboxylate esters as defined in R₂, carboxyamides as defined in R₂.

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen-type hydrogen bonds with a complementary nucleotide base. Exemplary nucleotide bases and analogs thereof include, but are not limited to, naturally occurring nucleotide bases adenine, guanine, cytosine, 5 methyl-cytosine, uracil, thymine, and analogs of the naturally occurring nucleotide bases, including without limitation, 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2 ms6iA), N2dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, O⁶-methylguanine, N⁶-methyladenine, O⁴-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different, —R, —OR, —NR₂ azide, cyanide or halogen groups, where each R is independently H, C₁-C₆ alkyl, C₂-C₇ acyl, or C₅-C₁₄ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226).

Exemplary LNA sugar analogs within a polynucleotide include, but are not limited to, the structures:

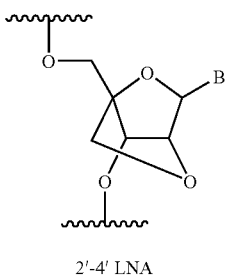 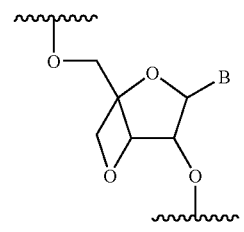

2'-4' LNA          3'-4' LNA where B is any nucleotide base.

[m]odifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, cyano, amido, imido, amino, alkylamino, fluoro, chloro and bromo. Nucleotides include, but are not limited to, the natural D optical isomer, as well as the L optical isomer forms (see, e.g., Garbesi Nucl. Acids Res. 21:4159-65 (1993); Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the N⁹-position of the nucleotide base. When the nucleotide base is pyrimidine, e.g. C, T, or U, the pentose sugar is attached to the N¹-position of the nucleotide base, except for pseudouridines, in which the pentose sugar is attached to the C5 position of the uracil nucleotide base (see, e.g., Kornberg and Baker, (1992) *DNA Replication*, 2ⁿᵈ Ed., Freeman, San Francisco, Calif.).

One or more of the pentose carbons of a nucleotide may be substituted with a phosphate ester having the formula:

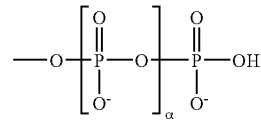

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5"-triphosphate" refers to a nucleotide with a triphosphate ester group at the 5' position, and is sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. Reviews of nucleotide chemistry can be found in, among other places, Shabarova, Z. and Bogdanov, A. Advanced Organic Chemistry of Nucleic Acids, VCH, New York, 1994; and Blackburn and Gait.

The term "nucleotide analog", as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers that can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone comprising at least one amide bond. (See, e.g., Datar and Kim, Concepts in Applied Molecular Biology, Eaton Publishing, Westborough, Mass., 2003, particularly at pages 74-75; Verma and Eckstein, Ann. Rev. Biochem. 67:99-134, 1998; Goodchild, Bioconj. Chem., 1:165-187, 1990).

As used herein, the terms "polynucleotide", "oligonucleotide", "nucleic acid", and "nucleic acid sequence" are generally used interchangeably and include single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, tetraalkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. Nucleic acids typically range in size from a few monomeric units, e.g. 5-40 when they are sometimes referred to in the art as oligonucleotides, to several thousands of monomeric nucleotide units. Nucleic acid sequence are shown in the 5' to 3' orientation from left to right, unless otherwise apparent from the context or expressly indicated differently; and in such sequences, "A" denotes deoxyadenosine, "C" denotes deoxycytidine, "G" denotes deoxyguanosine, "T" denotes thymidine, and "U" denotes uridine.

Nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

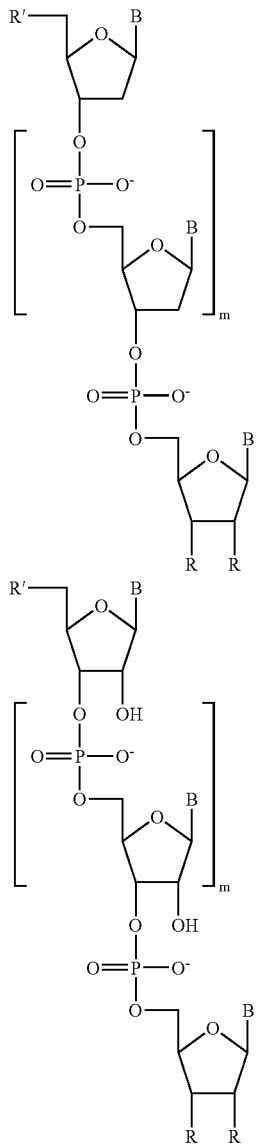

wherein each B is independently the base moiety of a nucleotide, e.g., a purine, a 7-deazapurine, a purine or purine analog substituted with one or more substituted hydrocarbons, a pyrimidine, a pyrimidine or pyrimidine analog substituted with one or more substituted hydrocarbons, or an analog nucleotide; each m defines the length of the respective nucleic acid and can range from zero to thousands, tens of thousands, or even more; each R is independently selected from the group comprising hydrogen, halogen, —R", —OR", and —NR"R", where each R" is independently (C1-C6) alkyl, (C2-C7) acyl or (C5-C14) aryl, cyanide, azide, or two adjacent Rs are taken together to form a bond such that the ribose sugar is 2',3'-didehydroribose; and each R' is independently hydroxyl or

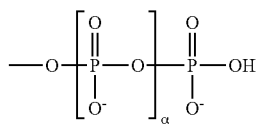

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "nucleic acid sequence", "polynucleotide", and "oligonucleotide" can also include nucleic acid analogs, polynucleotide analogs, and oligonucleotide analogs. The terms "nucleic acid analog", "polynucleotide analog" and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, *Science* 254: 1497-1500; PCT Publication No. WO 92/20702; U.S. Pat. Nos. 5,719,262 and 5,698,685); morpholinos (see, e.g., U.S. Pat. No. 5,698,685; U.S. Pat. No. 5,378,841; U.S. Pat. No. 5,185,144); carbamates (see, e.g., Stirchak & Summerton, J. Org. Chem. 52: 4202, 1987); methylene(methylimino) (see, e.g., Vasseur et al., J. Am. Chem. Soc. 114:4006, 1992); 3'-thioformacetals (see, e.g., Jones et al., 1993, *J. Org. Chem.* 58: 2983); sulfamates (see, e.g., U.S. Pat. No. 5,470, 967); 2-aminoethylglycine, commonly referred to as PNA (see, e.g., PCT Publication No. WO 92/20702; Nielsen, Science 254:1497-1500, 1991); and others (see, e.g., U.S. Pat. No. 5,817,781; Frier & Altman, Nucl. Acids Res. 25:4429, 1997 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate. See also, Scheit, Nucleotide Analogs, John Wiley, New York, (1980); Englisch, Agnew. Chem. Int. Ed. Engl. 30:613-29, 1991; Agarwal, Protocols for Polynucleotides and Analogs, Humana Press, 1994; and S. Verma and F. Eckstein, Ann. Rev. Biochem. 67:99-134, 1999.

The term "polymerase" is used in a broad sense herein and includes amplifying means such as DNA polymerases, enzymes that typically synthesize DNA by incorporating deoxyribonucleotide triphosphates or analogs in the 5'=>3' direction in a template-dependent and primer-dependent manner; RNA polymerases, enzymes that typically synthesize RNA by incorporating ribonucleotide triphosphates or analogs, generally in a template-dependent manner; and reverse transcriptases, also known as RNA-dependent DNA polymerases, that synthesize DNA by incorporating deoxyribonucleotide triphosphates or analogs in the 5'=>3' direction in primer-dependent manner, typically using an RNA template. Descriptions of polymerases can be found in, among other places, R. M. Twyman, Advanced Molecular Biology, Bios Scientific Publishers Ltd. (1999); Polymerase Enzyme Resource Guide, Promega, Madison, Wis. (1998); P. C. Turner et al., Instant Notes in Molecular Biology, Bios Scientific Publishers Ltd. (1997); and B. D. Hames et al., Instant Notes in Biochemistry, Bios Scientific Publishers Ltd. (1997).

The term "primer" as used herein refers to an oligonucleotide comprising at least one region that is complementary or substantially complementary to the primer-binding portion of at least one probe, at least one (mis)ligation product, at least one (mis)ligation product surrogate, or combinations thereof, including sequences that are complementary to any of these, and that can anneal with such primer-binding portions or their complements under appropriate conditions. Primers typically serve as initiation sites for certain amplification techniques, including but not limited to, primer extension and PCR. A primer that hybridizes with a multiplicity of different probe species, (mis)ligation product species, (mis)ligation product surrogate species, or combinations thereof, is referred to as a "universal primer". In certain embodiments, at least one primer comprises at least one additional component, including but not limited to, at least one primer-binding portion, at least one reporter probe-binding portion, at least one reporter group, at least one hybridization tag, at least one mobility modifier, at least one affinity tag, or combinations thereof.

The term "probe" as used herein, refers to an oligonucleotide comprising a target-specific portion that is capable, under appropriate conditions, of hybridizing with at least a part of at least one corresponding target nucleic acid sequence. As used herein, the terms probe and probes generally refer to ligation probes and misligation probes, including competing ligation probes and competing misligation probes, unless otherwise apparent from the context. A probe may include Watson-Crick bases or modified bases, including but not limited to, the AEGIS bases (from Eragen Biosciences), described, e.g., in U.S. Pat. Nos. 5,432,272; 5,965,364; and 6,001,983. Additionally, bases may be joined by a natural phosphodiester bond or a different chemical linkage. Different chemical linkages include, but are not limited to, at least one amide linkage or at least one Locked Nucleic Acid (LNA) linkage, described in, e.g., published PCT Applications WO 00/56748 and WO 00/66604.

Probes typically are part of at least one ligation probe set or at least one competing ligation probe set, comprising at least one first probe and at least one second probe. In certain embodiments, at least one probe comprises at least one nucleotide in its target-specific portion that is mismatched relative to at least one portion of its corresponding target nucleic acid sequence, at least one Modification, or both at least one mismatched nucleotide and at least one Modification. In certain embodiments, at least one mismatched nucleotide also comprises at least one Modification.

In certain embodiments, at least one probe comprises at least one additional component, including but not limited to, at least one primer-binding portion, at least one reporter probe-binding portion, at least one reporter group, at least one hybridization tag, at least one mobility modifier, at least one affinity tag, or combinations thereof. In certain embodiments, such additional components are within the target-specific portion, coextensive with the target-specific portion, overlaps at least part of the target-specific portion, or combinations thereof.

The target-specific portions of ligation probes are of sufficient length to permit specific annealing to complementary sequences in corresponding target nucleic acid sequences. Likewise, primers are of sufficient length to permit specific annealing to complementary sequences in corresponding (mis)ligation products, corresponding (mis) ligation product surrogates, or combinations thereof. The criteria for designing sequence-specific nucleic acid probes (including but not limited to ligation probes and reporter probes) and primers are well known to those in the art. In certain embodiments, at least one probe, at least one primer, or at least one probe and at least one primer comprises at least one region that is fully complementary with the corresponding sequences in at least one target nucleic acid sequence, at least one (mis)ligation product, at least one (mis)ligation product surrogate, or combinations thereof. In certain embodiments, at least one probe contains at least one mismatched nucleotide relative to at least one corresponding nucleotide in the target nucleic acid sequence, at least one Modification, at least one additional component, or combinations thereof. Detailed descriptions of nucleic acid probe and primer design can be found in, among other places, Diffenbach and Dveksler, PCR Primer, A Laboratory Manual, Cold Spring Harbor Press (1995); R. Rapley, The Nucleic Acid Protocols Handbook (2000), Humana Press, Totowa, N.J. (hereinafter "Rapley"); Schena; and Kwok et al., Nucl. Acid Res. 18:999-1005 (1990). Primer and probe design software programs are also commercially available, including without limitation, Primer Express, Applied Biosystems, Foster City, Calif.; Primer Premier and Beacon Designer software, PREMIER Biosoft International, Palo Alto, Calif.; Primer Designer 4, Sci-Ed Software, Durham, N.C.; Primer Detective, ClonTech, Palo Alto, Calif.; Lasergene, DNASTAR, Inc., Madison, Wis.; Oligo software, National Biosciences, Inc., Plymouth, Minn.; ioligo, Caesar Software, Portsmouth, N.H.; and RTPrimerDB on the world wide web at realtimeprimerdatabase.ht.st or at medgen31.urgent.be/primerdatabase/index (see also, Pattyn et al., Nucl. Acid Res. 31:122-23, 2003).

A "probe set" according to the present teachings comprises at least one first probe and at least one second probe that typically adjacently hybridize to the same target sequence, but not always, and are generally used for interrogating at least one target nucleotide. The first probe of each probe set is designed to hybridize with the downstream region of the target sequence in a sequence-specific manner. The second probe in the probe set is designed to hybridize with the upstream region of the target sequence in a sequence-specific manner. The use of the terms first and second with respect to probed and primers is to distinguish one from the other and is generally not intended to be limiting. The sequence-specific portions of these probes are of sufficient length to permit specific annealing with complementary sequences in targets and primers, as appropriate. In certain embodiments, both the at least one first probe and the at least one second probe in a probe set further comprise primer-specific portions suitable for hybridizing with primers.

Under appropriate conditions, adjacently hybridized probes can be ligated together by one or more ligation agents to form a ligation product, provided that they comprise appropriate reactive groups, for example, without limitation, a free 3'-hydroxyl or 5'-phosphate group. Some probe sets may comprise more than one first probe or more than one second probe or both, to aid in determining the degree of methylation at one or more target nucleotide. Certain of the disclosed methods comprise a multiplicity of different probe sets for determining a multiplicity of different target nucleotides in a multiplex ligation reaction. Certain embodiments comprise at least one multiplex amplification reaction, at least one multiplex ligation reaction, or at least one multiplex amplification reaction and at least one multiplex ligation reaction. In certain embodiments, at least one multiplex amplification reaction and at least one multiplex ligation reaction are performed in the same tube.

Those in the art understand that probes and probe sets that are suitable for use with the disclosed methods and kits can be identified empirically using the current teachings and routine methods known in the art, without undue experimentation. For example, suitable probes and probe sets can be obtained by selecting appropriate target nucleotides and target nucleotide sequences by searching relevant scientific literature, including but not limited to appropriate databases (see, e.g., DNA Methylation Database (MethDB), on the web at methdb.de or methdb.net; CpG Island Searcher, on the web at cpgislands.com; the NCBI Entrez Nucleotide database), or by experimental analysis. When target nucleic acid sequences of interest are identified, test probes can be synthesized (and Modified if desired) using well known oligonucleotide synthesis and organic chemistry techniques (see, e.g., Current Protocols in Nucleic Acid Chemistry, Beaucage et al., eds., John Wiley & Sons, New York, N.Y., including updates through April 2004 (hereinafter "Beaucage et al."); Blackburn and Gait; Glen Research 2002 Catalog, Sterling, Va.; and Synthetic Medicinal Chemistry 2003/2004, Berry and Associates, Dexter, Mich.). Test probes and/or probe sets are employed in the disclosed assays using appropriate target sequences and their suitablility for interrogating the target nucleotide is evaluated. Standard curves for determining the degree of target nucleotide methylation can then be generated, if desired, using pre-determined mixtures of methylated and non-methylated synthetic templates or gDNA as the target nucleic acid sequences in one or more of the disclosed ligation assays under standard conditions. Those in the art are familiar with generating and using standard curves (see, e.g., Overholtzer et al., Proc. Natl. Sci. 100:11547-52, 2003).

According to certain embodiments, the primer sets comprise at least one first primer and at least one second primer. The first primer of a primer set is designed to hybridize with the complement of the 5' primer-specific portion of a (mis)ligation product, appropriate (mis)ligation product surrogates, or combinations thereof, in a sequence-specific manner. The second primer in that primer set is designed to hybridize with a 3' primer-specific portion of the same (mis)ligation product, appropriate (mis)ligation product surrogates, or combinations thereof, in a sequence-specific manner. In certain embodiments, at least one primer of the primer set further comprises at least one reporter group, at least one hybridization tag, at least one affinity tag, or combinations thereof. Suitable probes and primers can be synthesized using methods well known on the art. Detailed descriptions of probe and primer synthesis and phosphorylation can be found in, among other places, Beaucage et al., Tong et al., Nucl. Acids Res. 27:788-94 (1999), Housby and Southern, Nucl. Acids Res. 26:4259-66 (1998), and Grossman et al., Nucl. Acids Res. 22:4527-34 (1994).

The term "reporter group" is used in a broad sense herein and refers to any identifiable tag, label, or moiety. The skilled artisan will appreciate that many different species of reporter groups can be used in the present teachings, either individually or in combination with one or more different reporter group. Exemplary reporter groups include, but are not limited to, fluorophores, radioisotopes, chromogens, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.5Ph.NCS," "Cy.7.0phEt.NCS," "Cy7.0phEt.CO$_2$Su", and IRD800 (see, e.g., J. Flanagan et al., Bioconjug. Chem. 8:751-56 (1997); and DNA Synthesis with IRD800 Phosphoramidite, LI-COR Bulletin #111, LI-COR, Inc., Lincoln, Nebr.), electrochemiluminescence labels, including but not limited to, tris(bipyridal) ruthenium (II), also known as Ru(bpy)$_3^{2+}$, Os(1,10-phenanthroline)$_2$bis(diphenylphosphino)ethane$^{2+}$, also known as Os(phen)$_2$(dppene)$^{2+}$, luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as Ru(v-bpy$_3^{2+}$), and the like.

The term reporter group also encompasses at least one element of multi-element indirect reporter systems, including without limitation, affinity tags such as biotin:avidin, antibody:antigen, ligand:receptor including but not limited to binding proteins and their ligands, enzyme:substrate, and the like, in which one element interacts with one or more other elements of the system in order to effect the potential for a detectable signal. Exemplary multi-element reporter systems include an oligonucleotide comprising at least one biotin reporter group and a streptavidin-conjugated fluorophore, or vice versa; an oligonucleotide comprising at least one dinitrophenyl (DNP) reporter group and a fluorophore-labeled anti-DNP antibody; and the like. In certain embodiments, reporter groups, particularly multi-element reporter groups, are not necessarily used for detection, but rather serve as affinity tags for isolation/separation, for example but not limited to, a biotin reporter group and a streptavidin coated substrate, or vice versa; a digoxygenin reporter group and an anti-digoxygenin antibody or a digoxygenin-binding aptamer; a DNP reporter group and an anti-DNP antibody or a DNP-binding aptamer; and the like. Detailed protocols for attaching reporter groups to oligonucleotides, polynucleotides, peptides, antibodies and other proteins, mono-, di- and oligosaccharides, organic molecules, and the like can be found in, among other places, Bioconjugate Techniques; Beaucage et al.; Molecular Probes Handbook; and Pierce Applications Handbook and Catalog 2003-2004, Pierce Biotechnology, Rockford, IL, 2003 (hereinafter "Pierce Applications Handbook").

In certain embodiments, at least one reporter group comprises at least one electrochemiluminescent moiety that can, under appropriate conditions, emit detectable electrogenerated chemiluminescence (ECL). In ECL, excitation of the electrochemiluminescent moiety is electrochemically driven and the chemiluminescent emission can be optically detected. Exemplary electrochemiluminescent reporter group species include: Ru(bpy)$_3^{2+}$ and Ru(v-bpy)$_3^{2+}$ with emission wavelengths of 620 nm; Os(phen)$_2$(dppene)$^{2+}$ with an emission wavelength of 584 nm; luminol/hydrogen peroxide with an emission wavelength of 425 nm; Al(hydroxyquinoline-5-sulfonic acid) with an emission wavelength of 499 nm; and 9,10-diphenylanothracene-2-sulfonate with an emission wavelength of 428 nm; and the like. Forms of these three electrochemiluminescent reporter group species that are modified to be amenable to incorporation into probes are commercially available or can be synthesized without undue experimentation using techniques known in the art. For example, a Ru(bpy)$_3^{2+}$ N-hydroxy succinimide ester for coupling to nucleic acid sequences through an amino linker group has been described (see, U.S. Pat. No. 6,048,687); and succinimide esters of Os(phen)$_2$(dppene)$^{2+}$ and Al(HQS)$_3^{3+}$ can be synthesized and attached to nucleic acid sequences using similar methods. The Ru(bpy)$_3^{2+}$ electrochemiluminescent reporter group can be synthetically incorporated into nucleic acid sequences using commercially available ru-phosphoramidite (IGEN International, Inc., Gaithersburg, Md.).

Additionally other polyaromatic compounds and chelates of ruthenium, osmium, platinum, palladium, and other transition metals have shown electrochemiluminescent properties. Detailed descriptions of ECL and electrochemiluminescent moieties can be found in, among other places, A. Bard and L. Faulkner, Electrochemical Methods, John Wiley & Sons (2001); M. Collinson and M. Wightman, Anal. Chem. 65:2576 (1993); D. Brunce and M. Richter, Anal. Chem. 74:3157 (2002); A. Knight, Trends in Anal. Chem. 18:47 (1999); B. Muegge et al., Anal. Chem. 75:1102 (2003); H. Abrunda et al., J. Amer. Chem. Soc. 104:2641(1982); K. Maness et al., J. Amer. Chem. Soc. 118:10609 (1996); M. Collinson and R. Wightman, Science 268:1883 et seq. (1995); and U.S. Pat. No. 6,479,233.

The term "reporter probe" refers to a biomolecule, typically an oligonucleotide, that binds to or anneals with at least one (mis)ligation product, at least one (mis)ligation product surrogate, or combinations thereof, and is used to determine the degree of methylation of at least one target nucleotide. Most reporter probes can be categorized based on their mode of action, for example but not limited to: nuclease probes, including without limitation TaqMan® probes and the like (see, e.g., Livak, Genetic Analysis: Biomolecular Engineering 14:143-149 (1999); Yeung et al., BioTechniques 36:266-75 (2004)); extension probes such as scorpion primers, Lux™ primers, Amplifluors, and the like; hybridization probes such as molecular beacons, Eclipse probes, and the like; or combinations thereof. Quantitative PCR methods, particularly real-time PCR methods, typically comprise at least one reporter probe, for example but not limited to, at least one nuclease probe, at least one hybridization probe, at least one extension probe, at least one probe comprising at least one amide bond, at least one probe comprising at least one PNA, at least one probe comprising at least one LNA, at least one nucleic acid dye, or combinations thereof, including stem-loop and stem-less reporter probes.

In certain embodiments, at least one reporter probe comprises at least one reporter group, at least one quenching agent, at least one affinity tag, at least one hybridization tag, at least one hybridization tag complement, or combinations thereof. In certain embodiments, at least one hybridization tag complement anneals with at least one hybridization tag, at least one member of a multi-component reporter group binds to at least one reporter probe, or combinations thereof. Exemplary reporter probes include TaqMan® probes; Scorpion probes (also referred to as scorpion primers); Lux™ primers; FRET primers; Eclipse probes; molecular beacons, including but not limited to conventional FRET-based molecular beacons, multicolor molecular beacons, aptamer beacons, PNA beacons, antibody beacons, and probes comprising metallic nanoparticles and similar hybrid probes (see, e.g., Dubertret et al., Nature Biotech. 19:365-70, 2001). In certain embodiments, such reporter probes further comprise groove binders, including but not limited to minor groove binders, such as but not limited to TaqMan®MGB probes (Applied Biosystems). In certain embodiments, reporter probes further comprise spanning or bridging oligonucleotides, and enhancer probes, for example but not limited to LNA-enhancer probes (see, e.g., Jacobsen et al., Nucl. Acid Res., 30(19):e100, 2002).

A "substituted hydrocarbon", as that term is used herein, comprises a hydrocarbon where at least one of the hydrogen atoms in the hydrocarbon assembly is replaced by: a hydrocarbon; a heterocyclic hydrocarbon; a substituted heterocyclic hydrocarbon; halogen; azide, cyanide, isocyanide, isocyanate, isothiocyanate, —OSO3-, —OSO3R, —SO3-, —SO3R, —OC(O)R, —OC(O)OR, —OR, —CO2R, —C(O)NR2, —NR2, —NRC(O)R, —N(C(O)R)$_2$, —SR, —OP(O)(OR)$_2$, —OP(O)(OR)R, —OP(O)R2, —P(O)(OR)$_2$, —P(O)(OR)R, —P(O)R2, where R comprises hydrogen, hydrocarbon, heterocyclic hydrocarbon, substituted heterocyclic hydrocarbon, or substituted hydrocarbon. A hydrocarbon comprises an assembly of at least one carbon atoms where any carbon valences not used for forming one or more bonds with another carbon atom are used for bonding with hydrogen atoms. A hydrocarbon assembly comprises: a linear chain of carbon atoms where each of the carbon atoms is connected to a neighboring carbon atom by a single, double, or triple bond; a cyclic chain of carbon atoms where each of the carbon atoms is connected to at least two other carbon atom by a single, double, or in some unusual cases a triple bond; multiple cyclic chains of carbon atoms as described above where at least two of the cyclic chains share at least one common carbon-carbon single or multiple bond to form a fused ring system; multiple cyclic chains of carbon atoms as describe above where at least two cyclic chains are connected together by at least one carbon-carbon single or double bond, but where two bound cyclic chains do not share a common carbon-carbon single or double bond.

The term "target nucleic acid sequence" or "target" as used herein refers to a specific nucleic acid oligomer, typically genomic DNA, that contains one or more target nucleotides. A target nucleotide is that nucleotide in the target nucleic acid sequence that is interrogated by one or more probes of one or more probe sets to determine its methylation state. Generally, a target nucleotide is a cytosine or a 5-methylcytosine in a CpG motif, but not always. While the target nucleic acid sequence is generally described as a single-stranded molecule, it is to be understood that double-stranded molecules that contain one or more target nucleotides are also considered target nucleic acid sequences. Target nucleic acid sequences can include both naturally-occurring and synthetic sequences. The term "template", when used in reference to interrogating at least one target nucleotide, typically refers to a synthetic target nucleic acid sequence.

A target nucleic acid sequence according to the present teachings may be derived from any living, or once living, organism, including but not limited to, prokaryotes, archaea, viruses, and eukaryotes. The target nucleic acid may originate from the nucleus, typically genomic DNA, or may be extranuclear, e.g., plasmid, mitochondrial, viral, etc. The skilled artisan appreciates that genomic DNA includes not only full length material, but also fragments generated by any number of means, for example but not limited to, enzyme digestion, sonication, shear force, and the like. In certain embodiments, the target nucleic acid sequence may be replicated in vitro provided that it retains its methylation state, for example without limitation, amplification in the presence of S-adenyosyl methionine and an appropriate methylase, such as CpG Methylase (M.Sss I) or Human DNA (cytosine-5) Methyltransferase (Dnmt1), commercially available with appropriate reagents from New England Biolabs.

A wide variety of nucleic acid isolation techniques are well known in the art and are useful in generating target nucleic acid sequences for use in the teachings herein. Detailed descriptions of such techniques can be found in, among other places, Ausbel et al.; Rapley; Sambrook et al.; see also, ABI PRISM™ 6100 Nucleic Acid PrepStation and ABI PRISM™ 6700 Automated Nucleic Acid Workstation (Applied Biosystems, Foster); BloodPrep™ Chemistry and NucPrep™ Chemistry kits (Applied Biosystems).

II. Techniques

A. Ligation

Ligation according to the present teachings comprises any enzymatic or non-enzymatic means wherein an inter-nucleotide linkage is formed between the opposing ends of nucleic acid probes that are adjacently hybridized on a target nucleic acid sequence (i.e., generating a (mis)ligation product). Typically, the opposing ends of the annealed nucleic acid probes are suitable for ligation (suitability for ligation is a function of the ligation means employed). In certain embodiments, ligation also comprises at least one gap-filling procedure, wherein the ends of the two probes are not adjacently hybridized initially but the 3'-end of the upstream probe is extended by one or more nucleotide until it is adjacent to the 5'-end of the downstream probe, typically by a polymerase (see, e.g., U.S. Pat. No. 6,004,826). The internucleotide linkage can include, but is not limited to, phosphodiester bond formation. Such bond formation can include, without limitation, those created enzymatically by at least one DNA ligase or at least one RNA ligase, for example but not limited to, T4 DNA ligase, T4 RNA ligase, *Thermus thermophilus* (Tth) ligase, *Thermus aquaticus* (Taq) DNA ligase, *Thermus scotoductus* (Tsc) ligase, TS2126 (a thermophilic phage that infects Tsc) RNA ligase, *Archaeoglobus flugidus* (Afu) ligase, *Pyrococcus furiosus* (Pfu) ligase, *Thermococcus kodakaraensis* KOD1 ligase (lig$_{Tk}$), *Rhodothermus marinus* (Rm) ligase, *Methanobacterium thermoautotrophicum* (Mth) ligase, *Aquifex aeolicus* (Aae) ligase, *Aeropyrum pemix* K1 (Ape) ligase, or the like, including but not limited to, reversibly inactivated ligases (see, e.g., U.S. Pat. No. 5,773,258), and enzymatically active mutants or variants thereof.

Other internucleotide linkages include, without limitation, covalent bond formation between appropriate reactive groups such as between an α-haloacyl group and a phosphothioate group to form a thiophosphorylacetylamino group, a phosphorothioate a tosylate or iodide group to form a 5'-phosphorothioester, and pyrophosphate linkages.

Chemical ligation can, under appropriate conditions, occur spontaneously such as by autoligation. Alternatively, "activating" or reducing agents can be used. Examples of activating and reducing agents include, without limitation, carbodiimide, cyanogen bromide (BrCN), imidazole, 1-methylimidazole/carbodiimide/cystamine, N-cyanoimidazole, dithiothreitol (DTT) and ultraviolet light, such as used for photoligation.

Ligation generally comprises at least one cycle of ligation, i.e., the sequential procedures of: hybridizing the target-specific portions of a first probe and a corresponding second probe to their respective complementary regions on the corresponding target nucleic acid sequences; ligating the 3' end of the upstream probe with the 5' end of the downstream probe to form a ligation product; and denaturing the nucleic acid duplex to release the ligation product from the ligation product:target nucleic acid sequence duplex. The ligation cycle may or may not be repeated, for example, without limitation, by thermocycling the ligation reaction to amplify the ligation product using ligation probes (as distinct from using primers and polymerase to generate amplified ligation products). In certain embodiments, ligating or generating a (mis)ligation product comprises a multiplicity of cycles of ligation.

Also within the scope of the current teachings are ligation means such as gap-filling ligation, including, without limitation, gap-filling OLA and LCR, bridging oligonucleotide ligation, and correction ligation. Descriptions of these techniques can be found in, among other places, U.S. Pat. Nos. 5,185,243 and 6,004,826; published European Patent Applications EP 320308 and EP 439182; and PCT Publication Nos. WO 90/01069 and WO 01/57268.

A "ligation agent", according to the present invention, can comprise any number of enzymatic or non-enzymatic reagents. For example, ligase is an enzymatic ligation reagent that, under appropriate conditions, forms phosphodiester bonds between the 3'-OH and the 5'-phosphate of adjacent nucleotides in DNA molecules, RNA molecules, or hybrids (depending on the ligase). Temperature sensitive ligases, include, but are not limited to, bacteriophage T4 ligase and *E. coli* ligase. Thermostable ligases include, but are not limited to, Afu ligase, Taq ligase, Tfl ligase, Mth ligase, Tth ligase, Tth HB8 ligase, *Thermus* species AK16D ligase, Ape ligase, $Lig_{Tk}$ ligase Aae ligase, Rm ligase, and Pfu ligase (see, e.g., Housby et al., Nucl. Acids Res. 28:e10, 2000; Tong et al., Nucl. Acids Res. 28:1447-54, 2000; Nakatani et al., Eur, J. Biochem. 269:650-56, 2002; Zirvi et al., Nucl. Acids Res. 27:e40, 1999; Sriskanda et al., Nucl. Acids Res. 11:2221-28, 2000; and co-filed U.S. Provisional Patent Application Ser. No. 60/567,120, filed Apr. 30, 2004, entitled "Compositions, Methods, and Kits for (Mis)ligating Oligonucleotides, by Karger et al. The skilled artisan will appreciate that any number of thermostable ligases, including DNA ligases and RNA ligases, can be obtained from thermophilic or hyperthermophilic organisms, for example, certain species of eubacteria and archaea, including viruses that infect such thermophilic or hyperthermophilic organisms; and that such ligases can be employed in the disclosed methods and kits.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in, among other places, Xu et al., Nucl. Acids Res., 27:875-81 (1999); Gryaznov and Letsinger, Nucl. Acids Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucl. Acids Res. 20:3005-09 (1992); Sievers and von Kiedrowski, Nature 369:221-24 (1994); Liu and Taylor, Nucl. Acids Res. 26:3300-04 (1999); Wang and Kool, Nucl. Acids Res. 22:2326-33 (1994); Purmal et al., Nucl. Acids Res. 20:3713-19 (1992); Ashley and Kushlan, Biochemistry 30:2927-33 (1991); Chu and Orgel, Nucl. Acids Res. 16:3671-91 (1988); Sokolova et al., FEBS Letters 232:153-55 (1988); Naylor and Gilham, Biochemistry 5:2722-28 (1966); James and Ellington, Chem. & Biol. 4:595-605 (1997); and U.S. Pat. No. 5,476,930.

Photoligation using light of an appropriate wavelength as a ligation agent is also within the scope of the teachings. In certain embodiments, photoligation comprises probes comprising nucleotide analogs, including but not limited to, 4-thiothymidine ($s^4T$), 5-vinyluracil and its derivatives, or combinations thereof. In certain embodiments, the ligation agent comprises: (a) light in the UV-A range (about 320 nm to about 400 nm), the UV-B range (about 290 nm to about 320 nm), or combinations thereof, (b) light with a wavelength between about 300 nm and about 375 nm, (c) light with a wavelength of about 360 nm to about 370 nm; (d) light with a wavelength of about 364 nm to about 368 nm, or (e) light with a wavelength of about 366 nm. In certain embodiments, photoligation is reversible. Descriptions of photoligation can be found in, among other places, Fujimoto et al., Nucl. Acid Symp. Ser. 42:39-40 (1999); Fujimoto et al., Nucl. Acid Res. Suppl. 1:185-86 (2001); Fujimoto et al., Nucl. Acid Suppl., 2:155-56 (2002); Liu and Taylor, Nucl. Acid Res. 26:3300-04 (1998) and on the world wide web at: sbchem.kyoto-u.ac.jp/saito-lab.

When used in the context of the present teachings, "suitable for ligation" refers to at least one first probe and at least one corresponding second probe, wherein each probe comprises an appropriately reactive group based on the ligation means employed. Exemplary reactive groups include, but are not limited to, a free hydroxyl group on the 3' end of the upstream probe and a free phosphate group on the 5' end of the downstream probe, phosphorothioate and tosylate or iodide, esters and hydrazide, $RC(O)S^-$, haloalkyl, $RCH_2S$ and $\alpha$-haloacyl, thiophosphoryl and bromoacetoamido groups, and S-pivaloyloxymethyl-4-thiothymidine.

B. Amplification

Amplification according to the present invention encompasses any means by which at least a part of at least one (mis)ligation product, at least one (mis)ligation product surrogate, or combinations thereof, is reproduced, typically in a template-dependent manner, including without limitation, a broad range of techniques for amplifying nucleic acid sequences, either linearly or exponentially (i.e., generating an amplified (mis)ligation product or generating an amplified digested (mis)ligation product). Exemplary means for performing an amplifying step include ligase chain reaction (LCR), PCR, primer extension, strand displacement amplification (SDA), multiple displacement amplification (MDA), nucleic acid strand-based amplification (NASBA), rolling circle amplification (RCA), transcription-mediated amplification (TMA), and the like, including multiplex versions or combinations thereof, for example but not limited to, OLA/PCR, PCR/OLA, LDR/PCR, PCR/LDR, LCR/PCR, PCR/LCR (also known as combined chain reaction or "CCR"), and the like. Descriptions of such techniques can be found in, among other places, Sambrook and Russell; Sambrook et al.; Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); Rapley; U.S. Pat. No. 6,027,998; PCT Publication Nos. WO 97/31256 and WO 01/92579; Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl. Acad Sci USA 99:5261-66 (2002); Barany and Gelfand, Gene 109:1-11 (1991); Walker et al., Nucl. Acid Res. 20:1691-96 (1992); Polstra et al., BMC lnf. Dis. 2:18-(2002); and Schweitzer and Kingsmore, Curr. Opin. Biotechnol. 12:21-7 (2001).

In certain embodiments, amplification comprises at least one cycle of the sequential steps of: hybridizing at least one primer with complementary or substantially complementary sequences in at least one (mis)ligation product, at least one (mis)ligation product surrogate, or combinations thereof; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally. In certain embodiments, newly-formed nucleic acid duplexes are not initially denatured, but are used in their double-stranded form in one or more subsequent steps and either or both strands can, but need not, serve as (mis)ligation product surrogates. In certain embodiments, single-stranded amplicons are generated and can, but need not, serve as (mis)ligation product surrogates.

Primer extension is an amplifying technique that comprises elongating at least one probe or at least one primer that is annealed to a template in the 5'=>3' direction using an amplifying means such as a polymerase. According to certain embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed probe or primer, to generate a complementary strand. In certain embodiments, primer extension can be used to fill a gap between two probes of a probe set that are hybridized to target sequences of at least one target nucleic acid sequence so that the two probes can be ligated together. In certain embodiments, the polymerase used for primer extension lacks or substantially lacks 5'-exonuclease activity.

The term "quantitative PCR", or "Q-PCR" refers to a variety of methods used to quantify the results of the polymerase chain reaction for specific nucleic acid sequences. Such methods typically are categorized as kinetics-based systems, that generally determine or compare the amplification factor, such as determining the threshold cycle ($C_t$), or as co-amplification methods, that generally compare the amount of product generated from simultaneous amplification of target and standard templates. Many Q-PCR techniques comprise reporter probes, intercalating dyes, or both. For example but not limited to TaqMan® probes (Applied Biosystems), i-probes, molecular beacons, Eclipse probes, scorpion primers, Lux™ primers, FRET primers, ethidium bromide, SYBR® Green I (Molecular Probes), and PicoGreen® (Molecular Probes).

C. Separation

Separating comprises any process that removes at least some unreacted components, at least some reagents, or both some unreacted components and some reagents from at least one (mis)ligation product, at least one (mis)ligation product surrogate, or combinations thereof. In certain embodiments, at least one (mis)ligation product, at least one amplified (mis)ligation product, at least one digested (mis)ligation product, at least one digested amplified (mis)ligation product, or combinations thereof, are separated from unreacted components and reagents, including but not limited to unreacted molecular species present in the sample, ligation reagents, amplification reagents, for example, but not limited to, unbound/unhybridized ligation probes, primers, enzymes, co-factors, unbound sample components, nucleotides, and the like. The skilled artisan will appreciate that a number of well-known separation means can be used in the methods disclosed herein.

Exemplary means/techniques for performing a separation step include gel electrophoresis, including but not limited to isoelectric focusing and capillary electrophoresis; dielectrophoresis; sorting, including but not limited to fluorescence-activated sorting techniques; chromatography, including but not limited to HPLC, FPLC, size exclusion (gel filtratiori) chromatography, affinity chromatography, ion exchange chromatography, hydrophobic interaction chromatography, immunoaffinity chromatography, and reverse phase chromatography; affinity tag binding, such as biotin-avidin, biotin-streptavidin, maltose-maltose binding protein (MBP), and calcium-calcium binding peptide; aptamer-target binding; hybridization tag-hybridization tag complement annealing; and the like. In certain embodiments, at least one (mis) ligation product, at least one (mis)ligation product surrogate, or combinations thereof are bound to one or more substrates and separated from unbound components. Detailed discussion of separation techniques can be found in, among other places, Rapley; Sambrook et al.; Sambrook and Russell; Ausbel et al.; Molecular Probes Handbook; Pierce Applications Handbook; Capillary Electrophoresis: Theory and Practice, P. Grossman and J. Colburn, eds., Academic Press (1992); PCT Publication No. WO 01/92579; and M. Ladisch, Bioseparations Engineering: Principles, Practice, and Economics, John Wiley & Sons (2001).

In certain embodiments, at least one separating step comprises at least one mobility-dependent analytical technique, for example but not limited to capillary electrophoresis. In certain embodiments, at least one separating step comprises at least one substrate, for example but not limited to binding at least one biotinylated nucleic acid molecule to at least one streptavidin-coated substrate. Suitable substrates include but are not limited to microarrays, appropriately treated or coated reaction vessels and surfaces, beads, for example but not limited to magnetic beads, latex beads, metallic beads, polymer beads, microbeads, and the like (see, e.g., Tong et al., Nat. Biotech. 19:756-59 (2001); Gerry et al., J. Mol. Biol. 292:251-62 (1999); Srisawat et al., Nucl. Acids Res. 29:e4 (2001); Han et al., Nat. Biotech. 19:631-35, 2001; and Stears et al., Nat. Med. 9:14045, including supplements, 2003). Those in the art will appreciate that the shape and composition of the substrate is generally not limiting. In certain embodiments, a plurality of (mis)ligation products, (mis)ligation product surrogates, or combinations thereof are resolved via a mobility-dependent analytical technique.

In certain embodiments, at least one (mis)ligation product, at least one (mis)ligation product surrogate, or combinations thereof are resolved (separated) by liquid chromatography. Exemplary stationary phase chromatography media for use in the teachings herein include reversed-phase media (e.g., C-18 or C-8 solid phases), ion-exchange media (particularly anion-exchange media), and hydrophobic interaction media. In certain embodiments, at least one (mis) ligation product, at least one (mis)ligation product surrogate, or combinations thereof can be separated by micellar electrokinetic capillary chromatography (MECC).

Reversed-phase chromatography is carried out using an socratic, or more typically, a linear, curved, or stepped solvent gradient, wherein the level of a nonpolar solvent such as acetonitrile or isopropanol in aqueous solvent is increased during a chromatographic run, causing analytes to elute sequentially according to affinity of each analyte for the solid phase. For separating polynucleotides, including (mis)ligation products and at least some (mis)ligation product surrogates, an ion-pairing agent (e.g., a tetra-alkylammonium) is typically included in the solvent to mask the charge of phosphate.

The mobility of (mis)ligation products and at least some (mis)ligation product surrogates can be varied by using mobility modifiers comprising polymer chains that alter the affinity of the probe for the solid, or stationary phase. Thus, with reversed phase chromatography, an increased affinity of the (mis)ligation products and at least some (mis)ligation product surrogates for the stationary phase can be attained by adding a moderately hydrophobic tail (e.g., PEO-containing polymers, short polypeptides, and the like) to the mobility modifier. Longer tails impart greater affinity for the solid phase, and thus require higher non-polar solvent concentration for the (mis)ligation products and/or (mis)ligation product surrogates to be eluted (and a longer elution time).

In certain embodiments, at least one (mis)ligation product, at least one (mis)ligation product surrogate, or combinations thereof are resolved by electrophoresis in a sieving or non-sieving matrix. In certain embodiments, the electrophoretic separation is carried out in a capillary tube by capillary electrophoresis (see, e.g., Capillary Electrophoresis: Theory and Practice, Grossman and Colburn eds., Academic Press (1992)). Exemplary sieving matrices for use in the disclosed teachings include covalently crosslinked matrices, such as polyacrylamide covalently crosslinked with bis-acrylamide; gel matrices formed with linear polymers (see, e.g., U.S. Pat. No. 5,552,028); and gel-free sieving media (see, e.g., U.S. Pat. No. 5,624,800; Hubert and Slater, Electrophoresis, 16: 2137-2142 (1995); Mayer et al., Analytical Chemistry, 66(10): 1777-1780 (1994)). The electrophoresis medium may contain a nucleic acid denaturant, such as 7M formamide, for maintaining polynucleotides in single stranded form. Suitable capillary electrophoresis instrumentation are commercially available, e.g., the ABI PRISM™ Genetic Analyzer series (Applied Biosystems).

In certain embodiments, at least one hybridization tag complement includes at least one hybridization enhancer, where, as used herein, the term "hybridization enhancer" means moieties that serve to enhance, stabilize, or otherwise positively influence hybridization between two polynucleotides, e.g. intercalators (see, e.g., U.S. Pat. No. 4,835,263), minor-groove binders (see, e.g., U.S. Pat. No. 5,801,155), and cross-linking functional groups. The hybridization enhancer may be attached to any portion of a mobility modifier, so long as it is attached to the mobility modifier is such a way as to allow interaction with the hybridization tag-hybridization tag complement duplex. In certain embodiments, at least one hybridization enhancer comprises at least one minor-groove binder, e.g., netropsin, distamycin, and the like.

The skilled artisan will appreciate that at least one (mis)ligation product, at least one (mis)ligation product surrogate, or combinations thereof can also be separated based on molecular weight and length or mobility by, for example, but without limitation, gel filtration, mass spectroscopy, or HPLC, and detected using appropriate methods. In certain embodiments, at least one (mis)ligation product, at least one (mis)ligation product surrogate, or combinations thereof are separated using at least one of the following forces: gravity, electrical, centrifugal, hydraulic, pneumatic, or magnetism.

In certain embodiments, at least one affinity tag is used to separate the element to which it is bound, e.g., at least one (mis)ligation product, at least one (mis)ligation product surrogate, or combinations thereof, from at least one component of a ligation reaction composition, a digestion reaction composition, an amplified ligation reaction composition, or the like. In certain embodiments, at least one affinity tag is used to bind at least one (mis)ligation product, at least one (mis)ligation product surrogate, or combinations thereof to at least one substrate, for example but not limited to at least one biotinylated (mis)ligation product, at least one biotinylated (mis)ligation product surrogate, or combinations thereof, to at least one substrate comprising streptavidin. In certain embodiments, at least one aptamer is used to bind at least one (mis)ligation product, at least one (mis)ligation product surrogate, or combinations thereof, to at least one substrate (see, e.g., Srisawat and Engelke, RNA 7:632-641 (2001); Holeman et al., Fold Des. 3:423-31 (1998); Srisawat et al., Nucl. Acid Res. 29(2):e4, 2001).

In certain embodiments, at least one hybridization tag, at least one hybridization tag complement, or at least one hybridization tag and at least one hybridization tag complement, is used to separate the element to which it is bound from at least one component of a ligation reaction composition, a digestion reaction composition, an amplified ligation reaction composition, or the like. In certain embodiments, hybridization tags are used to attach at least one (mis)ligation product, at least one (mis)ligation product surrogate, or combinations thereof, to at least one substrate. In certain embodiments, at least one (mis)ligation product, at least one (mis)ligation product surrogate, or combinations thereof, comprise the same hybridization tag. For example but not limited to, separating a multiplicity of different element:hybridization tag species using the same hybridization tag complement, tethering a multiplicity of different element:hybridization tag species to a substrate comprising the same hybridization tag complement, or both.

D. Determining

Determining comprises any means by which the methylation state of one or more target nucleotide is identified or inferred, including but not limited to evaluating the degree of methylation of one or more target nucleotides. In certain embodiments, determining comprises detecting at least one (mis)ligation product, at least one (mis)ligation product surrogate, or combinations thereof. In certain embodiments, determining further comprises quantifying the at least one detected (mis)ligation product, the at least one detected (mis)ligation product surrogate, or combinations thereof, for example but not limited to graphically displaying the quantified at least one (mis)ligation product, at least one (mis)ligation product surrogate, or combinations thereof on a graph, monitor, electronic screen, magnetic media, scanner print-out, or other two- or three-dimensional display. Typically the peak height, the area under the peak, the signal intensity of one or more detected reporter group on the (mis)ligation product or (mis)ligation product surrogate, or other quantifiable parameter of the (mis)ligation product or surrogate are measured and the amount of (mis)ligation product that was produced in a particular ligation assay is inferred. Generally, at least one quantified parameter for at least one (mis)ligation product, at least one (mis)ligation product surrogate, or combinations thereof, is compared to the same parameter(s) from a second (mis)ligation product, a second (mis)ligation product surrogate, or combinations thereof, for example but not limited to, a competing (mis) ligation product, and a ratio of the two (mis)ligation products is obtained.

By comparing the (mis)ligation product ratio obtained from an unknown sample with control ratios or standard curves for the same target nucleotide and using the same probes and assay conditions, one can determine the methylation state of the target nucleotide. For example, consider an illustrative competing misligation assay with two possible (mis)ligation products, e.g., LP1 and LP2. Assume in this illustration that the LP1:LP2 ratio for a particular unknown sample is 5:1 and the LP1:LP2 ratio obtained using a control target nucleic acid sequence known to be fully methylated was 5:1 and with a control target nucleic acid sequence known to be non-methylated was 1:1. By comparing the (mis)ligation product ratio obtained using the unknown sample with the two control samples, one can determine that the target nucleotide in the unknown sample was fully methylated. When the ligation product ratio obtained using the unknown sample is between 5:1 and 1:1 in this example, one can infer that the degree of target nucleotide methylation has an intermediate value that depends on those two control ratios. Using the standard curve for that probe set and assay conditions, one can plot the experimentally determined ligation product ratio on the curve and determine the corresponding degree of methylation.

In certain embodiments, at least one determining step comprises detecting and quantifying at least one (mis)ligation product parameter using at least one instrument, i.e., using an automated or semi-automated determining means that can, but need not, comprise a computer algorithm. In certain embodiments, the determining step is combined with or is a continuation of at least one separating step, for example but not limited to a capillary electrophoresis instrument comprising at least one fluorescent scanner and at least one graphing, recording, or readout component; a chromatography column coupled with an absorbance monitor or fluorescence scanner and a graph recorder; or a microarray with a data recording device such as a CCD camera. Exemplary means for performing a determining step include the ABI PRISM® 3100 Genetic Analyzer, ABI PRISM® 3100-Avant Genetic Analyzer, ABI PRISM® 3700 DNA Analyzer, ABI PRISM® 3730 DNA Analyzer, ABI PRISM® 3730x/DNA Analyzer (all from Applied Biosystems); the ABI PRISM® 7300 Real-Time PCR System; and microarrays and related software such as the ABI PRISM® 1700 (Applied Biosystems) and other commercially available array systems available from Affymetrix, Agilent, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003). Exemplary software includes GeneMapper™ Software, GeneScan® Analysis Software, and Genotyper® software (all from Applied Biosystems).

The generation and use of standard curves is well known to those in the art (see, e.g., Overholtzer et al., Proc. Natl. Acad. Sci. 100:11547-52, 2003). Typically, a standard-curve is generated by plotting experimentally obtained results for a particular set of reagents and under defined assay conditions on an X-Y graph or other coordinate system and then generating a curve, generally either manually or using one or more mathematical formula or algorithm, for example but not limited to graphing and/or line drawing software, linear regression analysis and similar mathematical calculations, computer algorithms, or the like. Once a standard curve have been generated for a given target nucleotide and at least one corresponding probe set or at least an appropriate subset of at least one corresponding probe set, experimentally-determined results obtained from test (unknown) samples using the same probes under the same assay conditions can be evaluated using the standard curve and the degree of target nucleotide methylation determined. The skilled artisan will appreciate that a "curve" can actually be a straight or substantially straight line or it can be curvilinear and assume a wide range of shapes.

To generate a standard curve for determining the degree of target nucleotide methylation, (mis)ligation assays are performed under set ("standard") conditions using appropriate probes, but with at least two target compositions comprising different known amounts of methylated target nucleotide sequences. For example but not limited to, a three sample assay where a first ligation reaction composition comprises non-methylated target nucleic acid sequences (0% target nucleic acid methylation), a second ligation reaction composition comprises a 1:1 mixture of methylated:non-methylated target nucleotide sequences (50% target nucleotide methylation), and the third ligation reaction composition comprises methylated target nucleic acid sequences (100% target nucleotide methylation) and a three point standard curve, using the ligation product ratios corresponding to 0, 50 and 100% target nucleic acid methylation, is generated; a four sample assay where a first ligation reaction composition comprises non-methylated target nucleic acid sequences (0% target nucleic acid methylation), a second ligation reaction composition comprises a 1:2 mixture of methylated:non-methylated target nucleotide sequences (33.3% target nucleotide methylation), a third product reaction composition comprises a 2:1 mixture of methylated:non-methylated target nucleotide sequences (66.6% target nucleotide methylation) and the fourth ligation reaction composition comprises methylated target nucleic acid sequences (100% target nucleotide methylation) a four point standard curve, based on the ligation product ratios corresponding to 33.3, 50 and 100% target nucleic acid methylation, is generated; and so forth. The skilled artisan appreciates that the accuracy of standard curves generally increases as the number of data points used to generate the curve increases and also as the number of replicate assays are performed. The skilled artisan also appreciates that controls and/or calibration standards can be included either with unknowns or run in parallel.

According to the present teachings, at least one step for interrogating at least one target nucleotide is performed using the disclosed probes and probe sets; at least one step for generating at least one (mis)ligation product is performed using the disclosed ligation agents and ligation techniques; at least one step for generating at least one amplified (mis)ligation product and/or (mis)ligation product surrogate is performed using the disclosed amplifying means and amplification techniques; at least one step for generating at least one digested (mis)ligation product is performed using the disclosed nucleases, restriction enzymes, chemical digesting means, and digestion techniques; and at least one step for determining the degree of methylation of at least one target nucleotide is performed using at least one disclosed detecting technique, at least one quantifying technique, at least one disclosed separating technique, or combinations thereof.

Aspects of the present teachings may be further understood in light of the following examples, which should not be construed as limiting the scope of the teachings in any way.

III. EXEMPLARY EMBODIMENTS

The present teachings are directed to methods, reagents, and kits that are useful for determining the degree of target nucleotide methylation. The skilled artisan will appreciate that when analyzing genomic DNA there are typically multiple copies of the same nucleic acid sequence in the sample being evaluated, each containing the target nucleotide. The degree of methylation for that target nucleotide is generally determined from the sum of at least some of the (mis)ligation products obtained using at least part of that population of target nucleic acid sequences.

In certain embodiments, for each target nucleotide to be interrogated, there are at least two probe sets, a first probe set and at least one second probe set. In certain embodiments, when the upstream and downstream probes of the first probe set are hybridized with the target nucleic acid sequence, the first probe set ligation site includes the complement of the target nucleotide. The ligation site for the second probe set(s) is a few nucleotides upstream or downstream from the target nucleotide, as shown in FIG. 1. The first probe set and at least one second probe set compete with one another to hybridize with the target nucleic acid sequence and be ligated. The ligation rate of the first probe set compared to the second probe set, i.e., the ligation rate ratios, can differ depending on whether the target nucleotide is methylated.

Figure 3:
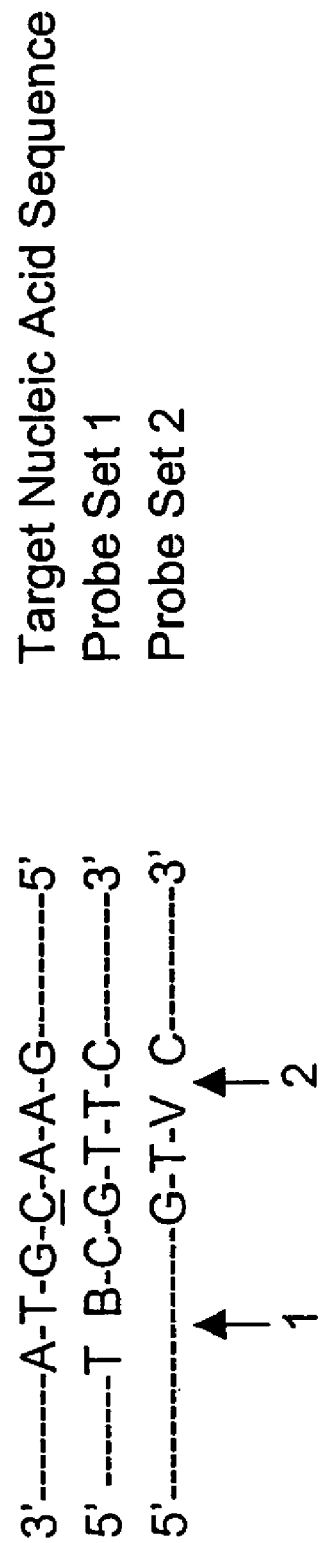
FIG. 3: Schematically depicts an exemplary misligation reaction with probes from two competing probe sets. The target nucleotide in the target nucleic acid sequence is underlined. The 3'-end of the upstream probe for probe set 1 comprises the nucleotide-T and the 5'-end of the downstream probe comprises B-C-G-T-T-C-. B represents any of C, G, T, or U, including but not limited to analogs and Modifications thereof; but not A. The 3'-end of the upstream probe for probe set 2 comprises the nucleotides -G-T-V and the 5'-end of the downstream probe comprises C-. V represents any of A, C, or G, including but not limited to analogs and Modifications thereof; but not T or U. The ligation sites for probe sets 1 and 2 are shown by arrows 1 and 2, respectively.

In certain embodiments, the degree of target nucleotide methylation is determined by comparing one or more quantified parameters between two or more (mis)ligation products or their surrogates, at least one quantified (mis)ligation product parameter and one or more standard curve, or both. In certain embodiments, at least one probe set comprises one or more nucleotides on or near the 3'-end of the upstream probe, on or near the 5'-end of the downstream probe, or both, that is not complementary to the corresponding nucleotide(s) on the target nucleic acid sequence. The corresponding nucleotide on the target nucleic acid sequence can, but need not, be the target nucleotide. In certain embodiments, the ligation site (in these embodiments, where the misligation occurs), comprises the nucleotide opposing the target nucleotide, as shown in FIG. 2. In certain embodiments, the ligation site is upstream or downstream of the target nucleotide and can (as shown in FIG. 3), but need not, comprise one or more mismatched nucleotide. Those in the art will appreciate that the terms upstream or 5' probe and downstream or 3' probe are used in reference to their annealing position on the corresponding target nucleic acid sequence in the 3'=>5' orientation.

In certain embodiments, at least one ligation rate, at least one misligation rate, or combinations thereof are changed by the presence of at least one Modification in at least one probe set. In certain embodiments, at least one ligation rate, at least one misligation rate, or combinations thereof are changed due to changing the hybridization and or ligation reaction composition or conditions, for example but not limited to, salt concentration, temperature, changes in one or more cofactor (e.g., α-thio ATP, γ-thio ATP), addition of one or more denaturant, or the like. In certain embodiments, changing the divalent cation, for example without limitation, substituting a manganese or calcium salt for a magnesium salt, changes at least one ligation rate, at least one misligation rate, or combinations thereof (see, e.g., Tong et al., Nucl. Acids Res. 28:1447-54, 2000; Nakatani et al., Eur. J. Biochem. 269:650-56, 2002; Tong et al., Nucl. Acids Res. 27:788-94, 1999). In certain embodiments, changing at least one ligation rate, at least one misligation rate, or combinations thereof also changes at least one ligation rate ratio, at least one misligation rate ratio, or combinations thereof.

Example 1

Ligation Assay

The degree of target nucleotide methylation was determined using a methylated (comprising a 5-$^{Me}$C) or non-methylated synthetic model template:

TTATTATGTGGGGCGGAC<u>C</u>GCGTGCGCTTACTTAT (SEQ ID NO:1).

The underlined cytosine is the methylated/non-methylated target nucleotide in this exemplary target nucleic acid sequence. The probe sets used are shown in Table 1. The underlined nucleotide in each probe set is designed to be the hybridization partner of the target nucleotide. The upstream probes in each probe set comprised the fluorescent reporter group FAM®. The 5'-end of all of the downstream (3'-) probes in this and all other examples described herein were phosphorylated to render them suitable for ligation. Each assay in this example was performed with at least two competing probe sets.

TABLE 1

Ligation Probe Sets

| Probe Set | upstream probe | | downstream probe | |
|---|---|---|---|---|
| 1 | FAM-AGCGCACGC<u>G</u><br>probe 2 | (SEQ ID NO:2) | GTCCGCCCCAC<br>probe 3 | (SEQ ID NO:3) |
| 2 | FAM-AGCGCACGC<u>G</u>GT<br>probe 4 | (SEQ ID NO:4) | CCGCCCCACAT<br>probe 5 | (SEQ ID NO:5) |

TABLE 1-continued

Ligation Probe Sets

| Probe Set | upstream probe | downstream probe |
|---|---|---|
| 3 | FAM-AGCGCACGCGGTC (SEQ ID NO:6) probe 6 | CGCCCCACATA (SEQ ID NO:7) probe 7 |

In this exemplary embodiment, ligation reaction compositions were formed by combining either the methylated or non-methylated synthetic model template with 12.5 nM of each probe from two of the probe sets shown in Table 1, less than 12.5 nM template, 2 or 4 units of Afu ligase, and ligase buffer (50 mM Tris-HCl (pH 7.5), 10 mM MgCl$_2$, 10 mM dithiothreitol (DTT), 1 mM ATP, and 25 µg/ml bovine serum albumin) in a final volume of 20 µl. To generate ligation products, the ligation reaction composition was cycled at (65° C. for 5 seconds and 45° C. for 1 minute) for 50 cycles, heated to 99° C. for 10 minutes, then cooled to 4° C.

Figure 4:
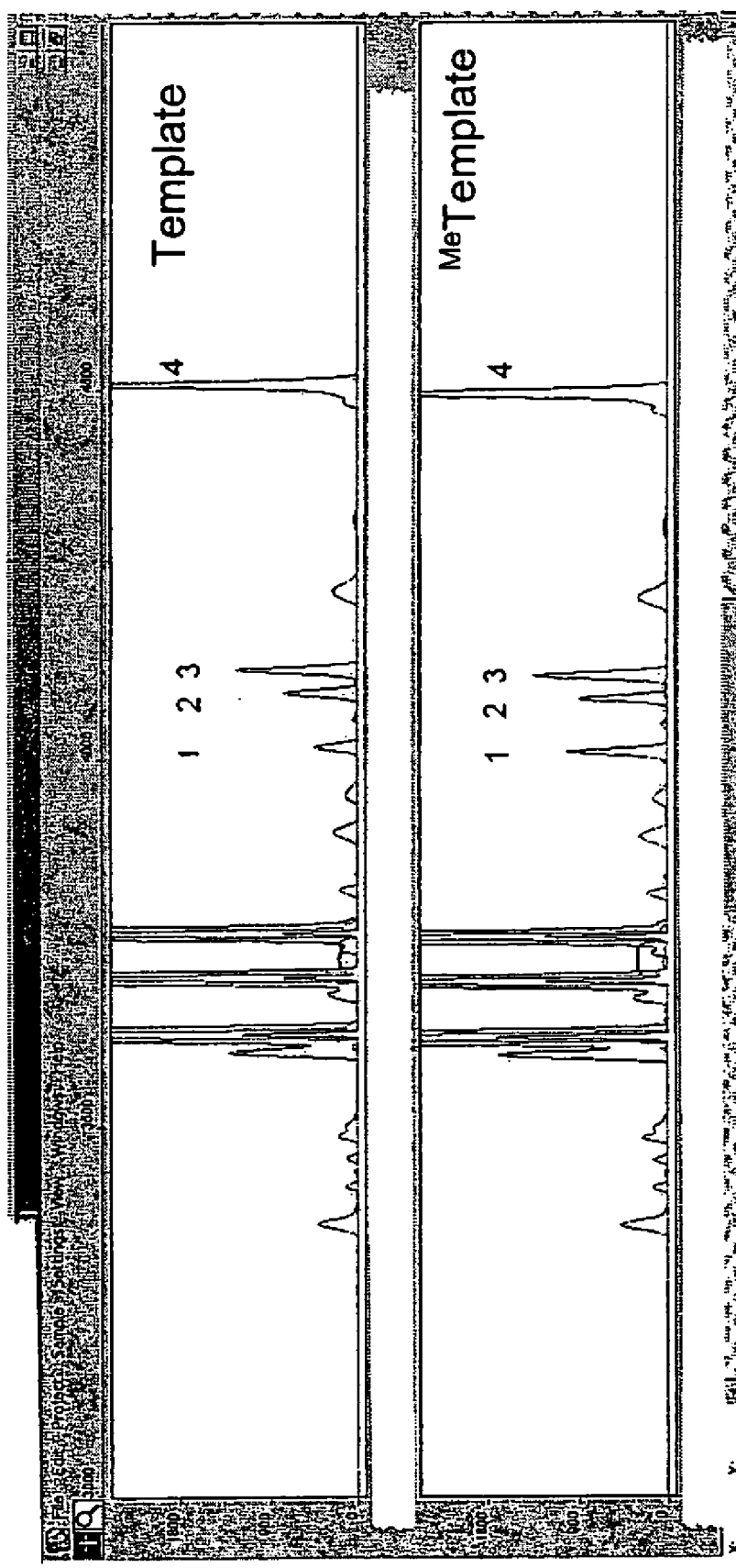
FIG. 4: Depicts an electropherogram showing ligation product peaks obtained from an illustrative ligation assay, described in Example 1. The upper panel shows the results obtained using a non-methylated synthetic model template ("Template") and the lower panel shows the results obtained when the synthetic model template comprised 5-methylcytosine as the target nucleotide ("$^{Me}$Template"). The peak corresponding to the ligation product of Probe Set 1 is marked "1", the peak corresponding to the ligation product of Probe Set 2 is marked "2", and the peak corresponding to the ligation product of Probe Set 3 is marked "3". The peak marked 4 is the internal size standard.

Two µL of the ligation product composition was combined with 18 µL Hi-Di formamide (Applied Biosystems) and the diluted ligation products were separated and detected using capillary electrophoresis in 36 cm capillaries with POP-6™ polymer on the ABI PRISM® 3100 Genetic Analyzer in the gene scan mode using GeneScan® Analysis Software according to the manufacturer's instructions (Applied Biosystems). The software determines, among other things, peak height and peak area (integrated area under the peak). As shown in FIG. 4, the peak height for the ligation product of probes 2 and 3 ("1") was two to three times higher with the methylated template than with the non-methylated template, indicating that the ligation rate for Probe Set 1 was enhanced when the target nucleotide was methylated. The ligation rates for the other two probe sets in this example were much less effected by the methylation state of the target nucleotide. The ligation product ratios for probe set 1:probe set 2 ("1"/"2") was 0.6 with the synthetic model template comprising the non-methylated target nucleotide and 1.22 with the synthetic template comprising the methylated target nucleotide; and for probe set 1:probe set 3 ("1"/"3"), 0.36 with the non-methylated template and 0.81 with the methylated template (see FIG. 4).

The skilled artisan will appreciate that not every probe or every probe set will satisfactory distinguish the methylated target nucleotide from the non-methylated target nucleotide. The skilled artisan understands, however, that appropriate probes and probe sets can be obtained by routine evaluation of candidate probes and probe sets, without undue experimentation. Additionally, when using an NAD$^+$-dependent ligase, those in the art will understand that NAD+ is generally used as the co-factor in the ligation buffer, rather than ATP. Typically, eubacterial ligases are NAD$^+$-dependent while eukaryotic, viral, and archaeal ligases are ATP-dependent (see, e.g., Weller and Dohertry, FEBS Letters 505:340-342, 2002).

Example 2

Competing Misligation Assay

A probe set comprising a single base mismatch at the 3' end of each of the upstream probes was prepared for interrogating the target nucleotide in the methylated or non-methylated synthetic template corresponding to a segment of the promoter of the P16 tumor suppressor gene: CCAGAGGGTGGGGCGGAC_C_GAGTGCGCTCGGCGGCT (SEQ ID NO:17), where the underlined "C" is either cytosine (non-methylated template) or 5-methylcytosine (methylated template). This probe set comprised three different upstream probes and one downstream probe, shown in Table 2. Each of the upstream probes comprised the fluorescent reporter group FAM and two of the upstream probes comprised polyethylene oxide mobility modifiers, shown as (PEO) and (PEO)$_2$.

TABLE 2

Probe Set 4

| 5' probes | | 3' probe |
|---|---|---|
| FAM-AGCGCACTCA probe 8 | (SEQ ID NO:8) | |
| FAM-(PEO)-AGCGCACTCC probe 9 | (SEQ ID NO:9) | GTCCGCCCCAC (SEQ ID NO:10) probe 10 |
| FAM-(PEO)$_2$-AGCGCACTCT probe 11 | (SEQ ID NO:11) | |

Figure 5A:
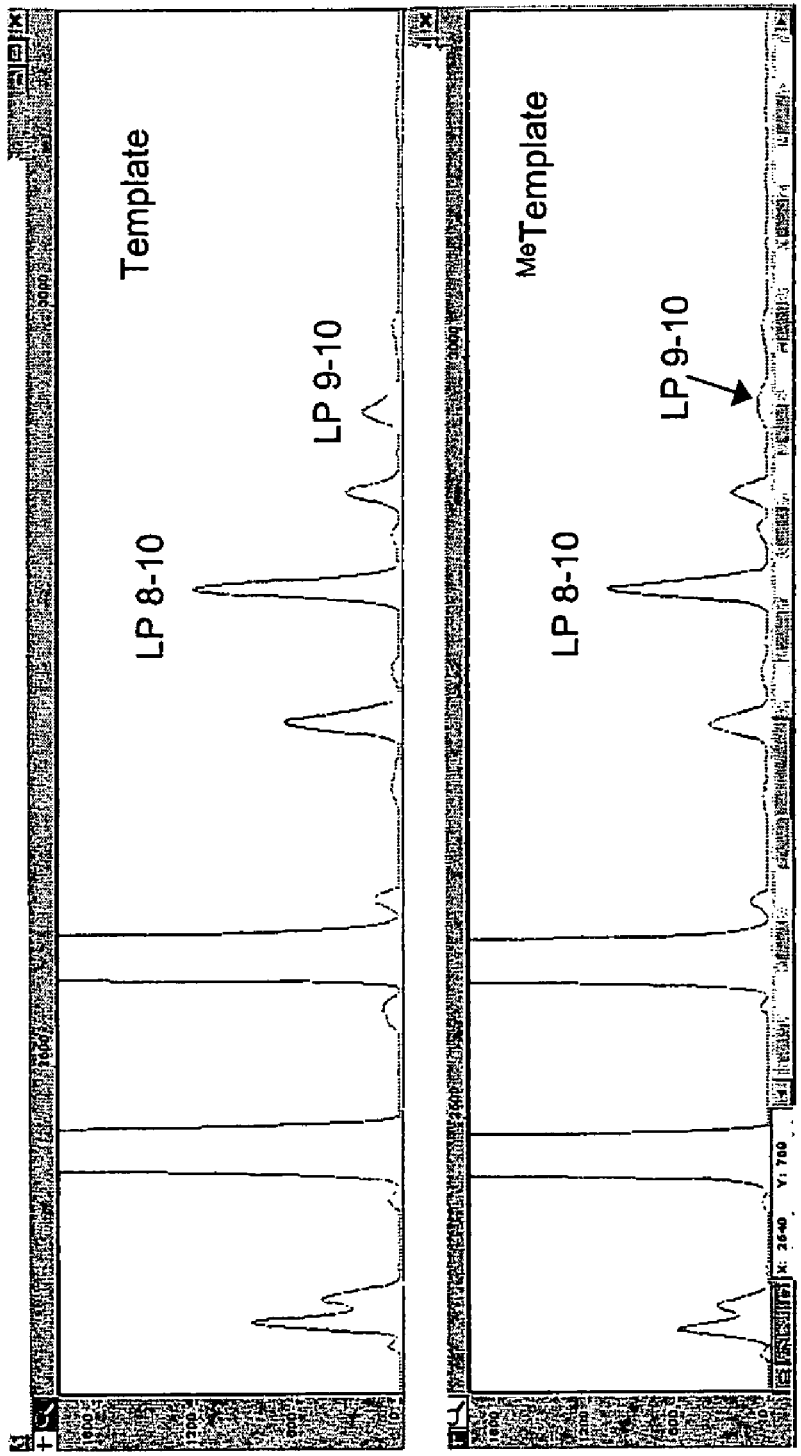
FIGS. 5A-C: Depict electropherograms showing misligation product peaks obtained from an exemplary competitive ligation assay, described in Example 2. The upper panels show the results obtained using a non-methylated synthetic P16 template ("Template") and the lower panels and the lower panels show the results obtained when the synthetic P16 template comprised 5-methylcytosine as the target nucleotide ("$^{Me}$Template"). The peak corresponding to the misligation product generated using ligation probes 8 and 10 is marked "LP 8-10", the peak corresponding to the misligation product generated using ligation probes 9 and 10 is marked "LP 9-10", and the peak corresponding to the misligation product generated using ligation probes 10 and 11 is marked "LP 11-10".
Figure 5B:
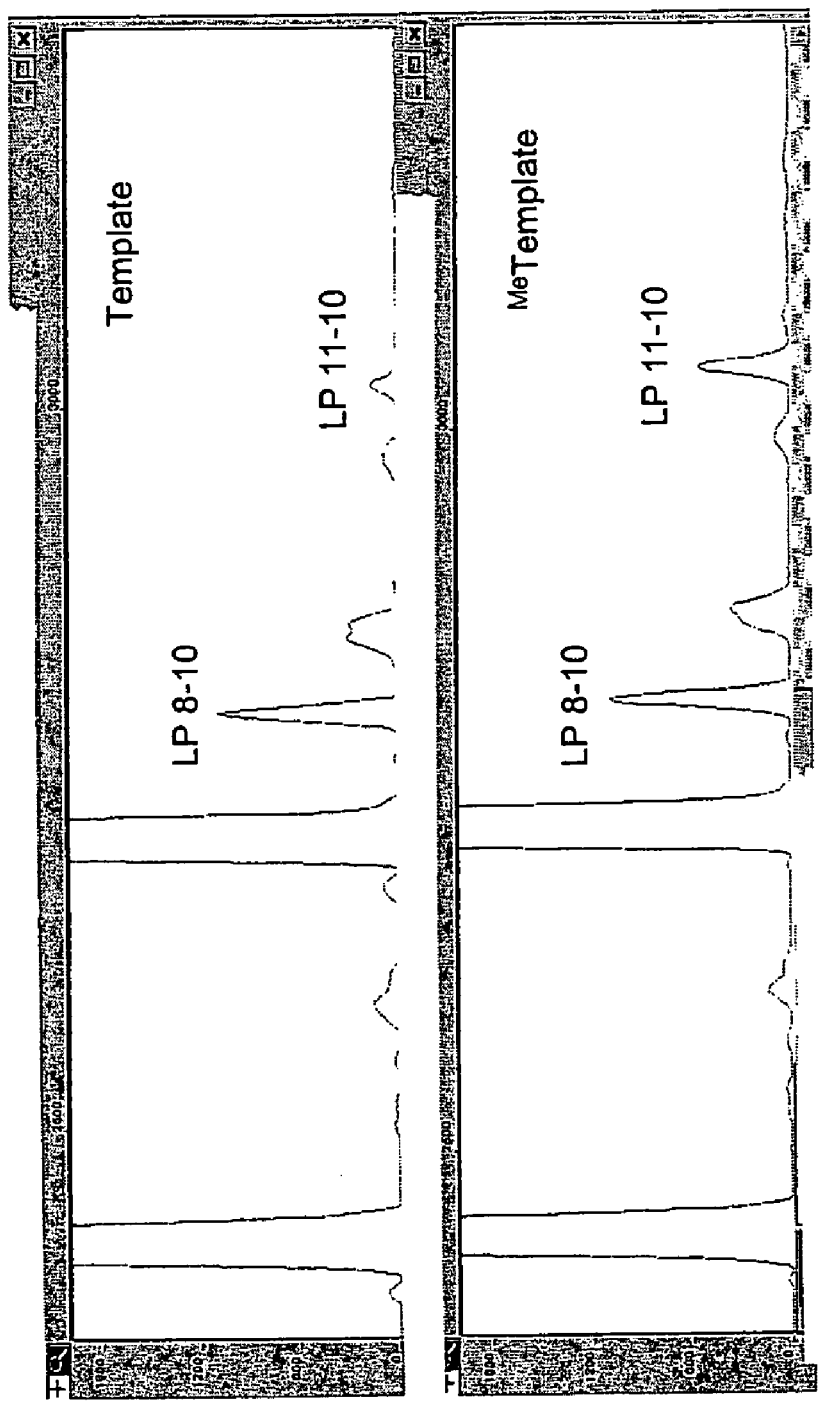
Figure 5C:
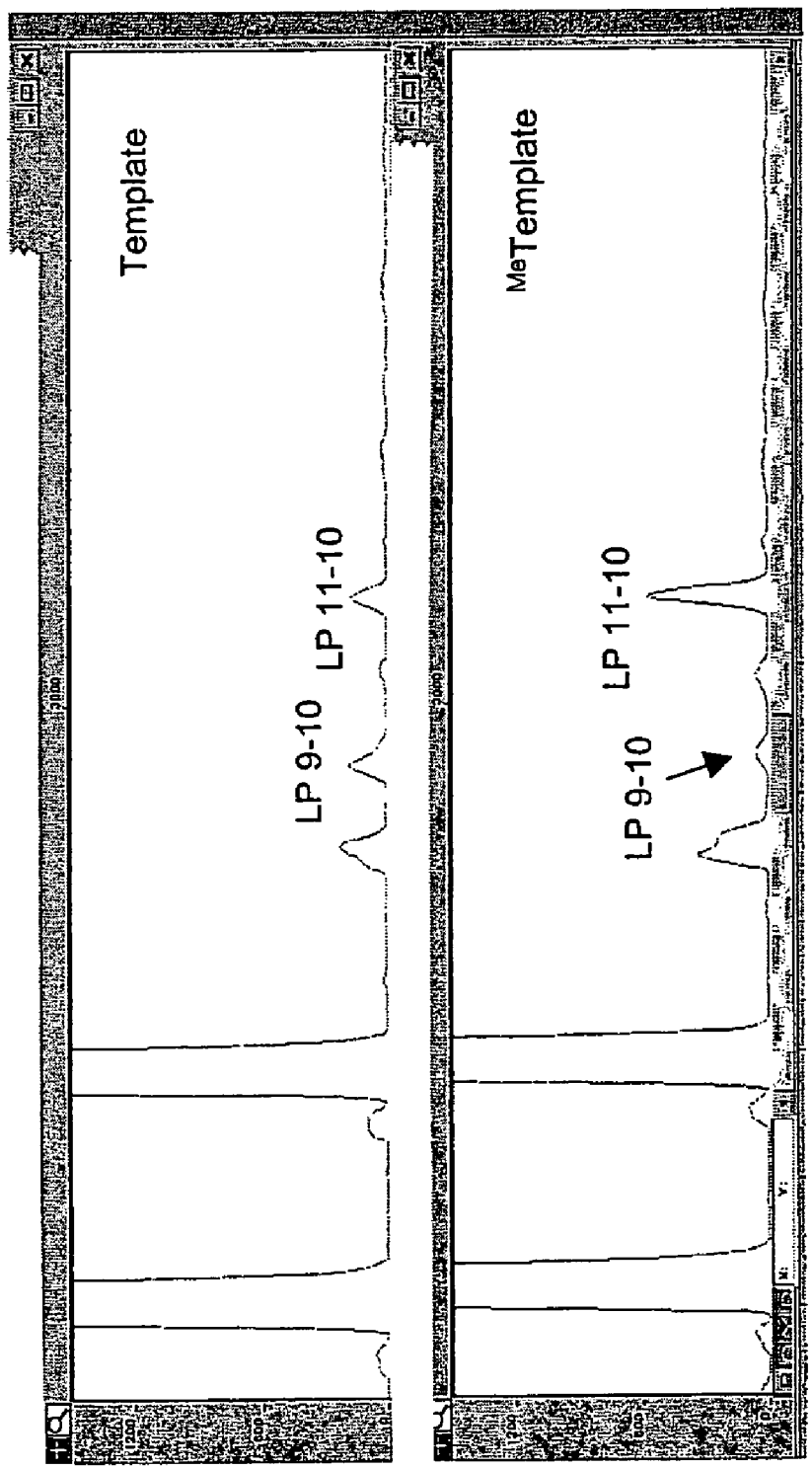

In each assay, two competing upstream probes and the downstream probe were used. The ligation reaction composition was generally as described in Example 1 except that 2 units of Afu ligase, 12.5 nM template, and probes from Probe Set 4 were used for interrogating the target nucleotide, in a reaction volume of 10 µL. To generate ligation products, the ligation reaction composition was heated to 90° C. for 3 minutes, thermocycled (90° C. for 10 seconds, 45° C. for 5 minutes) for 40 cycles, heated to 99.9° C. for 20 minutes, then cooled to 4° C. The ligation products were diluted in formamide, separated, detected, and analyzed as described in Example 1. The ligation product ratio for the ligation product of probes 8 and 10 compared to the ligation product of probes 9 and 10 (LP 8-10/LP 9-10) was 4.38 when the template comprising the non-methylated target nucleotide was interrogated and 8.94 when the template comprising the methylated target nucleotide was interrogated (see FIG. 5A). The ligation product ratio for the ligation product of probes 11 and 10 (LP 11-10) compared to LP 8-10 (LP 11-10/LP 8-10) was 0.16 when the non-methylated template was used and 0.54 when the template was methylated (see FIG. 5B). The ligation product ratio for LP 11-10 compared to LP 9-10 was 0.83 when the non-methylated template was used and 9.82 when the template comprising the methylated target nucleotide was interrogated (see FIG. 5C).

Example 3

Competing Misligation Assay

A probe set comprising a single base mismatch at the 3' end of each of the upstream probes (shown underlined in Table 3) was prepared for interrogating the methylated or unmethylated target nucleotide (underlined) in a synthetic template derived from the transcriptional regulator gene E2F2:

```
                                                 (SEQ ID NO:12)
TCCGGGATGCACAGTGCAGAGGCGGCCAGAGCAGTGCACAGCG.
```

The probe set comprised three different upstream probes and one downstream probe. Each of the upstream probes comprised a mismatched nucleotide on its 3' end (shown underlined) and the fluorescent reporter group FAM and two of the upstream probes comprised polyethylene oxide mobility modifiers, shown as (PEO) and (PEO)$_2$ in Table 3.

tion, detection and methylation analysis were generally as described in Example 2, except that the reaction composition was cycled for forty cycles between 90° C. for ten seconds and 50° C. for five minutes.

Figure 6A:
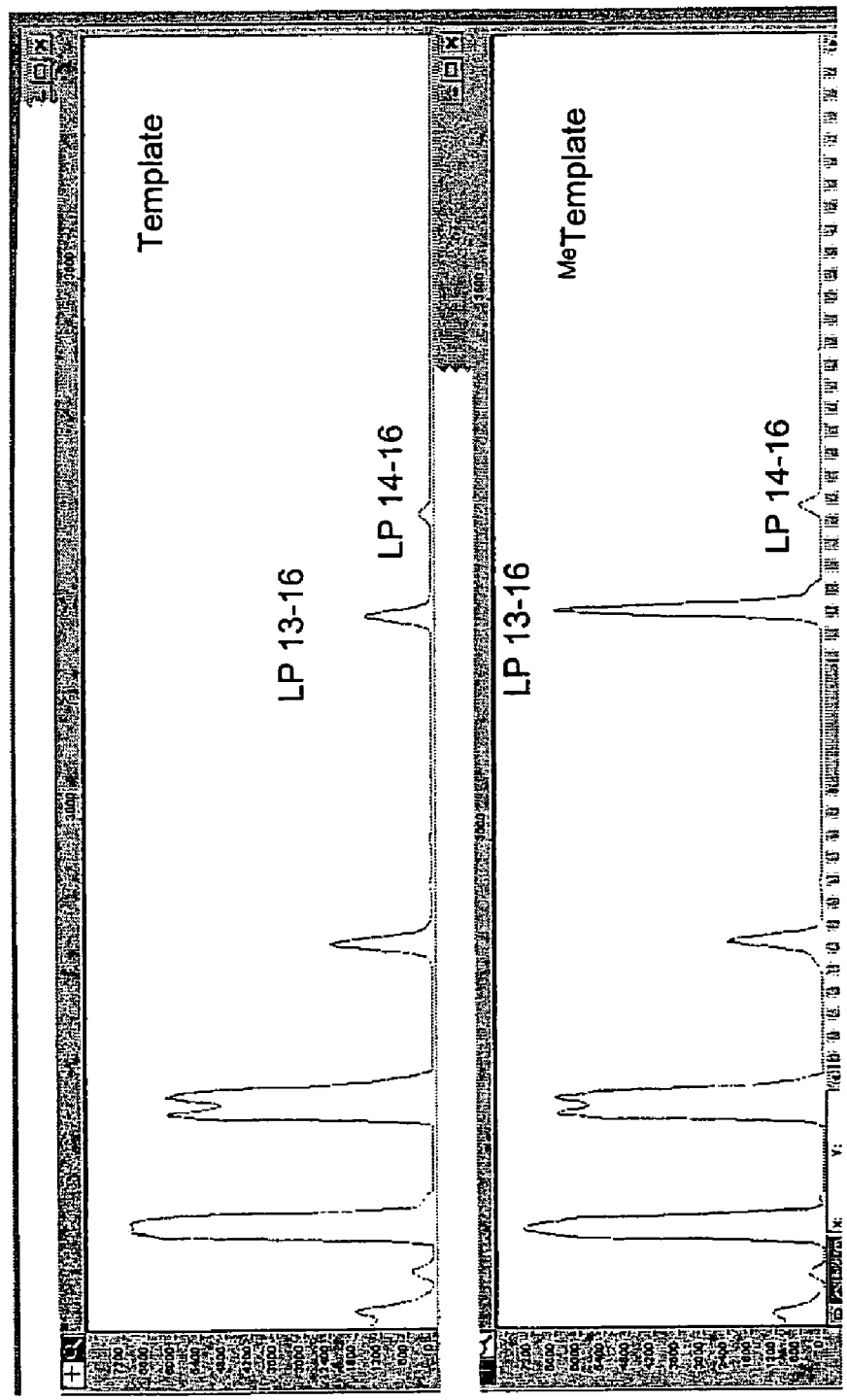
FIGS. 6A-C: depict electropherograms showing misligation product peaks obtained from an exemplary misligation assay, described in Example 3. The peak corresponding to the misligation product generated using ligation probes 13 and 16 is marked "LP 13-16", the peak corresponding to the misligation product generated using ligation probes 14 and 16 is marked "LP 14-16", and the peak corresponding to the misligation product generated using ligation probes 15 and 16 is marked "LP 15-16". The upper panels show the results obtained using non-methylated templates ("Template") and the lower panels show the results obtained using methylated templates ("$^{Me}$Template").
Figure 6B:
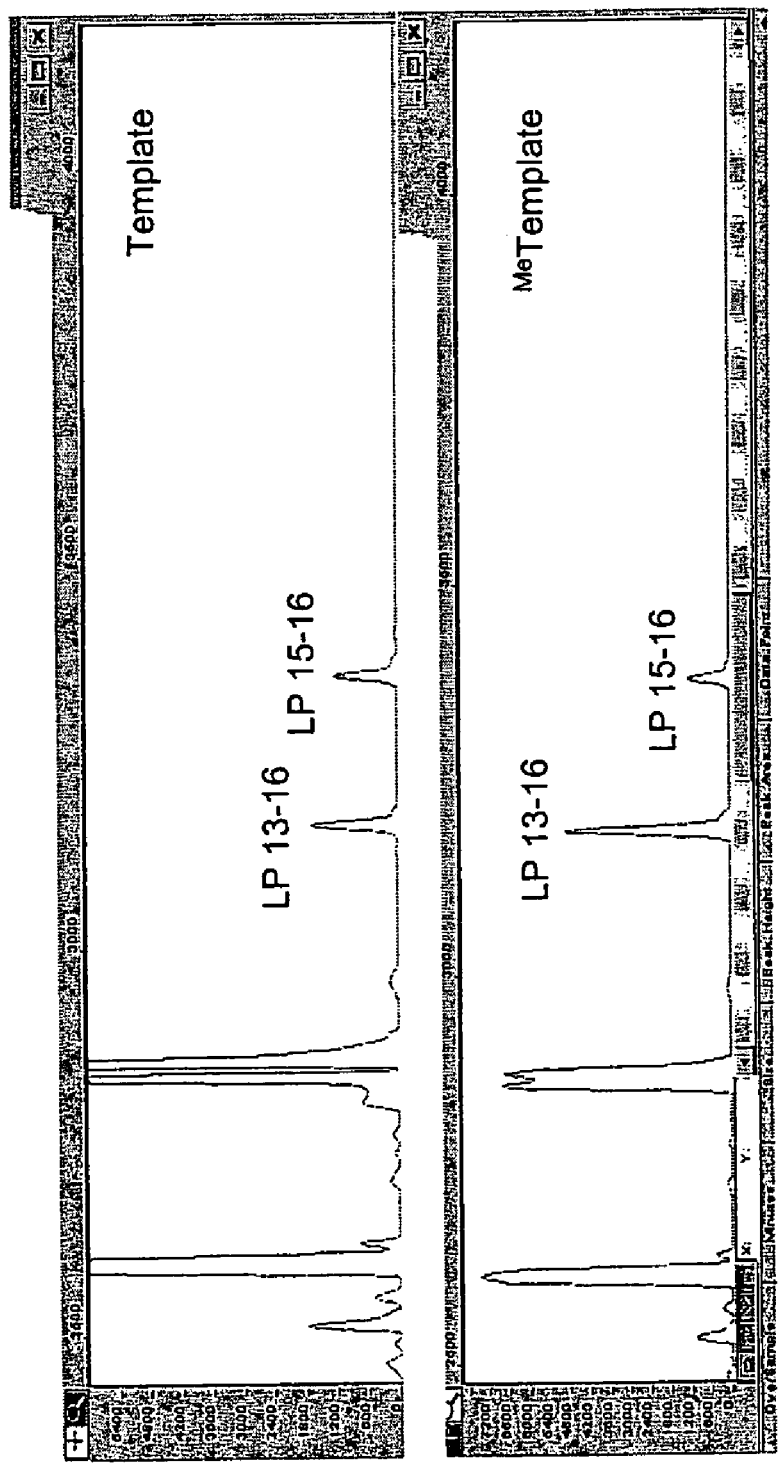
Figure 6C:
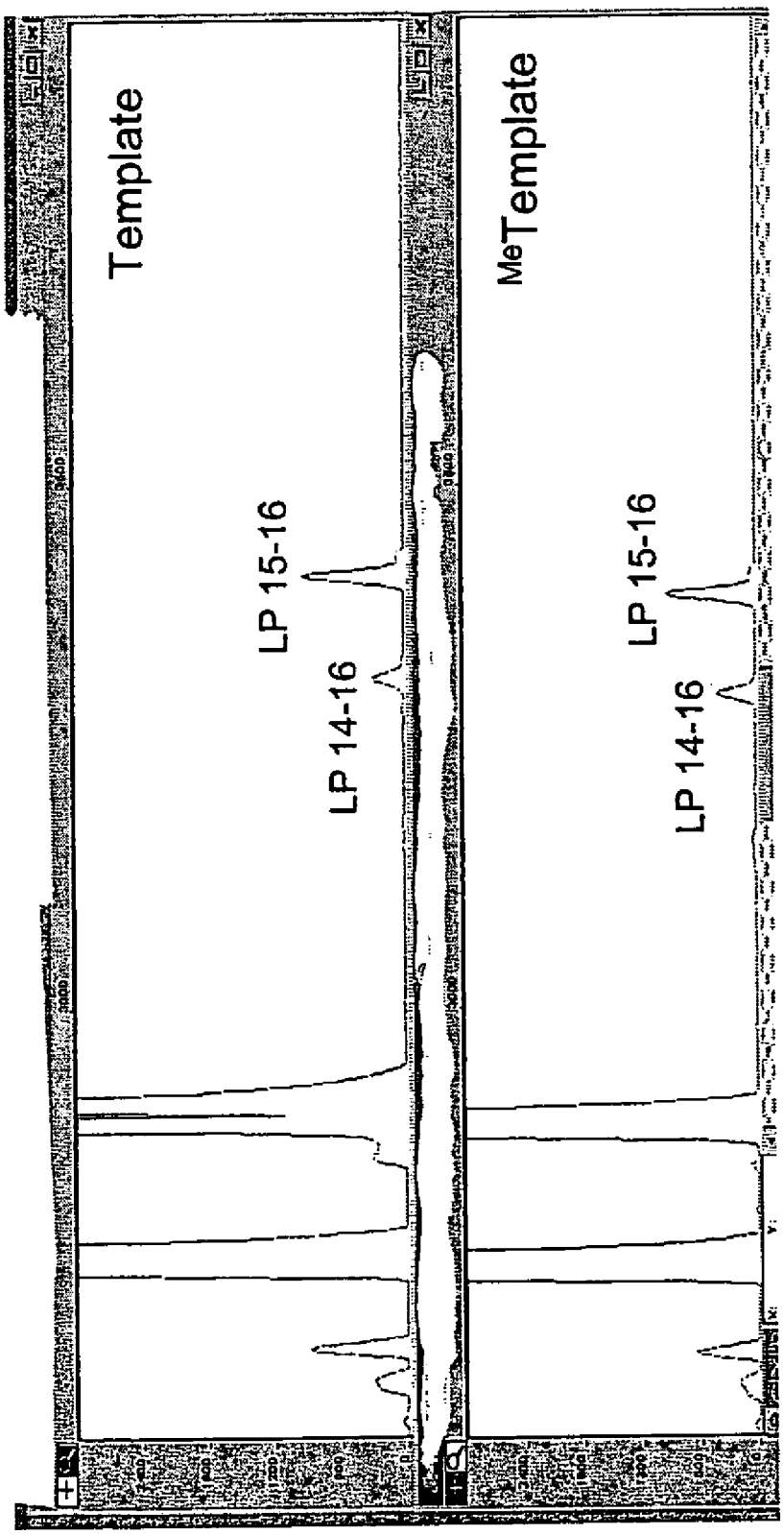

When probes 13 and 14 were used with probe 16 in this competition misligation assay, the ligation product ratio for the ligation product of probes 13 and 16 compared to the ligation product for probes 14 and 16 (LP 13-16/LP 14-16) was 4.28 using the non-methylated template and 12.18 using the methylated template (see FIG. 6A). When probes 13 and 15 were competed, the ligation product ratio (LP 13-16/LP 15-16) was 1.33 using the non-methylated template and 4.06 using the methylated template (see FIG. 6B). When probes 14 and 15 were competed, the ligation product ratio (LP 14-16/LP 15-16) was 0.35 using the non-methylated template and 0.45 using the methylated template (see FIG. 6C).

Example 4

Competing Misligation Assay

A probe set comprising a single base mismatch at the 5' end of each of the downstream probes was prepared for interrogating the target nucleotide in the synthetic methylated or non-methylated E2F2 template, SEQ ID NO:12. The probe set comprised one upstream probe and three downstream probes. The upstream probe comprised the fluorescent reporter group FAM® and the target nucleotide complement (shown underlined), each of the downstream probes

TABLE 3

Probe Set 5

| 5' probes | | 3' probe | |
|---|---|---|---|
| FAM-CACTGCTCTGGCCA<br>probe 13 | (SEQ ID NO:13) | | |
| FAM-(PEO)-CACTGCTCTGGCCC<br>probe 14 | (SEQ ID NO:14) | CCTCTGCACTGTGCAT<br>probe 16 | (SEQ ID NO:16) |
| FAM-(PEO)$_2$-CACTGCTCTGGCCT<br>probe 15 | (SEQ ID NO:15) | | |

In each assay there were at least two upstream probes competing to be misligated to the downstream probe. The ligation reaction composition, reaction conditions, separacomprised a mismatched nucleotide on the 5'-end and polyethylene oxide mobility modifiers, shown as (PEO), (PEO)$_2$, and (PEO)$_3$ in Table 4.

TABLE 4

Probe Set 6

| 5' probes | | 3' probe | |
|---|---|---|---|
| | | ACTCTGCACTGTGCAT-(PEO)<br>probe 21 | (SEQ ID NO:21) |
| FAM-CACTGCTCTGGCCG<br>probe 22 | (SEQ ID NO:22) | GCTCTGCACTGTGCAT-(PEO)$_2$<br>probe 23 | (SEQ ID NO:23) |
| | | TCTCTGCACTGTGCAT-(PEO)$_3$<br>probe 24 | (SEQ ID NO:24) |

Figure 7A:
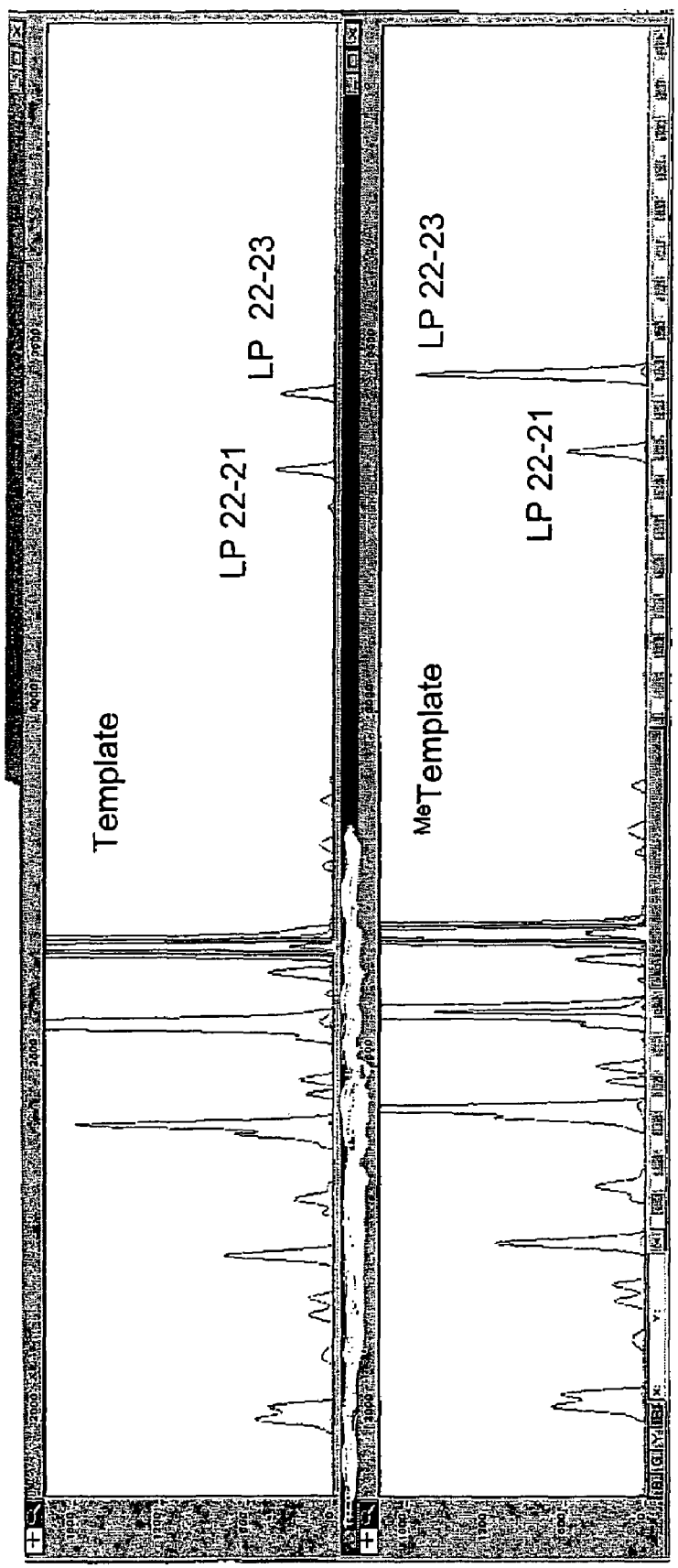
FIGS. 7A-C: Depict electropherograms showing misligation product peaks obtained from an exemplary competitive ligation assay, described in Example 4. The upper panels show the results obtained using a non-methylated synthetic E2F2 template ("Template") and the lower panels show the results obtained when the synthetic E2F2 template comprised 5-methylcytosine as the target nucleotide ("$^{Me}$Template"). The peak corresponding to the misligation product generated using ligation probes 21 and 22 is marked "LP 21-22", the peak corresponding to the misligation product generated using ligation probes 22 and 23 is marked "LP 22-23", the peak corresponding to the misligation product peak generated using ligation probes 22 and 24 is marked "LP 22-24".

Three competition misligation assays (CMAs) were performed in parallel. The first CMA (CMA 1) was performed as follows. A ligation reaction composition comprising 12.5 nM upstream probe 22, 12.5 nM downstream probe 21, 12.5 nM downstream probe 23, 2 units of Afu ligase, and either 0.25 nM methylated E2F2 synthetic template or 0.25 nM non-methylated E2F2 synthetic template was formed in the ligase buffer described in Example 1, in a final volume of 10 µL. This reaction composition was heated to 90° C. for three minutes, then cycled between 90° C. for ten seconds and 50° C. for five minutes, for sixty cycles, heated to 99.9° C. for twenty minutes, then cooled to 4° C. Two microliters of this cooled ligation product composition were combined with 18 µL Hi-Di formamide (Applied Biosystems) and loaded onto an ABI PRISM® 3100 Genetic Analyzer (Applied Biosystems). The remaining reaction conditions, separation, detection and analysis were generally as described in Example 2. As shown in the top panel of FIG. 7A, the peaks detected for the two misligation products (LP 22-21 and LP 22-23) obtained with the template comprising the non-methylated target nucleotide are approximately equal, i.e., the misligation product peak ratio is about 1:1. However, the parallel assay using templates comprising methylated target nucleotides (lower panel) resulted in a misligation product peak ratio of approximately 3:1 (LP 22-23:LP 22-21).

Figure 7B:
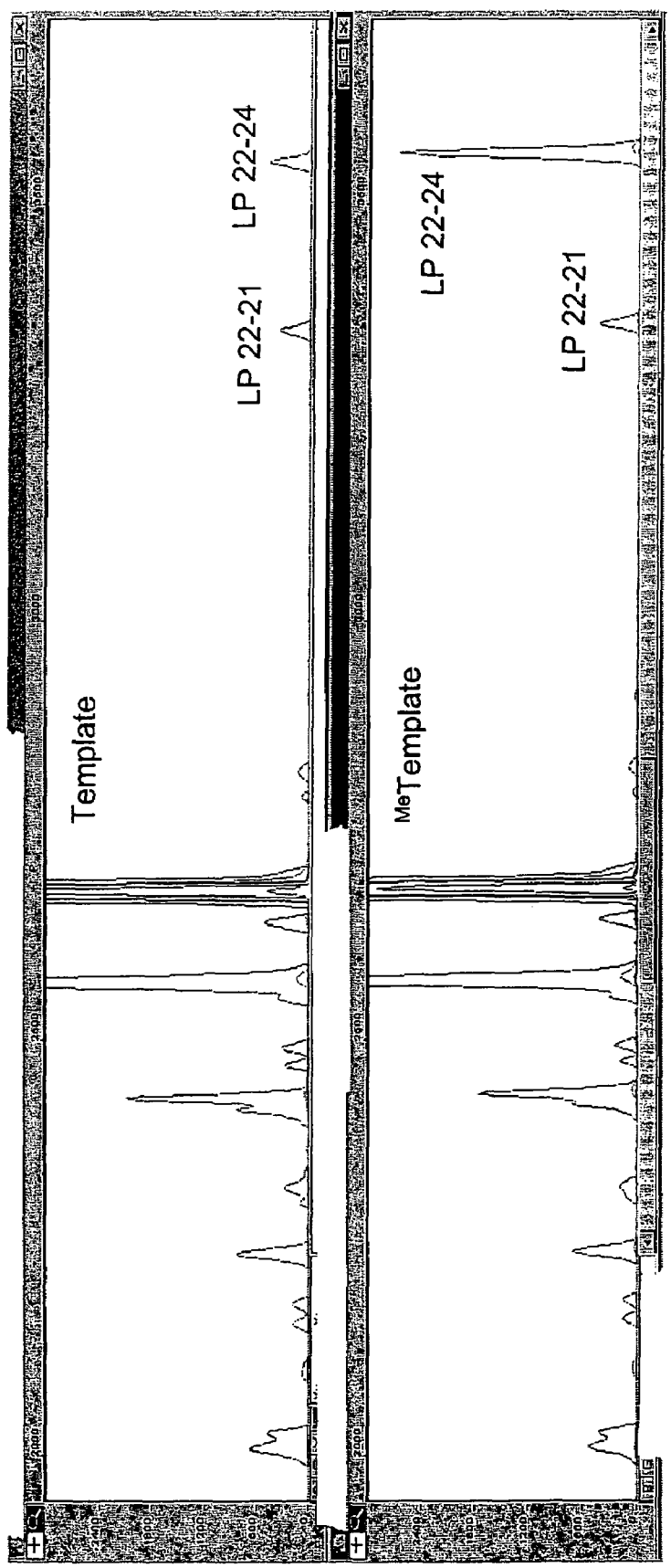

The second CMA was performed in parallel, as described for CMA 1, except that the 12.5 nM downstream probe 24 was used in place of 12.5 nM downstream probe 23 and the two possible misligation products were LP 22-21 and 22-24. As shown in FIG. 7B, the LP 22-24 peak was slightly higher than the LP 22-21 peak with the non-methylated template (top panel). However, the misligation product peak height ratio was approximately 4.5:1 (LP 22-24:LP 22-21) with the methylated template (bottom panel).

Figure 7C:
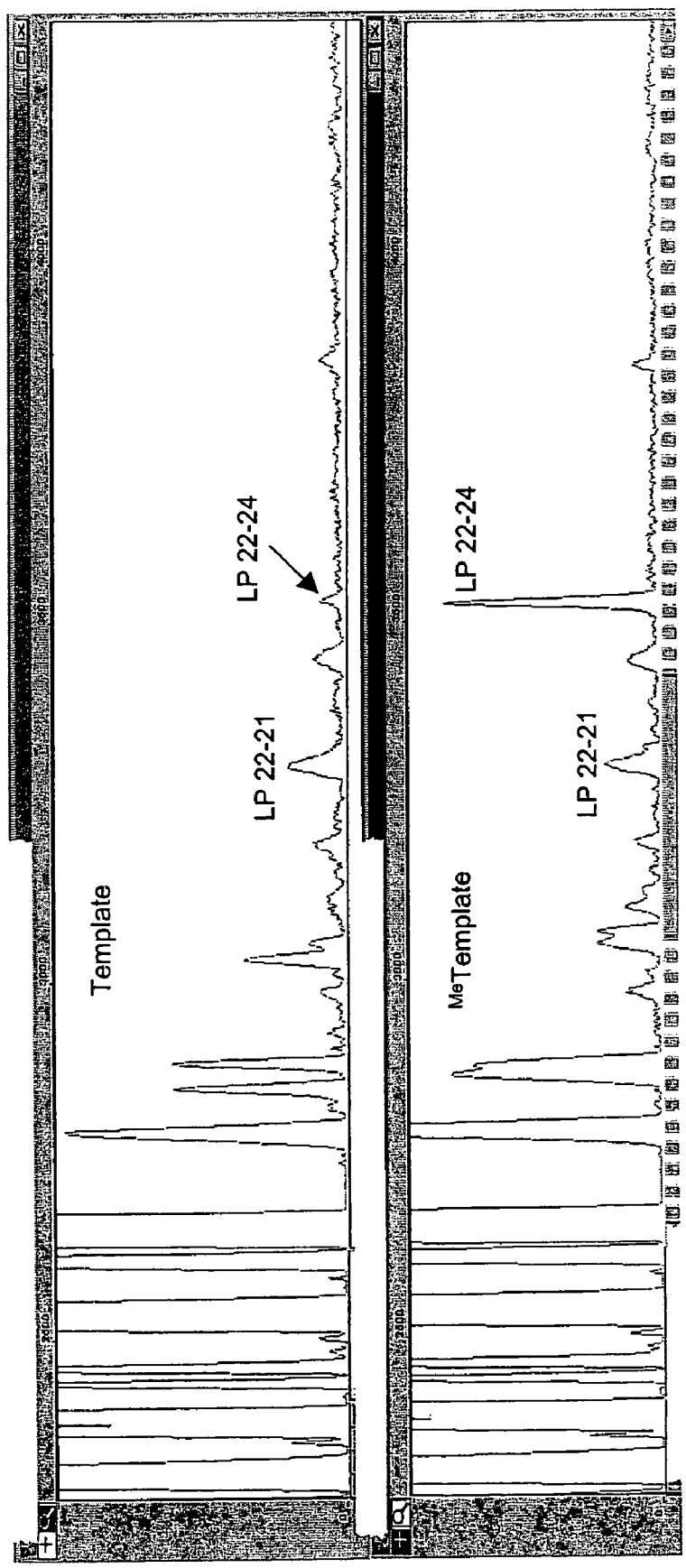

The third CMA (CMA 3) was performed using $10^7$ copies of either the methylated or unmethylated E2F2 synthetic template, 4 units of Afu ligase, upstream probe 22, downstream probes 21 and 24, and cycling conditions of 90° C. for ten seconds, then 50° C. for two and a half minutes for 120 cycles, heated at 99.9° C. for 20 minutes, then cooled to 4° C. All other parameters were as described for CMA 1. As shown in FIG. 7C, the misligation product 22-21 peak (LP 22-21) was several times higher than the misligation product 22-24 peak (LP 22-24) with the template comprising the non-methylated target nucleotide (top panel). With the template comprising the methylated target nucleotide, however, the height of the LP 22-21 peak was essentially unchanged while the height of the LP 22-24 peak was dramatically higher (bottom panel) and the ligation product peak ratio was approximately 4:1 (LP 22-24:LP 22-21). Therefore, under these conditions, each of the competitive misligation assays described in this illustrative embodiment can be used to determine whether the target nucleotide is methylated or not based on the respective misligation product peak ratios.

Further, the methylation state of this exemplary target nucleotide can also be determined by comparing the peak height for LP 22-23 or LP 22-24 using the methylated template with the corresponding peak height obtained using the non-methylated template.

Example 5

Competitive Misligation Assay Using Modified Probes

A probe set comprising three downstream probes, each with a single base mismatch at the 5' end (probes 21, 23, and 24), and a Modified upstream probe (probe 22*) comprising a 2'-methoxy-cytosine Modification (shown as C* in Table 5) and a FAM reporter group was synthesized for interrogating the target nucleotide in the synthetic E2F2 template, SEQ ID NO:12. Probe 22 (shown in Table 4) and probe 22 (shown in Table 5) differ only by the presence (probe 22*) or absence (probe 22) of the 2'-methoxy Modification on the penultimate 3' cytosine residue. The ligation products were separable in mobility dependent analysis techniques based, at least in part, on the complexity of the polyethylene oxide mobility modifiers on the respective ligation products, shown in Table 5 as (PEO), (PEO)$_2$, and (PEO)$_3$ on the downstream probes.

TABLE 5

Probe Set 7

| 5' probes | 3' probe | |
|---|---|---|
| | ACTCTGCACTGTGCAT-(PEO) probe 21 | (SEQ ID NO:21) |
| FAM-CACTGCTCTGGCC*<u>G</u> probe 22* | GCTCTGCACTGTGCAT-(PEO)$_2$ probe 23 | (SEQ ID NO:23) |
| | TCTCTGCACTGTGCAT-(PEO)$_3$ probe 24 | (SEQ ID NO:24) |

Each assay included two competing downstream probes and the upstream probe. The ligation reaction composition, reaction conditions, separation, detection and analysis were generally as described in Example 4.

Figure 8A:
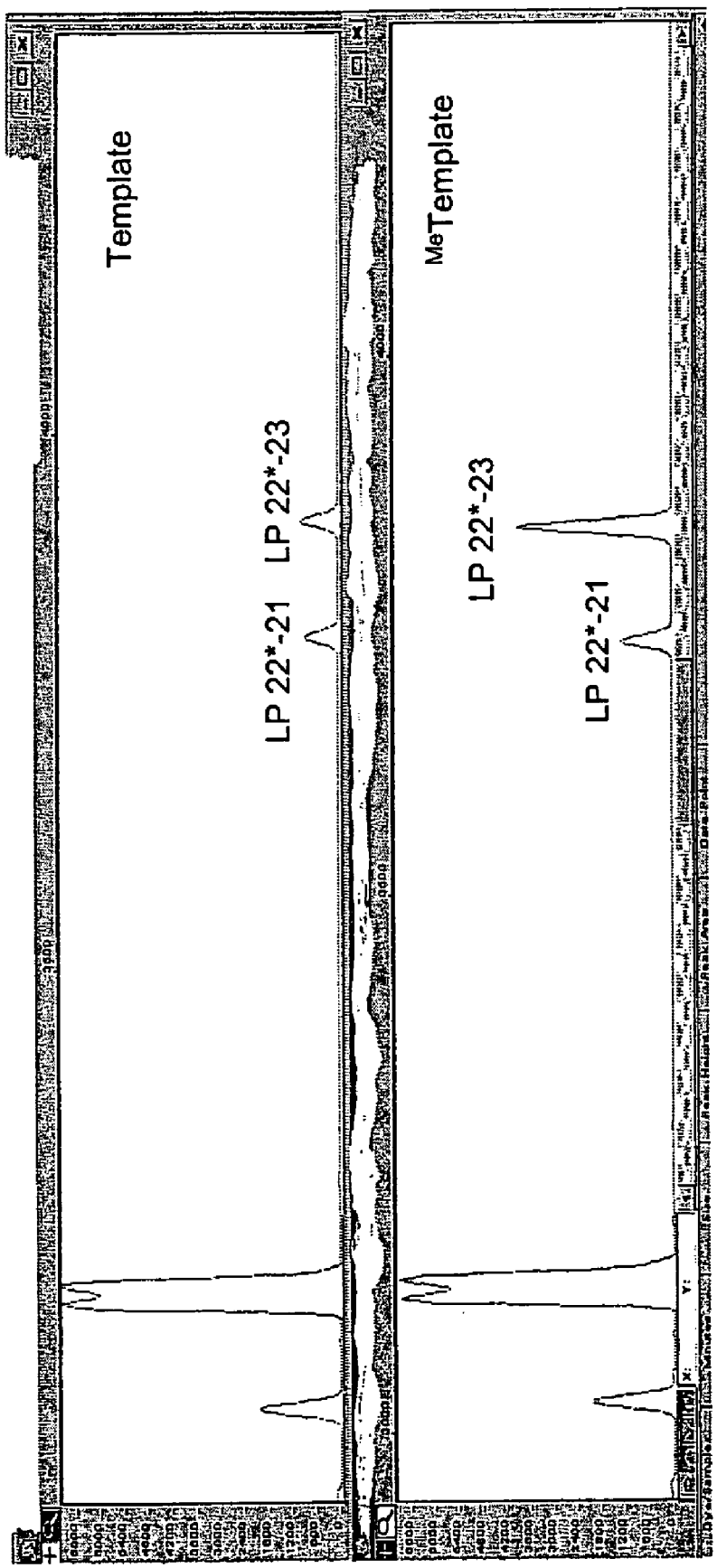
FIGS. 8A-B: Depict electropherograms showing misligation product peaks obtained from an exemplary competitive misligation assay, described in Example 5. The upper panels show the results obtained using a non-methylated synthetic E2F2 template ("Template") and the lower panels show the results obtained when the synthetic E2F2 template comprised 5-methylcytosine as the target nucleotide ("$^{Me}$Template"). The peak corresponding to the misligation product generated using ligation probes 22* and 21 is marked "LP 22*-21", the peak corresponding to the misligation product generated using ligation probes 22* and 23 is marked "LP 22*-23", and the peak corresponding to the misligation product generated using ligation probes 22* and 24 is marked "LP 22*-24".
Figure 8B:
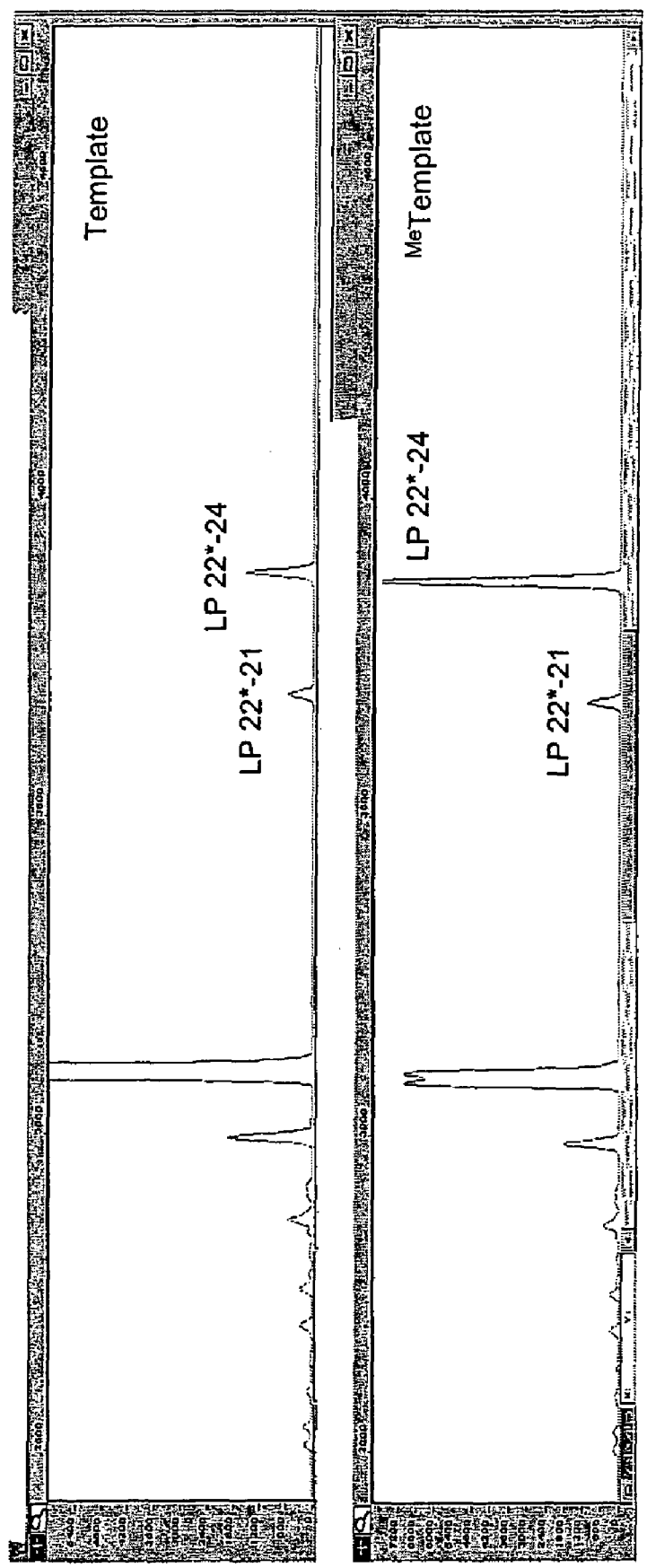

When probes 21 and 23 were used with probe 22* in this competition misligation assay, the ligation product ratio for the ligation product of probes 22* and 23 compared to the ligation product for probes 22* and 23 (LP 22*-23/LP 22*-21) was 1.13 using the synthetic E2F2 template comprising the non-methylated target nucleotide and 3.09 using the methylated template (see FIG. 8A). When probes 21 and 24 were used with probe 22* in this competition misligation assay, the ligation product ratio for the ligation product of probes 22* and 24 compared to the ligation product for probes 22* and 21 (LP 22*-24/LP 22*-21) was 2.69 using the synthetic template comprising the non-methylated target nucleotide and 7.9 using the methylated template (see FIG. 8B).

Example 6

Competing Misligation Assay with Amplification Using gDNA

To evaluate the competing misligation assay for interrogating the same E2F2 target nucleotide in gDNA instead of a synthetic oligonucleotide, non-methylated and methylated human gDNA was obtained from public sources (Coriell Institute for Medical Research, Camden, N.J. and Serologicals Corp. Nocross, Ga., respectively). Due to possible low copy number of a particular target nucleic acid sequence in gDNA an amplification step was included in this exemplary embodiment. A probe set comprising two upstream probes and three downstream probes was synthesized, as shown in Table 6. Each of the probes comprised either a "universal" upstream primer-binding portion or a "universal" downstream primer-binding portion (shown in brackets) and each the downstream probes comprised a mismatched nucleotide on its 5' end. Probes 27 and 28 also included a mobility modifier comprising several non-sequence related nucleotides (underlined) to enhance ligation product separation. The target nucleotide complement was on the 3'-end of the upstream probe (underlined). A Modified version of probe 25 (probe 25*) was synthesized with a 2-methoxy Modification on the penultimate cytosine (shown as C*).

Figure 9A:
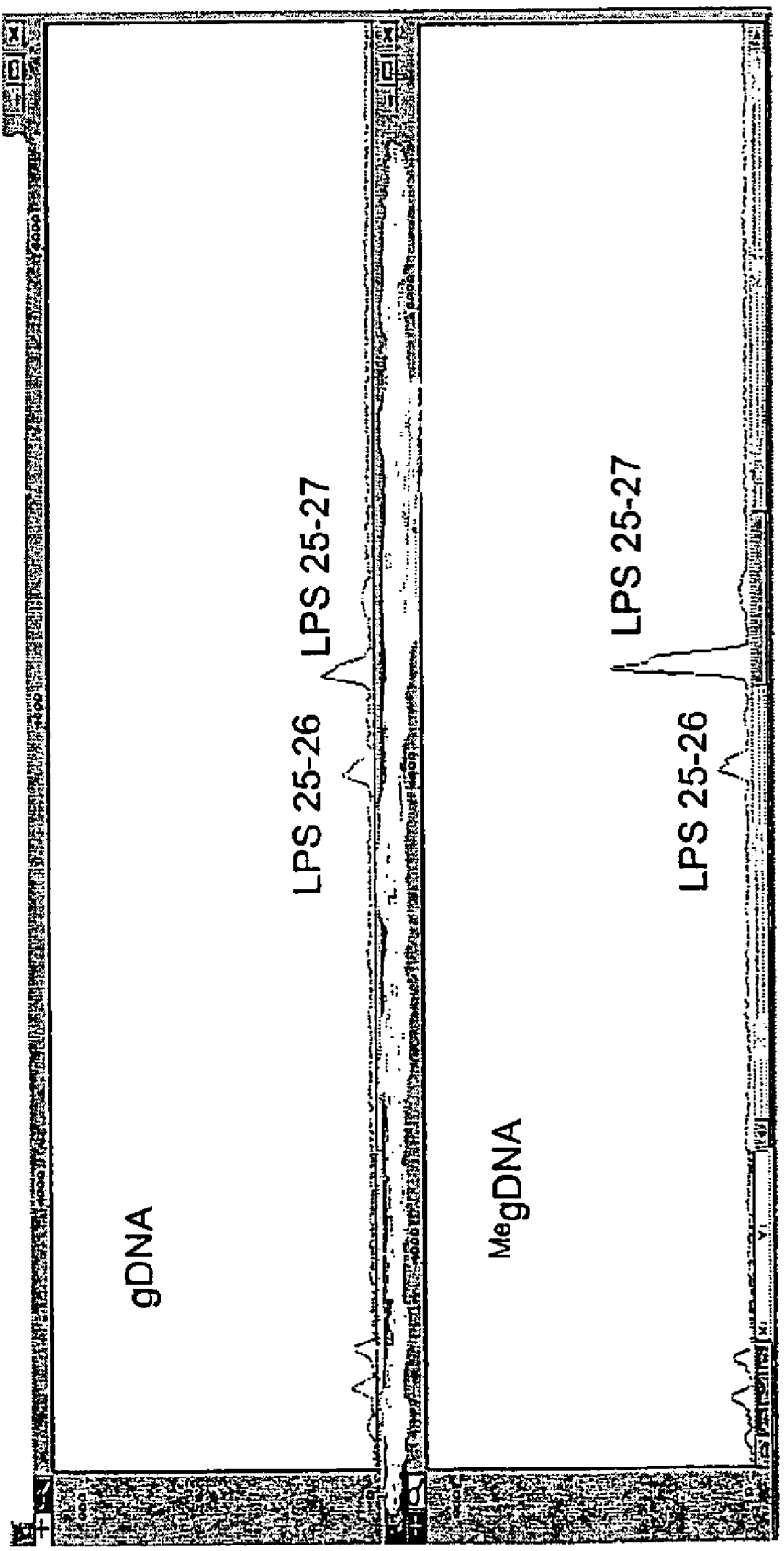
FIGS. 9A-C: Depict electropherograms showing the peaks obtained from an exemplary competitive misligation assay described in Example 6. The upper panel shows the misligation product surrogate peak heights obtained using non-methylated gDNA ("gDNA") and the lower panel shows the misligation product surrogate peak heights obtained using methylated gDNA ("$^{Me}$gDNA"). The detected peak corresponding to the misligation product surrogate generated using ligation probes 25 and 26 is marked "LPS 25-26", the detected peak corresponding to the misligation product surrogate generated using probes 25 and 27 is marked "LP 25-27", and so forth.
Figure 9B:
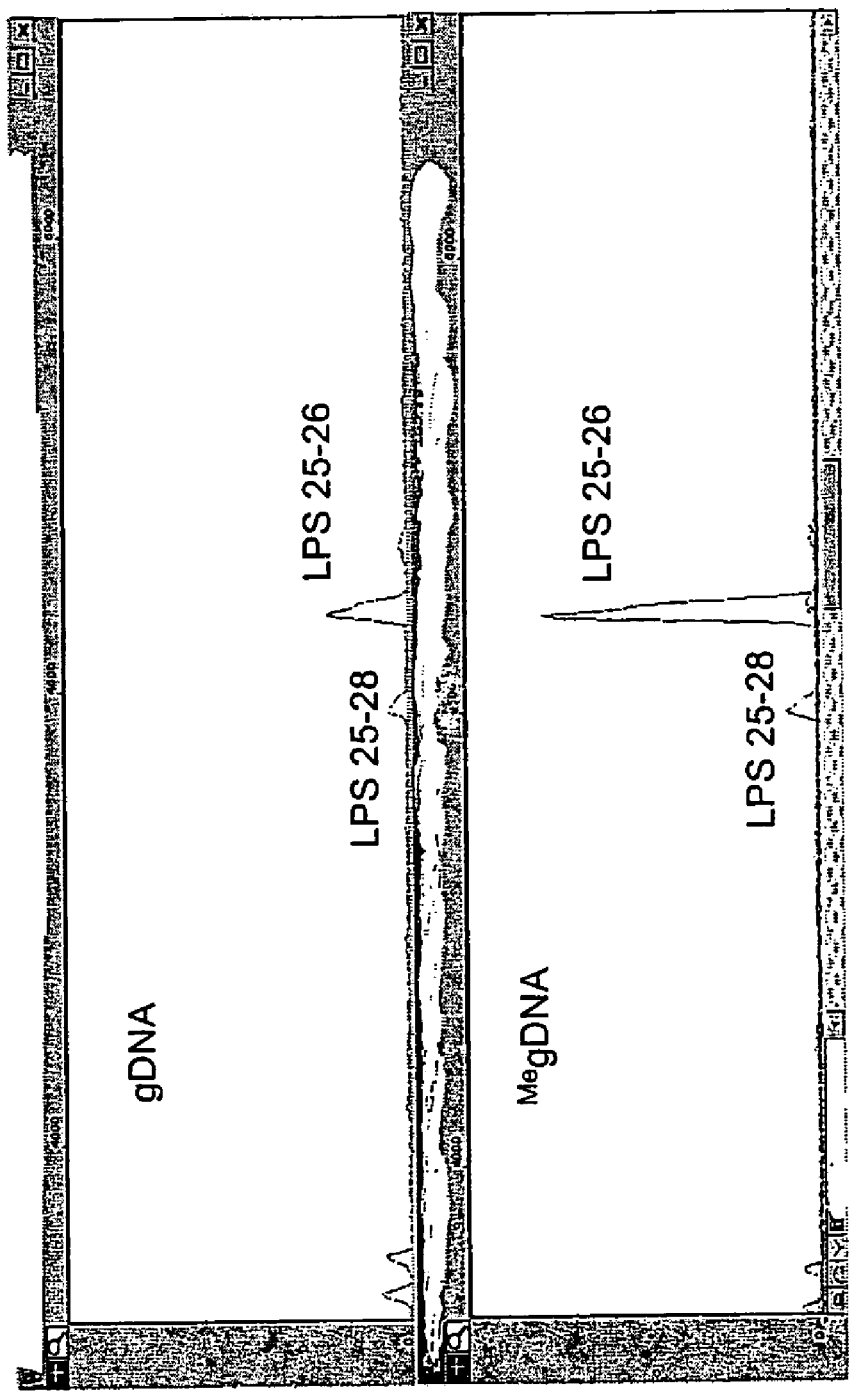

The ligation product ratio, based on the peak area of the misligation product surrogate for the misligation product of probes 25 and 27 (LPS 25-27) compared to the misligation product of probes 25 and 26 (LPS 25-26) was 1.72 when the gDNA comprising the non-methylated target nucleotide was interrogated and 4.37 when the gDNA comprising the methylated target nucleotide was interrogated (see FIG. 9A). The ligation product ratio, based on the peak area of LPS 25-26 compared to that for the misligation product surrogate for the ligation product of probes 25 and 28 (LPS 25-28) was 3.38 when the gDNA comprising the non-methylated target nucleotide was interrogated and 7.24 when the gDNA comprising the methylated target nucleotide was interrogated (see FIG. 9B).

To evaluate the use of Modified probes for methylation determinations using gDNA target nucleic acid sequences, an upstream probe comprising a Modification was prepared by adding a 2'-methoxy Modification to the penultimate

TABLE 6

Probe Set 8

| 5' probes | | 3' probe | |
| --- | --- | --- | --- |
| [CTCGTAGACTGCGTACCGATC]<br>CACTGCTCTGGCC<u>G</u><br>probe 25 | (SEQ ID NO:25) | ACTCTGCACTGTGCAT-<br>[TTACTCAGGACTCATCGTCGC]<br>probe 26 | (SEQ ID NO:26) |
| [CTCGTAGACTGCGTACCGATC]<br>CACTGCTCTGGCC*<u>G</u><br>probe 25* | | GCTCTGCACTGTGCAT<u>TTTT</u><br>[TTACTCAGGACTCATCGTCGC]<br>probe 27 | (SEQ ID NO:27) |
| | | TCTCTGCACTGTGCAT<u>TTTT</u><br>[TTACTCAGGACTCATCGTCGC]<br>probe 28 | (SEQ ID NO:28) |

Two sets of parallel ligation reaction compositions (four reaction compositions) were prepared in a final volume of 10 μL as follows: 25 nanograms (ng) of either (i) methylated or (ii) unmethylated gDNA target nucleic acid sequences; 12.5 nM probe 25; 12.5 nM of other either (iii) probe 26 or (iv) probe 27; and 2-4 units of Afu ligase, all in reaction buffer as described in Example 1. To generate misligation products, the ligation reaction compositions were heated to 90° C. for three minutes, cycled one hundred twenty times between 90° C. for ten seconds and 50° C. for two and a half minutes, heated to 99.9° C. for twenty minutes, then cooled to 4° C.

Amplification reaction compositions were formed by separately combining each of these ligation product compositions with 0.5 units of Taq Gold™ polymerase (Applied Biosystems) and 0.5 μM of each of the universal amplification primers, FAM-CTCGTAGACTGCGTACCGATC (SEQ ID NO:29; FAM: fluorescent reporter group FAM®, Applied Biosystems) and GCGACGATGAGTCCTGAGTAA (SEQ ID NO:30). To generate amplified misligation products, the amplification reaction compositions were then heated to 95° C. for ten minutes, and cycled between 94° C. for ten seconds and 68° C. for one minute for 25-30 cycles, then cooled to 4° C. Two μL of the amplified misligation products were diluted with 18 μL Hi-Di™ formamide. The diluted amplified misligation products were loaded onto an ABI PRISM® 3100 Genetic Analyzer and separated and analyzed, as described in Example 1. By comparing the ratio of the amplified misligation product (i.e., one form of misligation product surrogate) peaks shown in FIGS. 9A and 9B (LPS 25-26, LPS 25-27, and LPS 25-28), one can determine the methylation state of the target nucleotide.

nucleotide of probe 25 (see probe 25* in Table 7). The ligation reaction composition was prepared as previously described in this example except that probe 25* was used in place of probe 25 and downstream probes 27 and 28 were competed against each other. All other aspects of the misligation assay and amplification were the same.

Figure 9C:
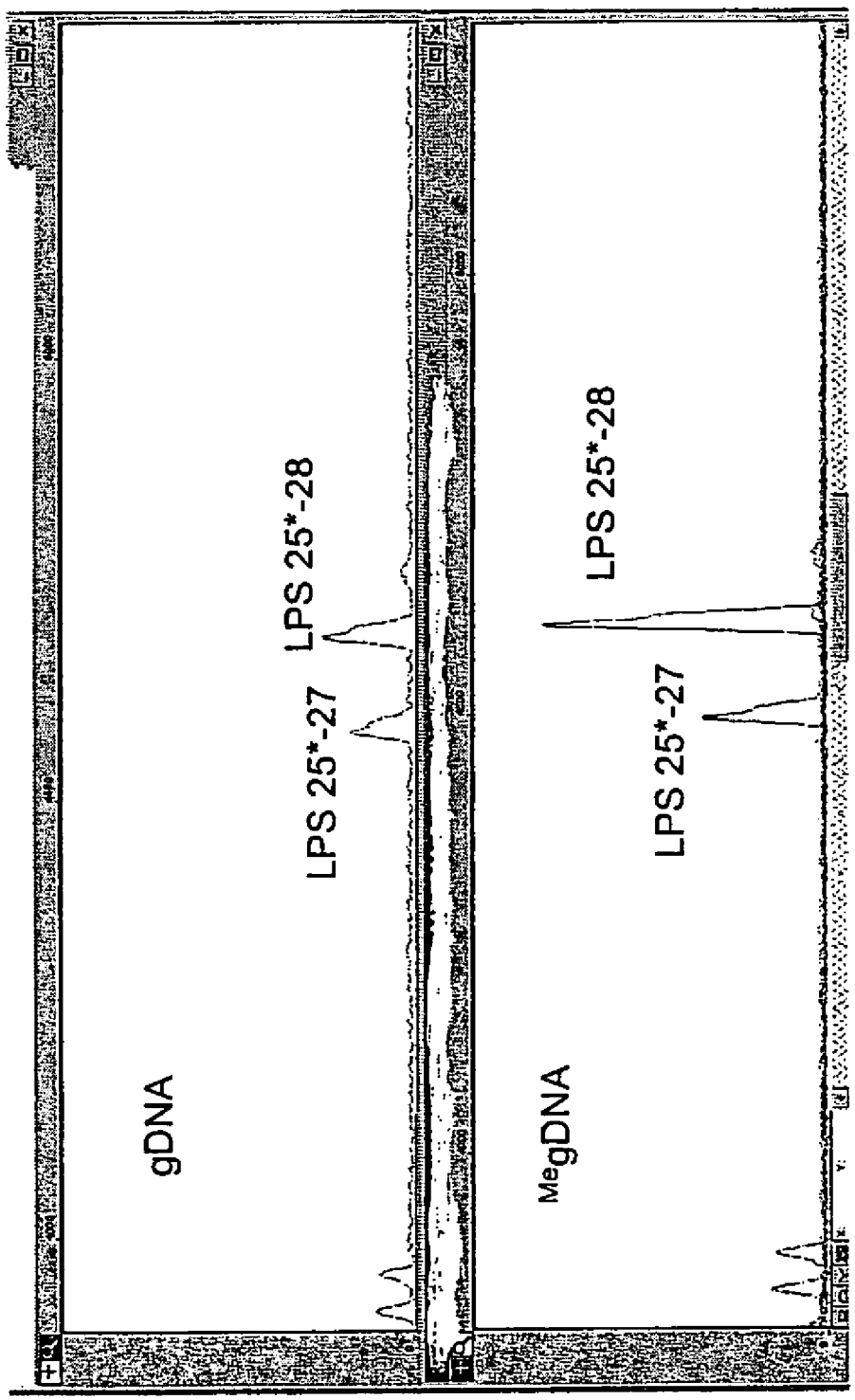

As shown in FIG. 9C, Modified probe 25* also affected the misligation rate, allowing the methylation status of the exemplary target nucleotide to be determined. The ligation product ratio, based on the area under the peak of the misligation product surrogate for the misligation product of probes 25* and 28 (LPS 25*-28) compared to that of the misligation product surrogate for the misligation product of probes 25* and 27 (LPS 25*-27) was 1.41 with the gDNA comprising the non-methylated target nucleotide and 2.24 with the gDNA comprising the methylated target nucleotide (see FIG. 9C).

Example 7

Competing Misligation Assay with Amplification Using gDNA

A second competing misligation assay followed by digestion and amplification was performed to determine the methylation status of the same E2F2 target nucleotide in gDNA as in Example 6. Two ligation reaction compositions were formed as described in Example 6 except that probes 31, 32, and 25 were combined in one ligation reaction composition and probes 31, 33, and 25 were combined in the other. As shown in Table 7, probes 31, 32, and 33 each comprise a universal downstream primer-binding portion (shown in brackets), one of two hybridization tags (shown in italics), and a mismatched nucleotide at the 5'-end of the probe. Probes 25 and 25* contain a universal upstream primer-binding portion (shown in brackets) and the target nucleotide complement at the 3'-end (underlined).

ZipChute solution was prepared by combining 6.576 mL 7.3× ZipChute dilution buffer, 5.40 mL omnipure formamide, and 0.024 mL of 250 nM ZipChute stock solution (Applied Biosystems). Twenty-five µL ZipChute solution was added to the wells and the plate was incubated at 37° C. After one hour, the wells were emptied, washed four times

TABLE 7

Probe Set 9

| 5' probe | 3' probes | |
|---|---|---|
| [CTCGTAGACTGCTACCGATC]<br>CACTGCTCTGGCCG<br>probe 25 | ACTCTGCACTGTGCAT-<br>TCGCAGATTGTGTCTCACCGAGGA-<br>[TTACTCAGGACTCATCGTCGC]<br>probe 31 | (SEQ ID NO:31) |
| [CTCGTAGACTGCTACCGATC]<br>CACTGCTCTGGCC*G<br>probe 25* | GCTCTGCACTGTGCAT-<br>CGATTCAAACTGAAGCGTGCCGACG-<br>[TTACTCAGGACTCATCGTCGC]<br>probe 32 | (SEQ ID NO:32) |
| | TCTCTGCACTGTGCAT-<br>CGATTCAAACTGAAGCGTGCCGACG-<br>[TTACTCAGGACTCATCGTCGC]<br>probe 33 | (SEQ ID NO:33) |

The misligation products were generated as described in Example 6, except downstream probes 31, 32, and 33 were used. Each of these misligation product compositions were then digested with exonuclease by combining five µL of ligation reaction composition with five µL of exonuclease solution (0.2 µL λ exonuclease (1 Unit; New England BioLabs), 0.5 µL 10×λ exonuclease buffer (New England Biolabs)., 4.3 µL distilled water). To generate digested misligation products, the two digestion compositions were heated to 37° C. for ninety minutes, then heated to 80° C. for ten minutes. Each of the digested misligation product compositions were diluted by adding 15 µL of distilled water.

Digested amplification reaction compositions were formed by combining 2.08 µL of the diluted digested misligation product composition with 7.92 µL PCR premix (0.5 Units AmpliTaq Gold™ DNA Polymerase (Applied Biosystems), 50 nM Tris-HCl, pH 8.0 at 25° C., 2.5 mM MgCl₂, 0.01% sodium azide, 0.01% Tween 20, 8% glycerol (v/v), 0.1 mM deferoxamine mesylate, 0.2 mM dATP, 0.2 mM dCTP, 0.2 mM dGTP, 0.2 mM dUTP and 0.5 µM each of biotin-CTCGTAGACTGCGTACCGATC (SEQ ID NO:34) comprising a biotin moiety at its 5'-end, and GCGACGAT-GAGTCCTGAGTAA (SEQ ID NO:35)). To generate digested amplified misligation products, the digested amplification reaction compositions were heated to 95° C. for ten minutes, then cycled between 94° C. for ten seconds and 68° C. for one minute for 25-30 cycles to generate double-stranded amplicons comprising one biotinylated strand (i.e., a form of misligation product surrogate).

The wells of a streptavidin plate (Roche Bioscience) were washed three times with 25 µL Wash Buffer (¹/₁₀ dilution of 1×SSC, 0.1% Tween 20). One part of the biotinylated amplicons was diluted in seven parts hybridization buffer (1×SSC, 0.01% Tween 20) to form a hybridization mix. Twenty µL of this hybridization mix was added to wells of the washed streptavidin plate and incubated at room temperature on an orbital shaker. After a 30 minute incubation, the liquid in each well was removed and the wells were washed three times with 30 µL Wash Buffer. Fifty µL of 0.1 N NaOH was added to the wells and the plate was incubated at room temperature on an orbital shaker. After five minutes, the wells were emptied then washed five times with 50 µL Wash Buffer.

with 25 µL Wash Buffer, then spin dried. Next, 17.5 µL SNPlex loading reagent (Applied Biosystems) was added to the individual wells and the plate was incubated at 37° C. to release the ZipChutes (i.e., a form of (mis)ligation product surrogate) from the wells of the plate into the loading reagent. After a thirty minute incubation, ten µL of the loading reagent comprising released ZipChutes from individual wells of the streptavidin plates were transferred to individual wells of a 384 well plate. These samples were analyzed on an ABI PRISM® 3100 Genetic Analyzer, essentially as described above.

Figure 10A:
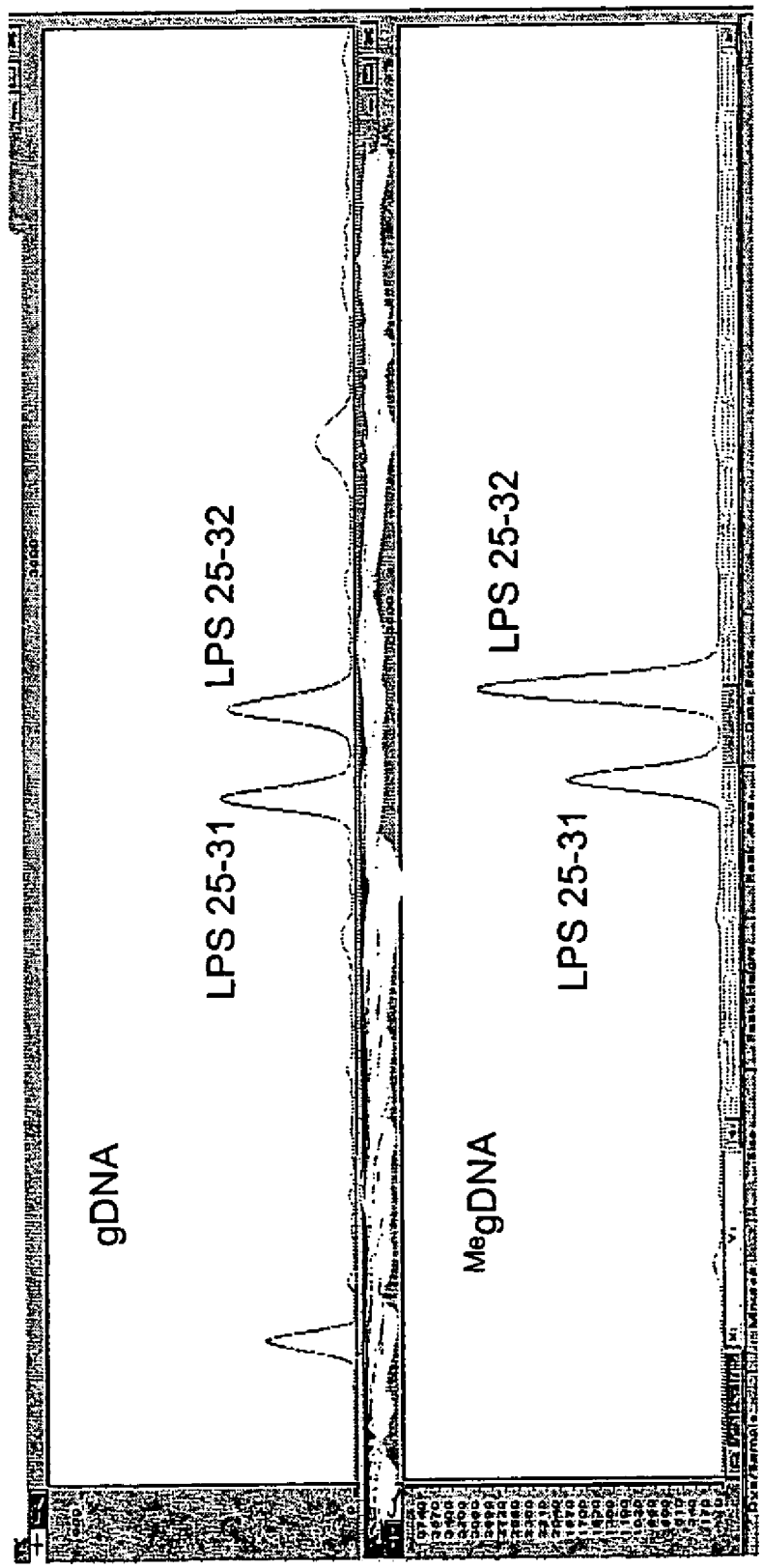
FIGS. 10A-C: Depicts electropherograms showing the peaks obtained from an exemplary competitive misligation assay described in Example 7. The upper panels show the peaks obtained using "gDNA" and the lower panels show the peaks obtained using "$^{Me}$gDNA". The detected peak corresponding to the misligation product surrogate generated using probes 25 and 31 is marked "LPS 25-31", the detected peak corresponding to the misligation product surrogate generated using probes 25 and 32 is marked "LP 25-32", and so forth.
Figure 10B:
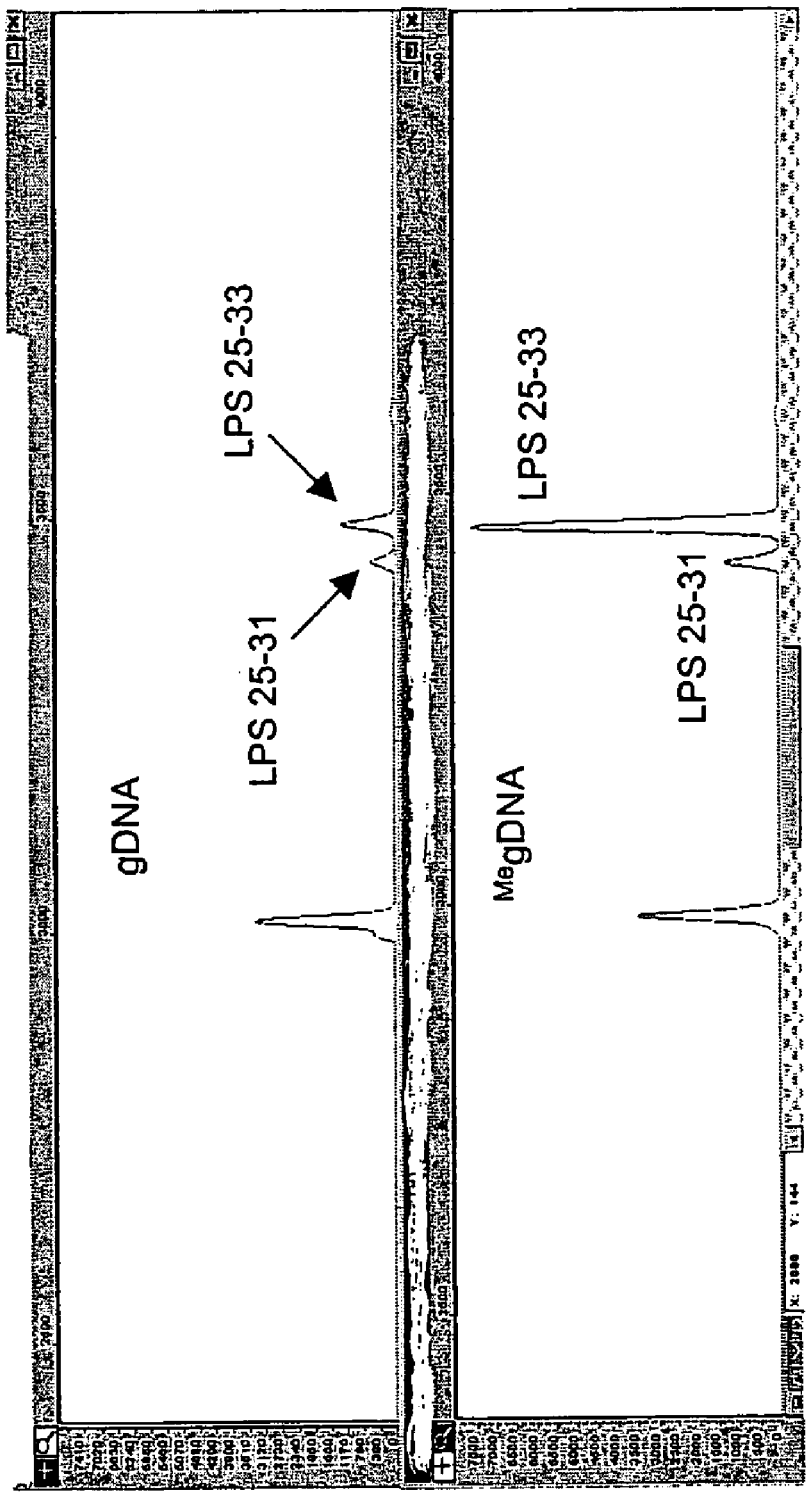
Figure 10C:
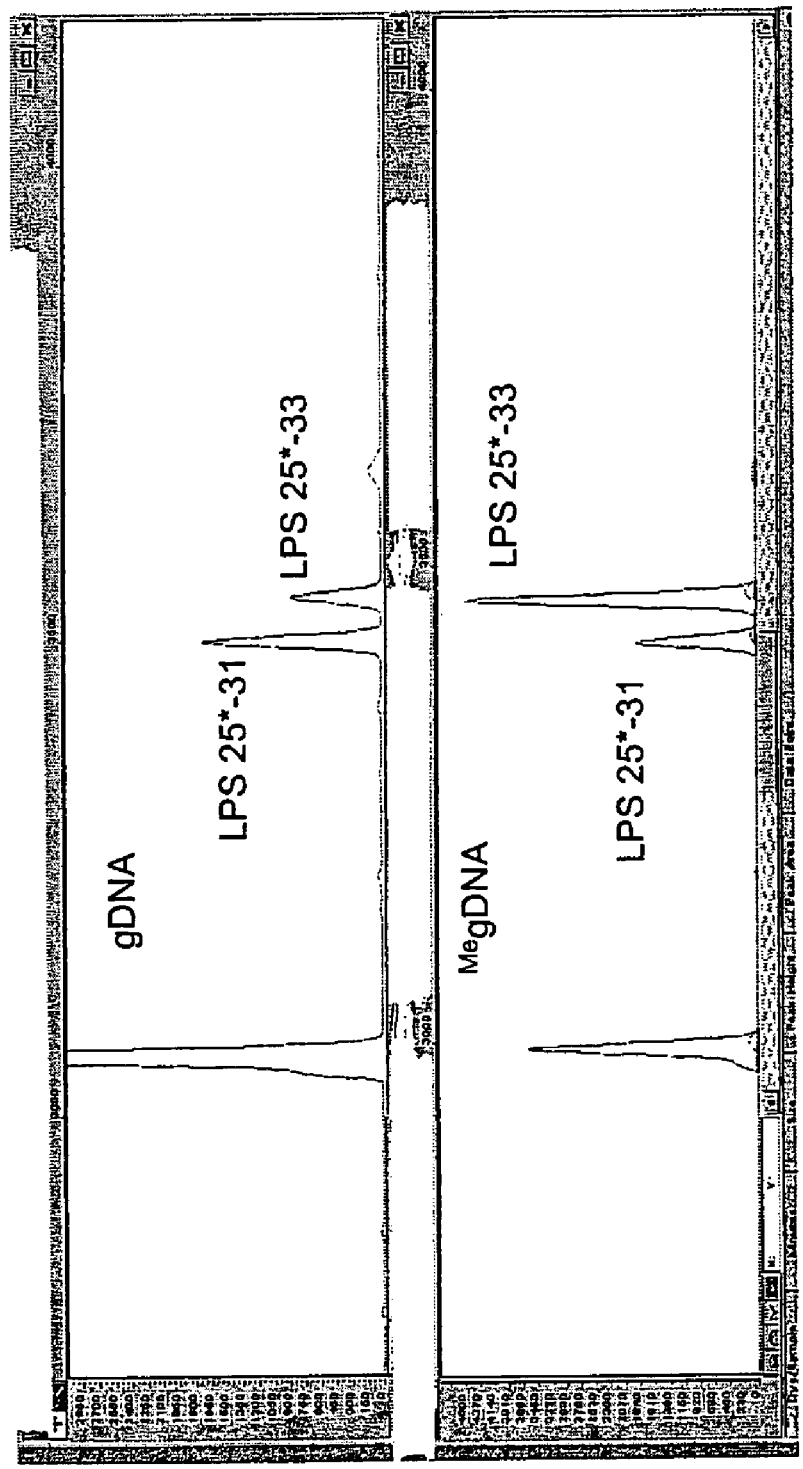

As shown in FIG. 10A, the LPS 25-32:LPS 25-31 peak area ratio was 0.95 with the non-methylated gDNA and 1.66 with methylated gDNA. The LPS 25-33:LPS 25-31 peak area ratio was 2.31 with the non-methylated gDNA and 6.22 with methylated gDNA (see FIG. 10B). The LPS 25*-33: LPS 25*-31 peak area ratio was 0.53 with the non-methylated gDNA and 2.49 with methylated gDNA (see FIG. 10C).

Example 8

Competing Misligation Assay with Amplification Using gDNA

To evaluate the competing misligation assay with the P16 target nucleotide shown in SEQ ID NO:17 in the context of gDNA, three parallel ligation reaction compositions were formed as described in Example 7 except that probes 36, 37 and 38 were combined in a first ligation reaction composition, probes 36, 37, and 40 were combined in a second ligation reaction composition, and probes 37, 39, and 40 were combined in a third ligation reaction composition. As shown in Table 8, probes 36, 38, 39, and 40 each comprise a universal upstream primer-binding portion (shown in brackets), one of two hybridization tags (shown in italics), and a mismatched nucleotide at the 3'-end of the probe. Probe 37 contains a universal downstream primer-binding portion (shown in brackets) and the target nucleotide complement at its 5'-end (underlined).

TABLE 8

Probe Set 10

| 5' probes | | 3'probe | |
|---|---|---|---|
| [CTCGTAGACTGCGTACCGATC]<br>TCCTCGGTGAGACACAATCTGCGA<br>AGCGCACTCA<br>probe 36 | (SEQ ID NO:36) | GTCCGCCCCAC[TTACT<br>CAGGACTCATCGTCGC]<br>probe 37 | (SEQ ID NO:37) |
| [CTCGTAGACTGCGTACCGATC]<br>CGTCGGCACGCTTCAGTTTGAATCG<br>AGCGCACTCC<br>probe 38 | (SEQ ID NO:38) | | |
| [CTCGTAGACTGCGTACCGATC]<br>TCCTCGGTGAGACACAATCTGCGA<br>AGCGCACTCC<br>probe 39 | (SEQ ID NO:39) | | |
| [CTCGTAGACTGCGTACCGATC]<br>CGTCGGCACGCTTCAGTTTGAATCG<br>AGCGCACTCT<br>probe 40 | (SEQ ID NO:20) | | |

Figure 11A:
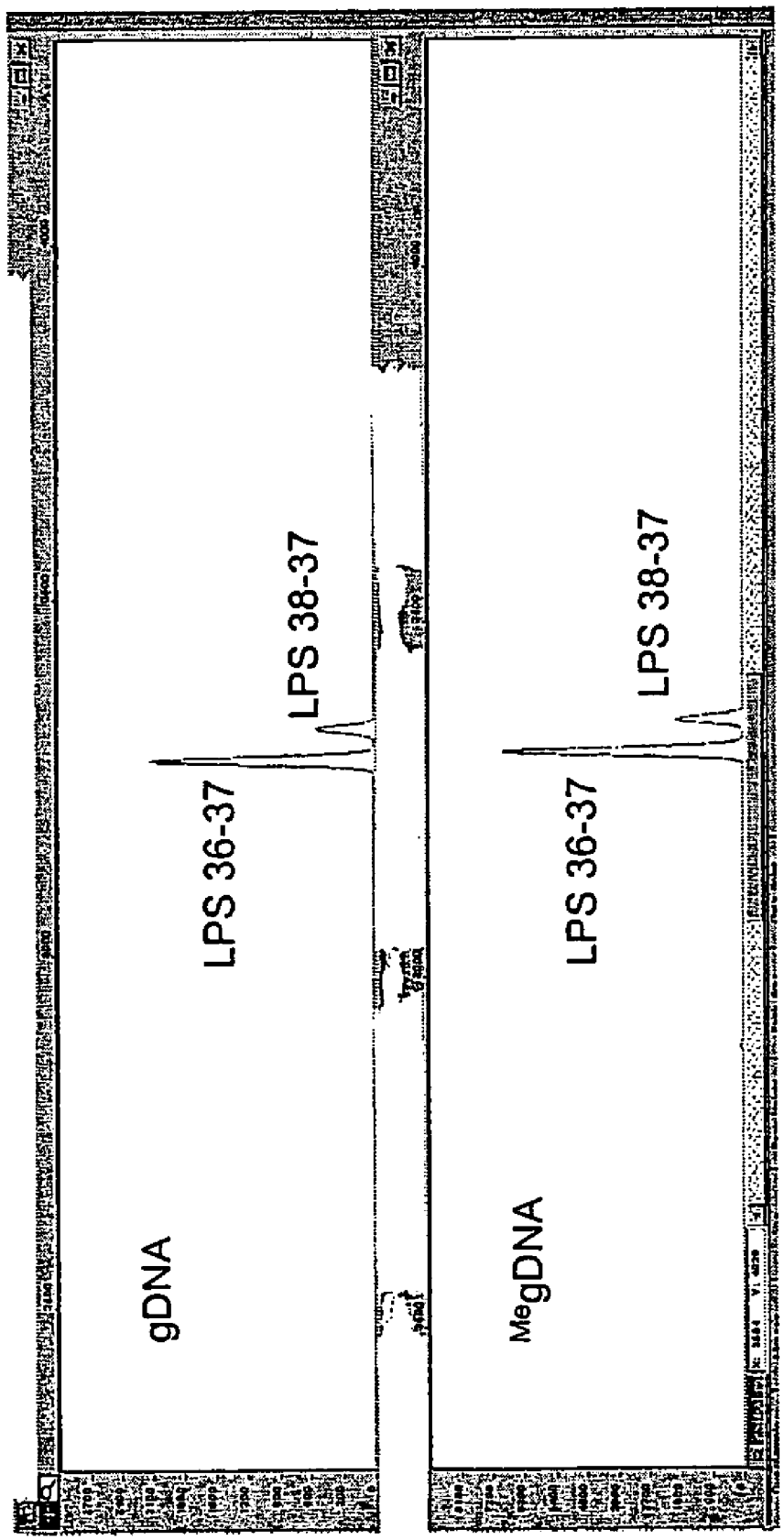
FIGS. 11A-C: Depict electropherograms showing the peaks obtained from an exemplary competitive misligation assay described in Example 8. The upper panels show the peaks obtained using gDNA and the lower panels show the peaks obtained using methylated gDNA ($^{Me}$gDNA). The detected peak corresponding to the misligation product surrogates generated using probes 36 and 37 is marked "LPS 36-37"; the detected peak corresponding to misligation product surrogate generated using probes 38 and 37 is marked "LP 38-37", and so forth.
Figure 11B:
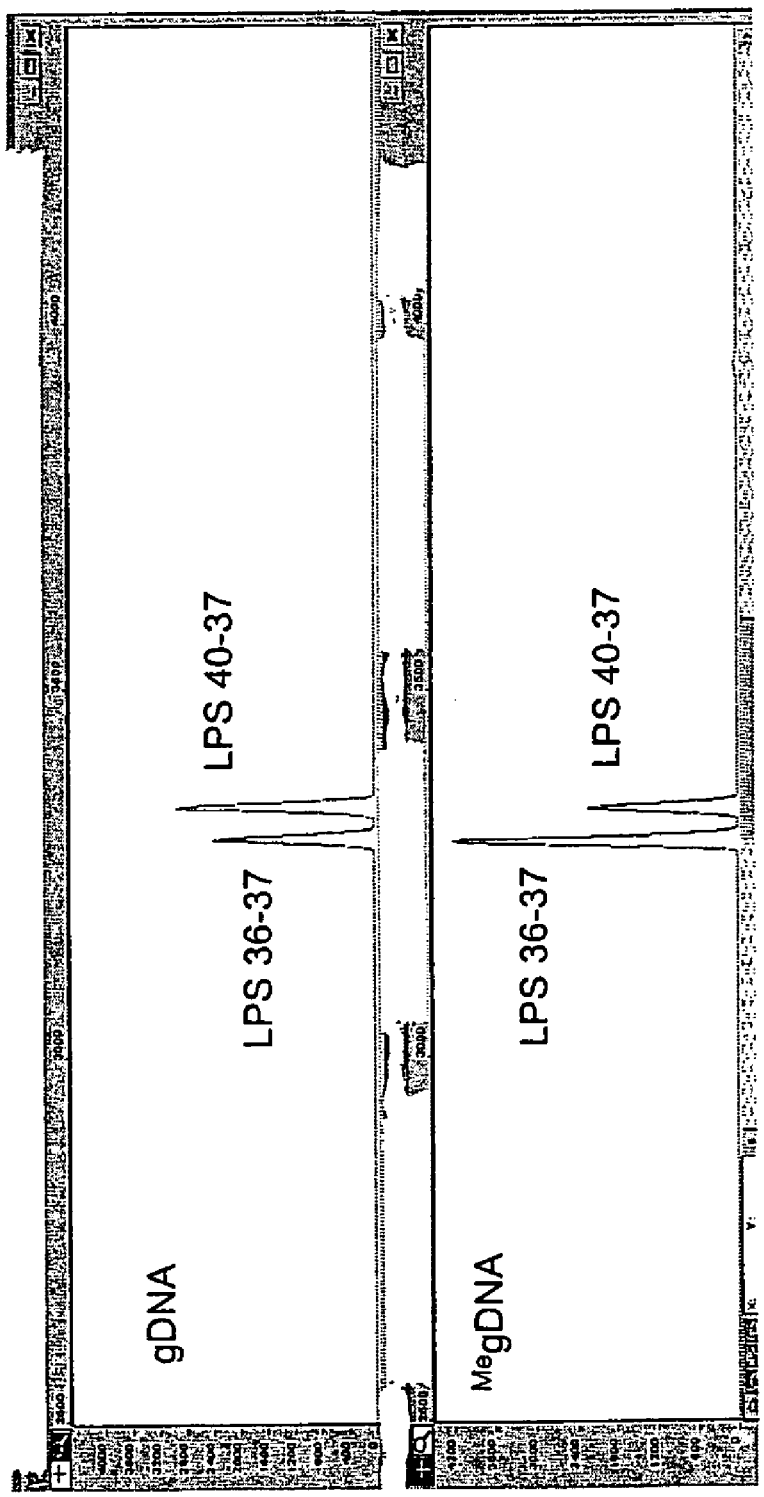
Figure 11C:
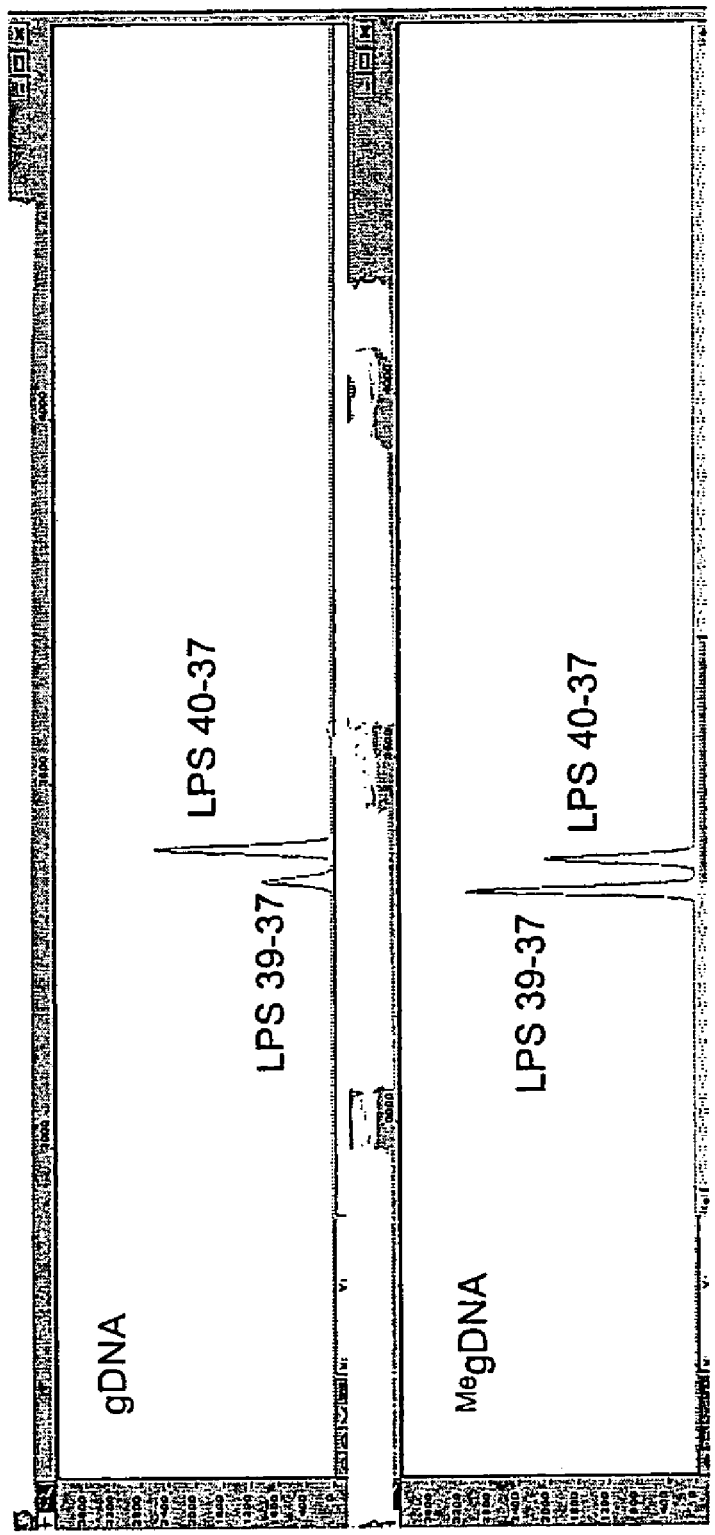

The remainder of the misligation assay, digestion, amplification, separation, detection and determination were performed as described in Example 6, except that the primers used were biotin-GCGACGATGAGTCCTGAGTAA (SEQ ID NO:18) and CTCGTAGACTGCGTACCGATC (SEQ ID NO:19). As shown in FIG. 11A, the digested amplified misligation product (i.e., a form of misligation product surrogate) peak height ratios obtained from the first ligation product reaction composition (LPS 36-37:LPS 38-37) shows little to no change between the methylated and non-methylated target. As shown in FIG. 11B, the ligation product surrogate peak height ratio obtained from the second ligation reaction composition for the non-methylated template is approximately 3:4 (LPS 36-37:LPS 40-37), but shifts to 4:2 (LPS 36-37:LPS 40-37) with the methylated gDNA. The misligation product surrogate peak height ratios for the third ligation reaction composition also varied between the non-methylated and methylated gDNA, as shown in FIG. 11C. With the non-methylated gDNA (upper panel), the ligation product surrogate peak height ratio was approximately 1:3 (LPS 39-37:LPS 40-37), while it was approximately 3:2 (LPS 39-37:LPS 40-37) with the methylated gDNA (lower panel). Thus, under these conditions, the competing probes used in the second and third of these misligation assays are useful in determining the methylation of the illustrative P16 target nucleotide in gDNA while those used in the first reaction composition of this example were less effective. As the person in the art appreciates, identification of useful probes and probe sets can be determined through routine evaluation using the disclosed teachings and without undue experimentation.

Example 9

Generating a Standard Curve

One way to determine the degree of target nucleotide methylation is to compare the experimental results obtained according to the present teachings with a corresponding standard curve. A standard curve can be generated by combining at least one upstream probe and at least one corresponding downstream probe from a probe set with a target comprising a pre-determined mixture of methylated and non-methylated target nucleic acid sequences. For example, for each of the ligation reaction compositions of Example 8, six parallel compositions are prepared with the gDNA target comprising: (i) 25 ng methylated gDNA, (ii) 20 ng methylated gDNA and 5 ng non-methylated gDNA, (iii) 15 ng methylated gDNA and 10 ng non-methylated gDNA, (iv) 10 ng methylated gDNA and 15 ng non-methylated gDNA, (v) 5 ng methylated gDNA and 20 ng non-methylated gDNA, or (vi) 25 ng non-methylated gDNA, respectively. The remainder of the reaction conditions and techniques are as described in Example 8.

For each of the possible (mis)ligation products in each set of ligation reaction compositions, e.g., LP 36-37 and LP 38-37, there are six (mis)ligation product peak height ratios corresponding to 0, 20, 40, 60, 80 and 100% methylated target (or vice versa). A plot of, for example, percent methylation versus (mis)ligation product peak ratio is generated and the data points fit to a curve, i.e., a "standard curve" for the probes tested. Using this standard curve, one can determine the degree of target nucleotide methylation in an unknown sample by locating the experimentally determined (mis)ligation product peak ratio at the appropriate point on the curve and identifying the corresponding degree of methylation, provided that the same probes and assay conditions are used for creating the standard curve and obtaining the unknown sample's ligation product ratio. Those skilled in the art understand that the reliability of standard curves is improved by, among other things, increasing the number of data points used to generate the "curve" and the number of replicates obtained for each data point. Those in the art also understand that standard curves can be generated using any or a number of measurable parameters, not just (mis)ligation product peak height. For example but without limitation, peak height and peak area may be routinely determined using software such as GeneScan™ or GeneMapper™ software and provided as part of a system printout or graphic display.

Example 10

Evaluating the Methylation Detection Potential of Four Ligases

The methylation detection potential of Afu, AK16D, Taq, and Tth ligases were evaluated in a series of ligation assays using probe sets 1, 2, and 3 (shown in Table 1) with either the methylated or the unmethylated synthetic model template, SEQ ID NO:1. Each 20 μL ligation reaction composition comprised 4 Units of ligase (Afu, AK16D, Taq, or Tth), 12.5 nM template (either methylated or unmethylated SEQ ID NO:1), and 12.5 nM of each of the six probes from probe sets 1-3 in 1× ligase buffer (for Afu ligase: 50 mM Tris-HCl, pH 7.5, 10 mM MgCl$_2$, 10 mM dithiothreitol (DTT), 1 mM ATP, 25 μg/ml bovine serum albumin; for AK16D, Taq, and Tth ligases: 20 mM Tris-HCl, pH 7.6, 25 mM potassium acetate, 10 mM magnesium acetate, 10 mM DTT, 1 mM NAD, 0.1% Triton X-100). Ligation products were generated by heating the ligation reaction compositions at 85° C. for 3 minutes, cycling twenty-five times at (85° C. for five seconds, 40° C. for 2 minutes), heating at 95° C. for ten minutes, then cooled to 4° C. Two μL of the ligation products were diluted in 18 μL Hi-Di™ formamide, then the diluted (mis)ligation products were loaded onto capillaries and separated on the ABI PRISM® 3100 Genetic Analyzer, as described.

Figure 12A:
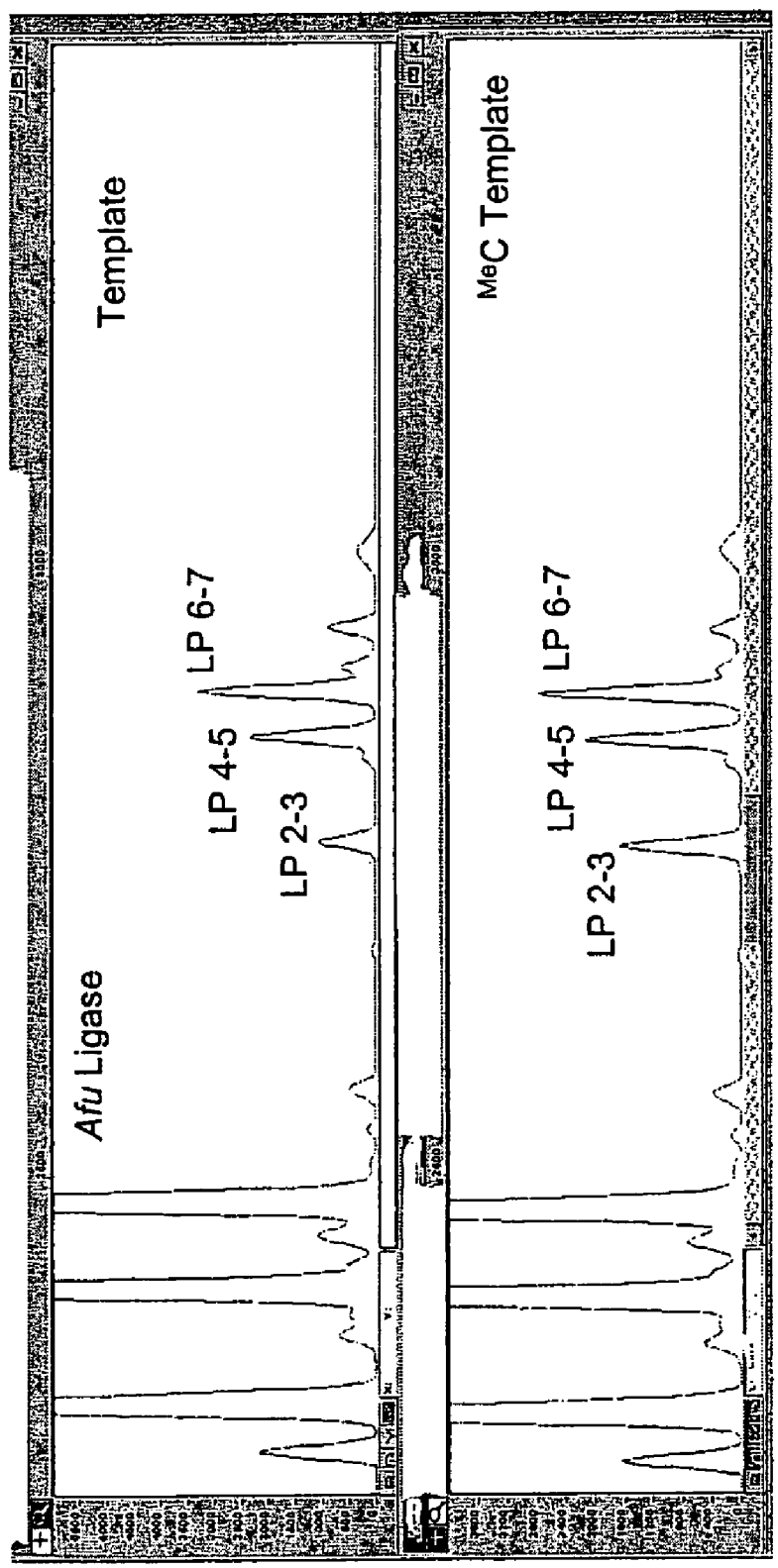
FIGS. 12A-D: depict electropherograms showing the ligation product peaks obtained from an illustrative analysis of four ligases in an exemplary methylation detection ligation assay, described in Example 10. The upper panels show the ligation product peaks LP 2-3 (probe set 1), LP 4-5 (probe set 2), and LP 6-7 (probe set 3) obtained using non-methylated template and the lower panels show the results obtained using the methylated synthetic template.
Figure 12B:
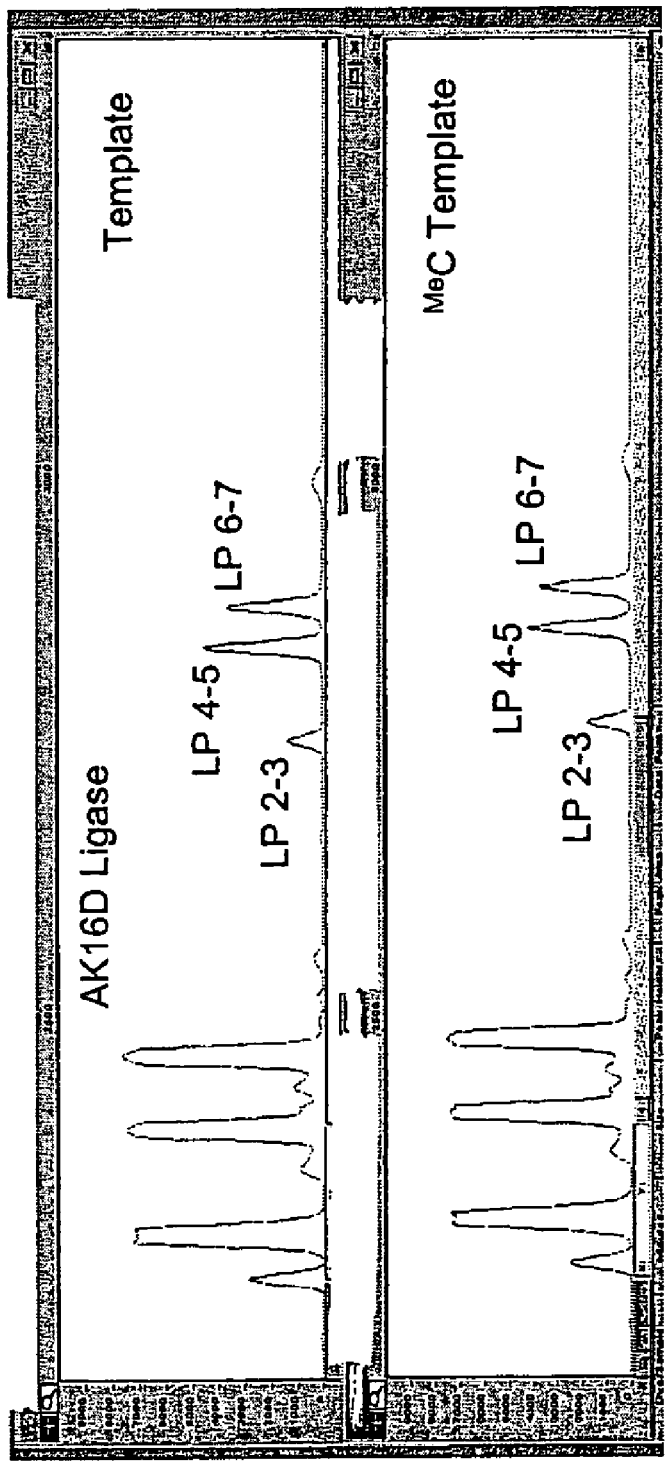
Figure 12C:
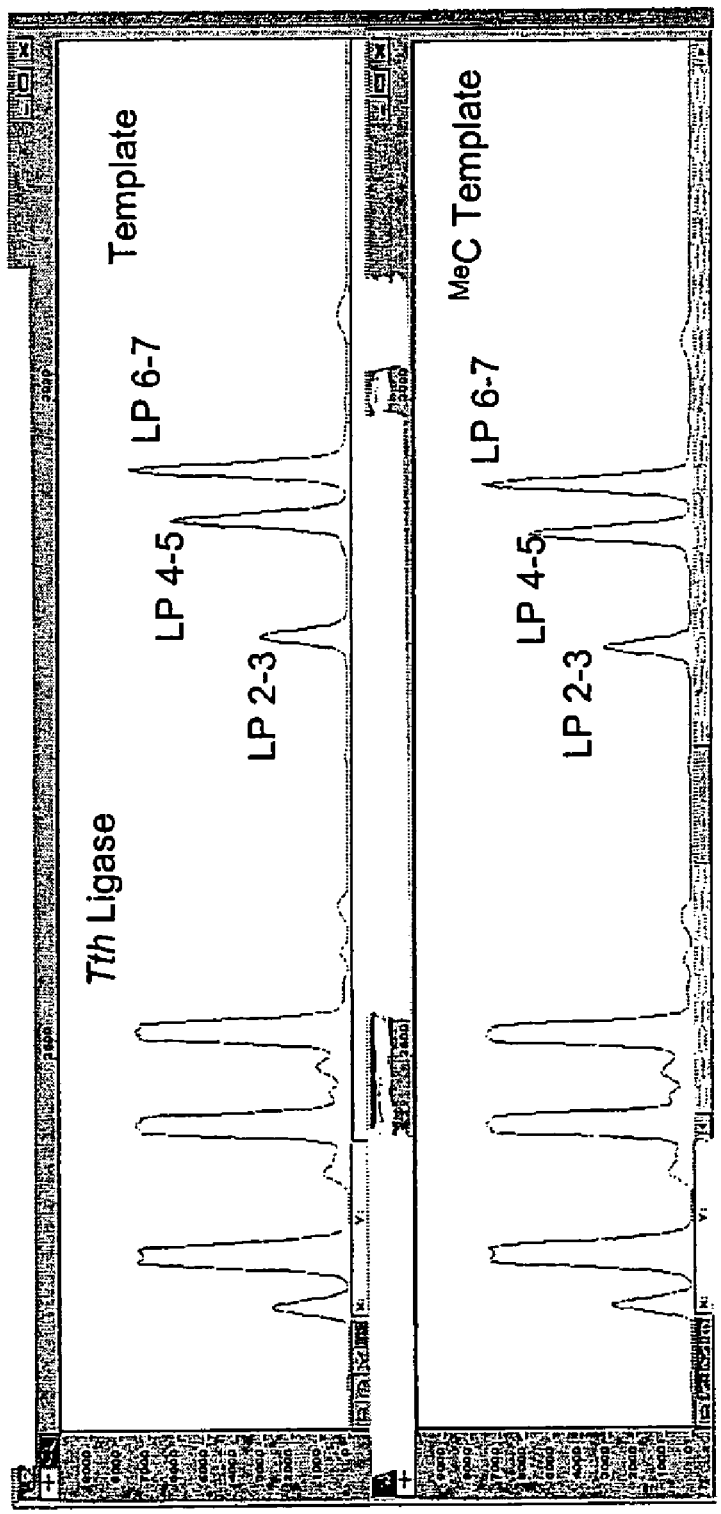
Figure 12D:
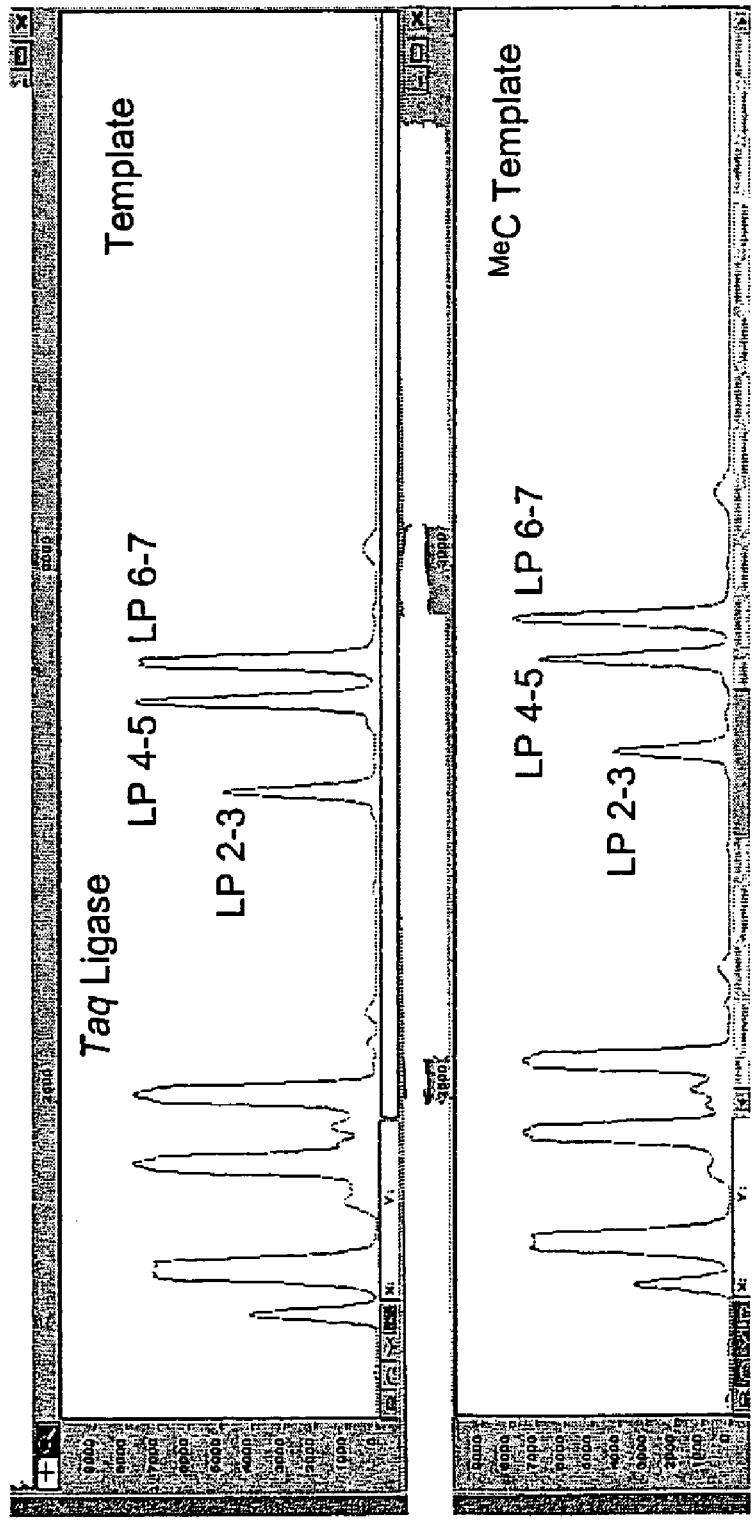

The detected ligation product peaks obtained with Afu ligase are shown in FIG. 12A. The ligation product ratio with the non-methylated and methylated template for LP 2-3/LP4-5 was 0.44 (non-methylated) and 0.78 (methylated); for LP 2-3/LP 6-7 was 0.32 (non-methylated) and 0.78 (methylated); and for LP 4-5/LP 6-7 was 0.72 (non-methylated) and 0.76 (methylated). The detected ligation product peaks obtained with AK16D ligase are shown in FIG. 12B. The ligation product ratio with the non-methylated and methylated template for LP 2-3/LP4-5 was 0.30 and 0.41, respectively; for LP 2-3/LP 6-7 was 0.37 and 0.46, respectively; and for LP 4-5/LP 6-7 was 1.24 and 1.12, respectively. The detected ligation product peaks obtained with Tth ligase are shown in FIG. 12C. The ligation product ratio with the non-methylated and methylated template for LP 2-3/LP4-5 was 0.50 and 0.53, respectively; for LP 2-3/LP 6-7 was 0.41 and 0.42, respectively; and for LP 4-5/LP 6-7 was 0.82 and 0.79, respectively. The detected ligation product peaks obtained with Taq ligase are shown in FIG. 12D. The ligation product ratio with the non-methylated and methylated template for LP 2-3/LP4-5 was 0.58 and 0.60, respectively; for LP 2-3/LP 6-7 was 0.51 and 0.47, respectively; and for LP 4-5/LP 6-7 was 0.87 and 0.78, respectively. Those in the art will appreciate that similar evaluations of additional ligases can be preformed using the same or different templates and/or probes to evaluate the potential of those ligases for detecting methylated target nucleotides under a given set of experimental conditions.

While the present teachings have been described in terms of these exemplary embodiments, the skilled artisan will readily understand that numerous variations and modifications of these exemplary embodiments are possible without undue experimentation. All such variations and modifications are within the scope of the current teachings.

We claim:

1. A method for determining the degree of methylation of at least one target nucleotide in at least one target nucleic acid sequence, comprising:
    forming a misligation reaction composition comprising (a) the at least one target nucleic acid sequence, (b) at least one ligation probe set comprising at least one first probe and at least one second probe, wherein the at least one first probe comprises at least one first target-specific portion with at least one nucleotide mismatches the target nucleotide sequence and the at least one second probe comprises at least one second target-specific portion wherein at least one nucleotide mismatches the target nucleotide sequence, wherein the two portions are adjacent to one another and (c) at least one ligation agent;
    subjecting the misligation reaction composition to at least one cycle of ligation to generate at least one misligation product; and
    determining the degree of methylation of the at least one target nucleotide.

2. The method of claim 1, wherein at least one probe of at least one ligation probe set comprises at least one target-specific portion comprising: at least one Modification, at least one mismatched nucleotide relative to at least one portion of the at least one target nucleic acid sequence, or at least one Modification and at least one mismatched nucleotide.

3. The method of claim 2, wherein the at least one Modification comprises at least one substituted hydrocarbon, at least one ribonucleotide, at least one amide bond, at least one glycosidic bond, at least one locked nucleic acid (LNA), at least one nucleotide analog, at least one groove binder, or combinations thereof.

4. The method of claim 2, wherein at least one ligation product further comprises at least one primer-binding portion, at least one reporter group, at least one mobility modifier, at least one hybridization tag, at least one reporter probe-binding portion, at least one affinity tag, or combinations thereof.

5. The method of claim 4, wherein the determining comprises detecting the at least one reporter group of at least some ligation products and comparing the ratio of the ligation products of at least one ligation probe set.

6. The method of claim 4, further comprising combining at least some of the ligation products with at least one reporter probe.

7. The method of claim 6, wherein the determining comprises detecting the at least one reporter probe and comparing the ratio of the ligation products of at least one ligation probe set.

8. The method of claim 4, further comprising, combining at least one hybridization tag complement comprising at least one reporter group with the at least one ligation product; and wherein the determining comprises detecting the at least one reporter group of the at least one hybridization tag complement.

9. The method of claim 4, further comprising amplifying at least one ligation product to generate at least one amplified ligation product.

10. The method of claim 9, wherein the amplifying comprises at least one primer, at least one universal primer, or at least one primer and at least one universal primer.

11. The method of claim 9, wherein the at least one amplified ligation product comprises at least one primer-binding portion, at least one reporter group, at least one mobility modifier, at least one hybridization tag, at least one reporter probe-binding portion, at least one affinity tag, or combinations thereof.

12. The method of claim 11, wherein the determining comprises detecting the at least one reporter group of at least some amplified ligation products and comparing the ratio of the amplified ligation products of at least one ligation probe set.

13. The method of claim 11, further comprising, combining at least one hybridization tag complement comprising at least one reporter group with the at least one amplified ligation product; and wherein the determining comprises detecting the at least one reporter group of the at least one hybridization tag complement.

14. The method of claim 11, further comprising combining at least some of the amplified ligation products with at least one reporter probe.

15. The method of claim 14, wherein the determining comprises detecting at least one reporter probe and comparing the ratio of the amplified ligation products of at least one ligation probe set.

16. The method of claim 1, wherein the ligation agent comprises at least one thermostable ligase, at least one chemical ligation agent, at least one photoligation agent, or combinations thereof.

17. The method of claim 16, wherein the at least one thermostable ligase comprises at least one of AN ligase, Pfu ligase, Taq ligase, *Thermus* species ligase AK16D, Tth ligase, Tsc ligase, Tfi ligase, Mth ligase, Ape ligase, TS2126 ligase, or combinations thereof.

18. The method of claim 1, wherein the at least one cycle of ligation comprises a multiplicity of cycles of ligation.

19. The method of claim 1, wherein the determining comprises separating the at least one ligation product using at least one mobility dependent analytical technique.

20. The method of claim 19, wherein the at least one mobility dependent analytical technique comprises capillary electrophoresis.

21. The method of claim 1, wherein the determining comprises quantifying at least one ligation product.

22. The method of claim 21, wherein the quantifying comprises quantitative polymerase chain reaction (Q-PCR).

23. The method of claim 22, wherein the Q-PCR comprises at least one 5'-exonuclease probe, at least one molecular beacon probe, at least one peptide nucleic acid (PNA) probe, at least one LNA probe, at least one nucleic acid dye, or combinations thereof.

24. The method of claim 2, wherein the ligation agent comprises at least one thermostable ligase; at least one ligation product comprises at least one primer-binding portion, at least one reporter group, at least one mobility modifier, at least one hybridization tag, at least one reporter probe-binding portion, at least one affinity tag, or combinations thereof; and further comprising amplifying at least one ligation product to generate at least one amplified ligation product, wherein the at least one amplified ligation product comprises at least one primer-binding portion, at least one reporter group, at least one mobility modifier, at least one hybridization tag, at least one reporter probe-binding portion, at least one affinity tag, or combinations thereof.

25. The method of claim 24, wherein the determining comprises: (a) separating the at least one ligation product or the at least one amplified ligation product, or at least one ligation product and the at least one amplified ligation product using at least one mobility dependent analytical technique, (b) detecting the at least one reporter group on at least one ligation product, at least one amplified ligation product, or at least one ligation product and at least one amplified ligation product, and (c) comparing the ratio of: (i) the ligation products of at least two probe sets, (ii) the amplified ligation products from the at least two probe sets, or (iii) the ligation products from the at least two probe sets and the amplified ligation products from the at least two probe sets.

26. The method of claim 25, wherein the at least one thermostable ligase comprises Afu ligase and the mobility dependent analytical technique comprises capillary electrophoresis.

27. The method of claim 24, further comprising, combining at least one hybridization tag complement comprising at least one reporter group with the at least one amplified ligation product; and wherein the determining comprises detecting the at least one reporter group of the at least one hybridization tag complement.

28. The method of claim 24, further comprising combining at least some of the amplified ligation product with at least one reporter probe.

29. The method of claim 28, wherein the determining comprises detecting the at least one reporter probe and comparing ligation rate of the amplified ligation products of at least two ligation probe sets.

30. The method of claim 28, wherein the thermostable ligase comprises Afu ligase and the determining comprises quantifying the amplified ligation product using Q-PCR.

31. The method of claim 4, further comprising: digesting the at least one ligation product with at least one 3'-5' exonuclease, at least one 5'-3' exonuclease, or at least one 3'-5' exonuclease and at least one 5'-3' exonuclease, to generate at least one digested ligation product; amplifying the at least one digested ligation product to generate at least one amplified digested ligation product; combining at least one hybridization tag complement comprising at least one reporter group with the at least one amplified digested ligation product; and wherein the determining comprises detecting the at least one reporter group of the at least one hybridization tag complement.

32. A method for determining the degree of methylation of at least one target nucleotide in at least one target nucleic acid sequence, comprising:

forming a misligation reaction composition comprising the at least one target nucleic acid sequence; at least two competing ligation probe sets, wherein each competing probe set comprises at least one first probe and at least one second probe and wherein the at least one first probe comprises at least one target-specific portion with at least one nucleotide mismatches the target nucleotide sequence and the at least one second probe comprises at least one target-specific portion wherein at least one nucleotide mismatches the target nucleotide sequence; wherein the two portions are adjacent to one another, and at least one ligation agent;

subjecting the misligation reaction composition to at least one cycle of ligation to generate at least one ligation product; and determining the degree of methylation of the at least one target nucleotide.

33. The method of claim 32, wherein the at least two competing probe sets do not share the same ligation site on the at least one target nucleic acid sequence.

34. The method of claim 32, wherein at least one probe of at least one competing probe set comprises at least one target-specific portion comprising: at least one Modification, at least one mismatched nucleotide relative to at least one portion of the at least one target nucleic acid sequence, or at least one Modification and at least one mismatched nucleotide.

35. The method of claim 34, wherein the at least one Modification comprises at least one substituted hydrocarbon, at least one ribonucleotide, at least one amide bond, at least one glycosidic bond, at least one LNA, at least one nucleotide analog, at least one groove binder, or combinations thereof.

36. The method of claim 32, wherein at least one ligation product further comprises at least one primer-binding portion, at least one reporter group, at least one mobility modifier, at least one hybridization tag, at least one reporter probe-binding portion, at least one affinity tag, or combinations thereof.

37. The method of claim 36, further comprising: digesting the at least one ligation product with at least one 3'-5' exonuclease, at least one 5'-3' exonuclease, or at least one 3'-5' exonuclease and at least one 5'-3' exonuclease, to generate at least one digested ligation product; amplifying the at least one digested ligation product to generate at least one amplified digested ligation product; combining at least one hybridization tag complement comprising at least one reporter group with the at least one amplified digested ligation product; and wherein the determining comprises detecting the at least one reporter group of the at least one hybridization tag complement.

38. The method of claim 36, wherein the determining comprises detecting the at least one reporter group of at least some ligation products and comparing the ratio of the ligation products of at least two ligation probe sets.

39. The method of claim 36, further comprising, combining at least one hybridization tag complement comprising at least one reporter group with the at least one ligation product; and wherein the determining comprises detecting the at least one reporter group of the at least one hybridization tag complement.

40. The method of claim 36, further comprising combining at least some of the ligation product and at least one reporter probe.

41. The method of claim 40, wherein the determining comprises detecting the at least one reporter probe and comparing the ratio of the ligation products of at least two ligation probe sets.

42. The method of claim 36, further comprising amplifying at least one ligation product to generate at least one amplified ligation product.

43. The method of claim 42, wherein the amplifying comprises at least one primer, at least one universal primer, or at least one primer and at least one universal primer.

44. The method of claim 42, wherein the at least one amplified ligation product comprises at least one primer-binding portion, at least one reporter group, at least one mobility modifier, at least one hybridization tag, at least one reporter probe-binding portion, at least one affinity tag, or combinations thereof.

45. The method of claim 42, wherein the determining comprises detecting the at least one reporter group of at least some amplified ligation products and evaluating the ligation rate of the amplified ligation products of at least two ligation probe sets.

46. The method of claim 44, further comprising, combining at least one hybridization tag complement comprising at least one reporter group with the at least one amplified ligation product; and wherein the determining comprises detecting the at least one reporter group of the at least one hybridization tag complement.

47. The method of claim 44, further comprising combining at least some of the amplified ligation product with at least one reporter probe.

48. The method of claim 47, wherein the determining comprises detecting the at least one reporter probe and evaluating the ligation rate of the amplified ligation products of at least two probe sets.

49. The method of claim 32, wherein the ligation agent comprises at least one thermostable ligase, at least one chemical ligation agent, at least one photoligation agent, or combinations thereof.

50. The method of claim 49, wherein the at least one thermostable ligase comprises at least one of: Afu ligase, Phi ligase, Taq ligase, *Thermus* species ligase AK16D, Tth ligase, Tsc ligase, Tfi ligase, Mth ligase, Ape ligase, TS2126 ligase, or combinations thereof.

51. The method of claim 32, wherein the at least one cycle of ligation comprises a multiplicity of cycles of ligation.

52. The method of claim 32, wherein the determining comprises separating the at least one ligation product using at least one mobility dependent analytical technique.

53. The method of claim 52, wherein the at least one mobility dependent analytical technique comprises capillary electrophoresis.

54. The method of claim 32, wherein the determining comprises quantifying at least one ligation product.

55. The method of claim 54, wherein the quantifying comprises Q-PCR.

56. The method of claim 55, wherein the Q-PCR comprises at least one 5'-exonuclease probe, at least one molecular beacon probe, at least one PNA probe, at least one LNA probe, at least one nucleic acid dye, or combinations thereof.

57. The method of claim 32, wherein the ligation agent comprises at least one thermostable ligase; at least one ligation product comprises at least one primer-binding portion, at least one reporter group, at least one mobility modifier, at least one hybridization tag, at least one reporter probe-binding portion, at least one affinity tag, or combinations thereof; and further comprising amplifying at least one ligation product to generate at least one amplified ligation product, wherein the at least one amplified ligation product comprises at least one primer-binding portion, at least one reporter group, at least one mobility modifier, at least one hybridization tag, at least one reporter probe-binding portion, at least one affinity tag, or combinations thereof.

58. The method of claim 57, further comprising, combining at least one hybridization tag complement comprising at least one reporter group with the at least one amplified ligation product; and wherein the determining comprises detecting the at least one reporter group of the at least one hybridization tag complement.

59. The method of claim 58, wherein the determining comprises: (a) separating the at least one ligation product or the at least one amplified ligation product, or the at least one ligation product and the at least one amplified ligation product using at least one mobility dependent analytical technique, (b) detecting the at least one reporter group on at least some ligation products, at least some amplified ligation products, or at least some ligation products and at least some amplified ligation products, and (c) comparing the ratio of: (i) the ligation products of at least two competing probe sets, (ii) the amplified ligation products from the at least two competing probe sets, or (iii) the ligation products formed from the at least two competing probe sets and the amplified ligation products from the at least two competing probe sets.

60. The method of claim 59, wherein the at least one thermostable ligase comprises Afu ligase and the mobility dependent analytical technique comprises capillary electrophoresis.

61. The method of claim 57, further comprising combining at least some of the amplified ligation product with at least one reporter probe.

62. The method of claim 61, wherein the determining comprises detecting the at least one reporter probe and comparing the amplified ligation products of at least two ligation probe sets.

63. The method of claim 61, wherein the thermostable ligase comprises Afu ligase and the determining comprises quantifying the amplified ligation product using Q-PCR.

64. The method of claim 33, wherein at least one ligation product further comprises at least one primer-binding portion, at least one reporter group, at least one mobility modifier, at least one hybridization tag, at least one reporter probe-binding portion, at least one affinity tag, or combinations thereof.

65. The method of claim 64, further comprising: digesting the at least one ligation product with at least one 3'-5' exonuclease, at least one 5'-3' exonuclease, or at least one 3'-5' exonuclease and at least one SKY exonuclease, to generate at least one digested ligation product; amplifying the at least one digested ligation product to generate at least one amplified digested ligation product; combining at least one hybridization tag complement comprising at least one reporter group with the at least one amplified digested ligation product; and wherein the determining comprises detecting the at least one reporter group of the at least one hybridization tag complement.

66. A method for determining the degree of methylation of at least one target nucleotide in at least one target nucleic acid sequence, comprising:
  at least one step for interrogating the at least one target nucleotide;
  at least one step for generating at least one misligation product; and
  at least one step for determining the degree of methylation of the at least one target nucleotide.

67. A method for determining the degree of methylation of at least one target nucleotide in at least one target nucleic acid sequence, comprising:
  at least one step for interrogating the at least one target nucleotide;
  at least one step for generating at least one misligation product;
  at least one step for generating at least one amplified misligation ligation product; and
  at least one step for determining the degree of methylation of the at least one target nucleotide.

68. A method for determining the degree of methylation of at least one target nucleotide in at least one target nucleic acid sequence, comprising:
  at least one step for interrogating the at least one target nucleotide;
  at least one step for generating at least one misligation product;
  at least one step for generating at least one digested misligation product; and
  at least one step for determining the degree of methylation of the at least one target nucleotide.

69. A method for determining the degree of methylation of at least one target nucleotide in at least one target nucleic acid sequence, comprising:
  at least one step for interrogating the at least one target nucleotide;
  at least one step for generating at least one misligation product;
  at least one step for generating at least part of at least one digested misligation product;
  at least one step for generating at least one amplified digested misligation product; and
  at least one step for determining the degree of methylation of the at least one target nucleotide.

70. The method of claim 1, wherein the at least one target nucleotide comprises a multiplicity of different target nucleotides, the at least one probe set comprises a multiplicity of different probe sets, and the degree of methylation of a multiplicity of different target nucleotides is determined.

71. The method of claim 32, wherein the at least two competing probe sets comprises at least two different competing probe sets and the degree of methylation of a multiplicity of different target nucleotides is determined.

* * * * *

UNITED STATES PATENT AND TRADEMARK OFFICE
CERTIFICATE OF CORRECTION

PATENT NO. : 7,364,855 B2 Page 1 of 1
APPLICATION NO. : 11/119985
DATED : April 29, 2008
INVENTOR(S) : Mark R. Anderson et al.

It is certified that error appears in the above-identified patent and that said Letters Patent is hereby corrected as shown below:

Claim 17, Column 65, line 30, please replace "AN" with --Afu--

Claim 50, Column 68, line 15, please replace "Phi" with --Pfu--

Claim 50, Column 68, line 16, please replace "Tag" with --Taq--

Claim 55, Column 68, line 30, please replace "Q-POR" with --Q-PCR--

Claim 65, Column 69, line 24, please replace "SKY" with --5'-3'--

Claim 67, Column 70, line 6, please delete "ligation"

Signed and Sealed this

Twelfth Day of August, 2008

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 35
<212> TYPE: DNA
<213> ORGANISM: Artificial Sequence
<220> FEATURE:
<223> OTHER INFORMATION: Synthetic DNA

<400> SEQUENCE: 1
ttattatgtg gggcggaccg cgtgcgctta cttat                              35

<210> SEQ ID NO 2
<211> LENGTH: 10
<212> TYPE: DNA
<213> ORGANISM: Artificial Sequence
<220> FEATURE:
<223> OTHER INFORMATION: Synthetic DNA

<400> SEQUENCE: 2
agcgcacgcg                                                          10

<210> SEQ ID NO 3
<211> LENGTH: 11
<212> TYPE: DNA
<213> ORGANISM: Artificial Sequence
<220> FEATURE:
<223> OTHER INFORMATION: Synthetic DNA

<400> SEQUENCE: 3
gtccgcccca c                                                        11

<210> SEQ ID NO 4
<211> LENGTH: 12
<212> TYPE: DNA
<213> ORGANISM: Artificial Sequence
```

```
<220> FEATURE:
<223> OTHER INFORMATION: Synthetic DNA

<400> SEQUENCE: 4
agcgcacgcg gt                                                           12

<210> SEQ ID NO 5
<211> LENGTH: 11
<212> TYPE: DNA
<213> ORGANISM: Artificial Sequence
<220> FEATURE:
<223> OTHER INFORMATION: Syntetic DNA

<400> SEQUENCE: 5
ccgccccaca t                                                            11

<210> SEQ ID NO 6
<211> LENGTH: 13
<212> TYPE: DNA
<213> ORGANISM: Artificial Sequence
<220> FEATURE:
<223> OTHER INFORMATION: Synthetic DNA

<400> SEQUENCE: 6
agcgcacgcg gtc                                                          13

<210> SEQ ID NO 7
<211> LENGTH: 11
<212> TYPE: DNA
<213> ORGANISM: Artificial Sequence
<220> FEATURE:
<223> OTHER INFORMATION: Synthetic DNA

<400> SEQUENCE: 7
cgccccacat a                                                            11

<210> SEQ ID NO 8
<211> LENGTH: 10
<212> TYPE: DNA
<213> ORGANISM: Artificial Sequence
<220> FEATURE:
<223> OTHER INFORMATION: Synthetic DNA

<400> SEQUENCE: 8
agcgcactca                                                              10

<210> SEQ ID NO 9
<211> LENGTH: 10
<212> TYPE: DNA
<213> ORGANISM: Artificial Sequence
<220> FEATURE:
<223> OTHER INFORMATION: Synthetic DNA

<400> SEQUENCE: 9
agcgcactcc                                                              10

<210> SEQ ID NO 10
<211> LENGTH: 11
<212> TYPE: DNA
<213> ORGANISM: Artificial Sequence
<220> FEATURE:
<223> OTHER INFORMATION: Synthetic DNA

<400> SEQUENCE: 10
gtccgcccca c                                                            11
```

<210> SEQ ID NO 11
<211> LENGTH: 10
<212> TYPE: DNA
<213> ORGANISM: Artificial Sequence
<220> FEATURE:
<223> OTHER INFORMATION: Synthetic DNA

<400> SEQUENCE: 11
agcgcactct                                                           10

<210> SEQ ID NO 12
<211> LENGTH: 43
<212> TYPE: DNA
<213> ORGANISM: Artificial Sequence
<220> FEATURE:
<223> OTHER INFORMATION: Synthetic DNA

<400> SEQUENCE: 12
tccgggatgc acagtgcaga ggcggccaga gcagtgcaca gcg                      43

<210> SEQ ID NO 13
<211> LENGTH: 14
<212> TYPE: DNA
<213> ORGANISM: Artificial Sequence
<220> FEATURE:
<223> OTHER INFORMATION: Synthetic DNA

<400> SEQUENCE: 13
cactgctctg gcca                                                      14

<210> SEQ ID NO 14
<211> LENGTH: 14
<212> TYPE: DNA
<213> ORGANISM: Artificial Sequence
<220> FEATURE:
<223> OTHER INFORMATION: Synthetic DNA

<400> SEQUENCE: 14
cactgctctg gccc                                                      14

<210> SEQ ID NO 15
<211> LENGTH: 14
<212> TYPE: DNA
<213> ORGANISM: Artificial Sequence
<220> FEATURE:
<223> OTHER INFORMATION: Synthetic DNA

<400> SEQUENCE: 15
cactgctctg gcct                                                      14

<210> SEQ ID NO 16
<211> LENGTH: 16
<212> TYPE: DNA
<213> ORGANISM: Artificial Sequence
<220> FEATURE:
<223> OTHER INFORMATION: Synthetic DNA

<400> SEQUENCE: 16
cctctgcact gtgcat                                                    16

<210> SEQ ID NO 17
<211> LENGTH: 36
<212> TYPE: DNA
<213> ORGANISM: Artificial Sequence
<220> FEATURE:
<223> OTHER INFORMATION: Synthetic DNA

```
<400> SEQUENCE: 17
ccagagggtg gggcggaccg agtgcgctcg gcggct                                        36

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA

<400> SEQUENCE: 18
gcgacgatga gtcctgagta a                                                        21

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA

<400> SEQUENCE: 19
ctcgtagact gcgtaccgat c                                                        21

<210> SEQ ID NO 20
<211> LENGTH: 56
<212> TYPE: DNA
<213> ORGANISM: Artificial Sequence
<220> FEATURE:
<223> OTHER INFORMATION: Synthetic DNA

<400> SEQUENCE: 20
ctcgtagact gcgtaccgat ccgtcggcac gcttcagttt gaatcgagcg cactct                  56

<210> SEQ ID NO 21
<211> LENGTH: 16
<212> TYPE: DNA
<213> ORGANISM: Artificial Sequence
<220> FEATURE:
<223> OTHER INFORMATION: Synthetic DNA

<400> SEQUENCE: 21
actctgcact gtgcat                                                              16

<210> SEQ ID NO 22
<211> LENGTH: 14
<212> TYPE: DNA
<213> ORGANISM: Artificial Sequence
<220> FEATURE:
<223> OTHER INFORMATION: Synthetic DNA

<400> SEQUENCE: 22
cactgctctg gccg                                                                14

<210> SEQ ID NO 23
<211> LENGTH: 16
<212> TYPE: DNA
<213> ORGANISM: Artificial Sequence
<220> FEATURE:
<223> OTHER INFORMATION: Synthetic DNA

<400> SEQUENCE: 23
gctctgcact gtgcat                                                              16

<210> SEQ ID NO 24
```

<210> SEQ ID NO 24
<211> LENGTH: 16
<212> TYPE: DNA
<213> ORGANISM: Artificial Sequence
<220> FEATURE:
<223> OTHER INFORMATION: Synthetic DNA

<400> SEQUENCE: 24
tctctgcact gtgcat                                                         16

<210> SEQ ID NO 25
<211> LENGTH: 35
<212> TYPE: DNA
<213> ORGANISM: Artificial Sequence
<220> FEATURE:
<223> OTHER INFORMATION: Synthetic DNA

<400> SEQUENCE: 25
ctcgtagact gcgtaccgat ccactgctct ggccg                                    35

<210> SEQ ID NO 26
<211> LENGTH: 37
<212> TYPE: DNA
<213> ORGANISM: Artificial Sequence
<220> FEATURE:
<223> OTHER INFORMATION: Synthetic DNA

<400> SEQUENCE: 26
actctgcact gtgcatttac tcaggactca tcgtcgc                                  37

<210> SEQ ID NO 27
<211> LENGTH: 41
<212> TYPE: DNA
<213> ORGANISM: Artificial Sequence
<220> FEATURE:
<223> OTHER INFORMATION: Synthetic DNA

<400> SEQUENCE: 27
gctctgcact gtgcattttt ttactcagga ctcatcgtcg c                             41

<210> SEQ ID NO 28
<211> LENGTH: 41
<212> TYPE: DNA
<213> ORGANISM: Artificial Sequence
<220> FEATURE:
<223> OTHER INFORMATION: Synthetic DNA

<400> SEQUENCE: 28
tctctgcact gtgcattttt ttactcagga ctcatcgtcg c                             41

<210> SEQ ID NO 29
<211> LENGTH: 21
<212> TYPE: DNA
<213> ORGANISM: Artificial Sequence
<220> FEATURE:
<223> OTHER INFORMATION: Synthetic DNA

<400> SEQUENCE: 29
ctcgtagact gcgtaccgat c                                                   21

<210> SEQ ID NO 30
<211> LENGTH: 21
<212> TYPE: DNA
<213> ORGANISM: Artificial Sequence
<220> FEATURE:
<223> OTHER INFORMATION: Synthetic DNA

<400> SEQUENCE: 30

```
gcgacgatga gtcctgagta a                                             21

<210> SEQ ID NO 31
<211> LENGTH: 61
<212> TYPE: DNA
<213> ORGANISM: Artificial Sequence
<220> FEATURE:
<223> OTHER INFORMATION: Synthetic DNA

<400> SEQUENCE: 31
actctgcact gtgcattcgc agattgtgtc tcaccgagga ttactcagga ctcatcgtcg   60
c                                                                   61

<210> SEQ ID NO 32
<211> LENGTH: 62
<212> TYPE: DNA
<213> ORGANISM: Artificial Sequence
<220> FEATURE:
<223> OTHER INFORMATION: Synthetic DNA

<400> SEQUENCE: 32
gctctgcact gtgcatcgat tcaaactgaa gcgtgccgac gttactcagg actcatcgtc   60
gc                                                                  62

<210> SEQ ID NO 33
<211> LENGTH: 62
<212> TYPE: DNA
<213> ORGANISM: Artificial Sequence
<220> FEATURE:
<223> OTHER INFORMATION: Synthetic DNA

<400> SEQUENCE: 33
tctctgcact gtgcatcgat tcaaactgaa gcgtgccgac gttactcagg actcatcgtc   60
gc                                                                  62

<210> SEQ ID NO 34
<211> LENGTH: 21
<212> TYPE: DNA
<213> ORGANISM: Artificial Sequence
<220> FEATURE:
<223> OTHER INFORMATION: Synthetic DNA

<400> SEQUENCE: 34
ctcgtagact gcgtaccgat c                                             21

<210> SEQ ID NO 35
<211> LENGTH: 21
<212> TYPE: DNA
<213> ORGANISM: Artificial Sequence
<220> FEATURE:
<223> OTHER INFORMATION: Synthetic DNA

<400> SEQUENCE: 35
gcgacgatga gtcctgagta a                                             21

<210> SEQ ID NO 36
<211> LENGTH: 55
<212> TYPE: DNA
<213> ORGANISM: Artificial Sequence
<220> FEATURE:
<223> OTHER INFORMATION: Synthetic DNA

<400> SEQUENCE: 36
```

-continued

```
ctcgtagact gcgtaccgat ctcctcggtg agacacaatc tgcgaagcgc actca        55

<210> SEQ ID NO 37
<211> LENGTH: 32
<212> TYPE: DNA
<213> ORGANISM: Artificial Sequence
<220> FEATURE:
<223> OTHER INFORMATION: Synthetic DNA

<400> SEQUENCE: 37
gtccgcccca cttactcagg actcatcgtc gc                                 32

<210> SEQ ID NO 38
<211> LENGTH: 56
<212> TYPE: DNA
<213> ORGANISM: Artificial Sequence
<220> FEATURE:
<223> OTHER INFORMATION: Synthetic DNA

<400> SEQUENCE: 38
ctcgtagact gcgtaccgat ccgtcggcac gcttcagttt gaatcgagcg cactcc       56

<210> SEQ ID NO 39
<211> LENGTH: 55
<212> TYPE: DNA
<213> ORGANISM: Artificial Sequence
<220> FEATURE:
<223> OTHER INFORMATION: Synthetic DNA

<400> SEQUENCE: 39
ctcgtagact gcgtaccgat ctcctcggtg agacacaatc tgcgaagcgc actcc        55
```